US012630505B2

(12) United States Patent
Nagata et al.

(10) Patent No.: US 12,630,505 B2
(45) Date of Patent: May 19, 2026

(54) ALKYNE COMPOUND, VITAMIN D COMPOUND, ANALYTICAL METHOD, AND PRODUCTION METHOD

(71) Applicants: Tokyo University of Agriculture and Technology, Tokyo (JP); JEOL Ltd., Tokyo (JP)

(72) Inventors: Akiko Nagata, Tokyo (JP); Yuka Mizumoto, Tokyo (JP); Ryota Sakamoto, Tokyo (JP); Kazuo Nagasawa, Tokyo (JP); Masaki Takiwaki, Tokyo (JP); Yoshikuni Kikutani, Tokyo (JP); Koji Takahashi, Tokyo (JP); Seketsu Fukuzawa, Tokyo (JP)

(73) Assignees: JEOL Ltd., Tokyo (JP); Tokyo University of Agriculture and Technology, Tokyo (JP)

( * ) Notice: Subject to any disclaimer, the term of this patent is extended or adjusted under 35 U.S.C. 154(b) by 559 days.

(21) Appl. No.: 18/087,881

(22) Filed: Dec. 23, 2022

(65) Prior Publication Data

US 2023/0242480 A1      Aug. 3, 2023

(30) Foreign Application Priority Data

Dec. 24, 2021    (JP) ................................. 2021-211040

(51) Int. Cl.
| | |
|---|---|
| *C07C 401/00* | (2006.01) |
| *C07F 7/18* | (2006.01) |
| *G01N 30/02* | (2006.01) |
| *G01N 30/72* | (2006.01) |

(52) U.S. Cl.
CPC .......... *C07C 401/00* (2013.01); *C07F 7/1804* (2013.01); *G01N 30/72* (2013.01); *G01N 2030/027* (2013.01)

(58) Field of Classification Search
CPC ..... C07C 401/00; C07F 7/1804; G01N 30/72; G01N 2030/027
See application file for complete search history.

(56) References Cited

U.S. PATENT DOCUMENTS

| | | | | |
|---|---|---|---|---|
| 4,410,515 A | * | 10/1983 | Holick | ................. C07H 15/207 424/180 |
| 5,446,225 A | | 8/1995 | Trost et al. | |

FOREIGN PATENT DOCUMENTS

| | | |
|---|---|---|
| CN | 107245045 A | 10/2017 |
| JP | H9507480 A | 7/1997 |
| JP | 2013513800 A | 4/2013 |
| WO | 2011072152 A1 | 6/2011 |

OTHER PUBLICATIONS

Kim, J. et al. Stereoselective Syntheses of 1β-D, and 1β-T, 1α-Hydroxyvitamin D. Deuteriation and Tritiation at a Non-Metabolic Position. Korean J. of Med. Chem. 1999, 9, 22-26. (Year: 1999).*
Sugimoto, K. et al. Synthesis of Denosomin-Vitamin D3 Hybrids and Evaluation of Their Anti-Alzheimer's Disease Activities. Org. Lett. 2015, 17, 5910-5913. (Year: 2015).*
Office Action issued in JP2021211040 on Mar. 19, 2024.
Wang et al., An Inducible Cytochrome P450 3A4-Dependent Vitamin D Catabolic Pathway, Molecular Pharmacology, vol. 81, No. 4, 2011, pp. 499-509.
Partial European Search Report issued in EP22215426.2 on Jun. 2, 2023.
Shea et al., Intramolecular ENE Reactions of 1,7-Octenynes: The Involvement of 1,2-Cyclooctadiene Intermediates, Tetrahedron Letters, vol. 29, No. 4, 1988, pp. 407-410.
Joonggon et al., Stereoselective Syntheses of 1B-D, and 1B-T, 1 a-Hydroxyvitamin D. Deuteriation and Tririation at a Non-Metabolic Position, The Korean Journal of Medicinal Chemistry, vol. 9, No. 1, 1999, pp. 22-26.
Holick et al., Chemical Synthesis of [1B-H]1a, 25-Dihydroxyvitamin D3 and [1a-3H]1B, 25-Dihydroxyvitamin D3: Biological Activity of 1B,25-Dihydroxyvitman D3, Biochemical and Biophysical Research Communications, vol. 97, No. 3, 1980, pp. 1031-1037.

(Continued)

*Primary Examiner* — Jeffrey H Murray
*Assistant Examiner* — Kristen W Romero
(74) *Attorney, Agent, or Firm* — The Webb Law Firm

(57)        ABSTRACT

The present invention is intended to provide a compound useful to analyze a vitamin D compound. The present invention provides an alkyne compound represented by Formula (I):

(I)

where in Formula (I), A is a linear carbon chain having an alkynyl group at an end and having a vinyl group at another end; $X_1$ is CH or $^{13}$CH; $X_2$ is CHY, CDY, $^{13}$CHY, $^{13}$CDY, CO, $^{13}$CO, C$^{18}$O, or $^{13}$C$^{18}$O; m is an integer from 1 to 4; when m is 2 or more, $X_2$s are identical or different; Y is H, D, $NH_2$, $^{15}NH_2$, OH, $^{18}$OH, SH, OR, O(CO)R, $OSO_3H$, $OSO_3Na$, or a sugar substituent; when Formula (I) contains two or more Ys, Ys are identical or different; R is an alcohol protective group, an alkyl group, an alkenyl group, or an aryl group; $X_3$ is C or $^{13}$C; and at least one selected from the group consisting of $X_1$, $X_2$(s), and $X_3$ is modified with a stable isotope D, $^{13}$C, $^{18}$O, or $^{15}$N.

4 Claims, 27 Drawing Sheets

(56) References Cited

OTHER PUBLICATIONS

Zagalak et al., Preparation of Deuterated Cholesterol, Calciol and Calcitriol as Internal Standards for GC:MS-Assays, International Journal of Spectroscopy, vol. 6, 1988, pp. 203-212.

Office Action issued in JP2021211040 on Sep. 3, 2024.

Ray et al., Synthesis of 25-hydroxy-[6,19,19'-2H3]vitamin D3 and 1α,25-dihydroxy-[6,19,19'-2H3]vitamin D3, Steroids, 1992, vol. 57, pp. 142-146.

Kaufmann et al., Differential diagnosis of vitamin D-related hypercalcemia using serum vitamin D metabolite profiling, Journal of Bone and Mineral Research, Jul. 2021, vol. 36, No. 7, pp. 1340-1350.

Mendoza et al., Controlled lipid β-oxidation and carnitine biosynthesis by a vitamin D metabolite, Cell Chemical Biology, Mar. 17, 2022, vol. 29, pp. 1-12.

Seki et al., A novel caged Cookson-type reagent toward a practical vitamin D derivatization method for mass spectrometric analyses, Rapid Communications in Mass Spectrometry, 2020, vol. 34:e8648, pp. 1-8.

Office Action issued in JP2021211040 on Dec. 3, 2024.

Communication issued in EP22215426.2 on Jun. 28, 2024.

Office Action issued in EP22215426.2 on Mar. 11, 2025.

Alezra et al., Fast ester cleavage of sterically hindered alpha- and beta-aminoesters under non-aqueous conditions. Application to the kinetic resolution of aziridine esters, Tetrahedron Letters vol. 41, 1999, pp. 655-658.

Foster, Deuterium Isotope Effects in the Metabolism of Drugs and Xenobiotics: Implications for Drug Design, Advances in Drug Research, vol. 14, 1985 pp. 1-40.

\* cited by examiner

[ Fig.1A ]
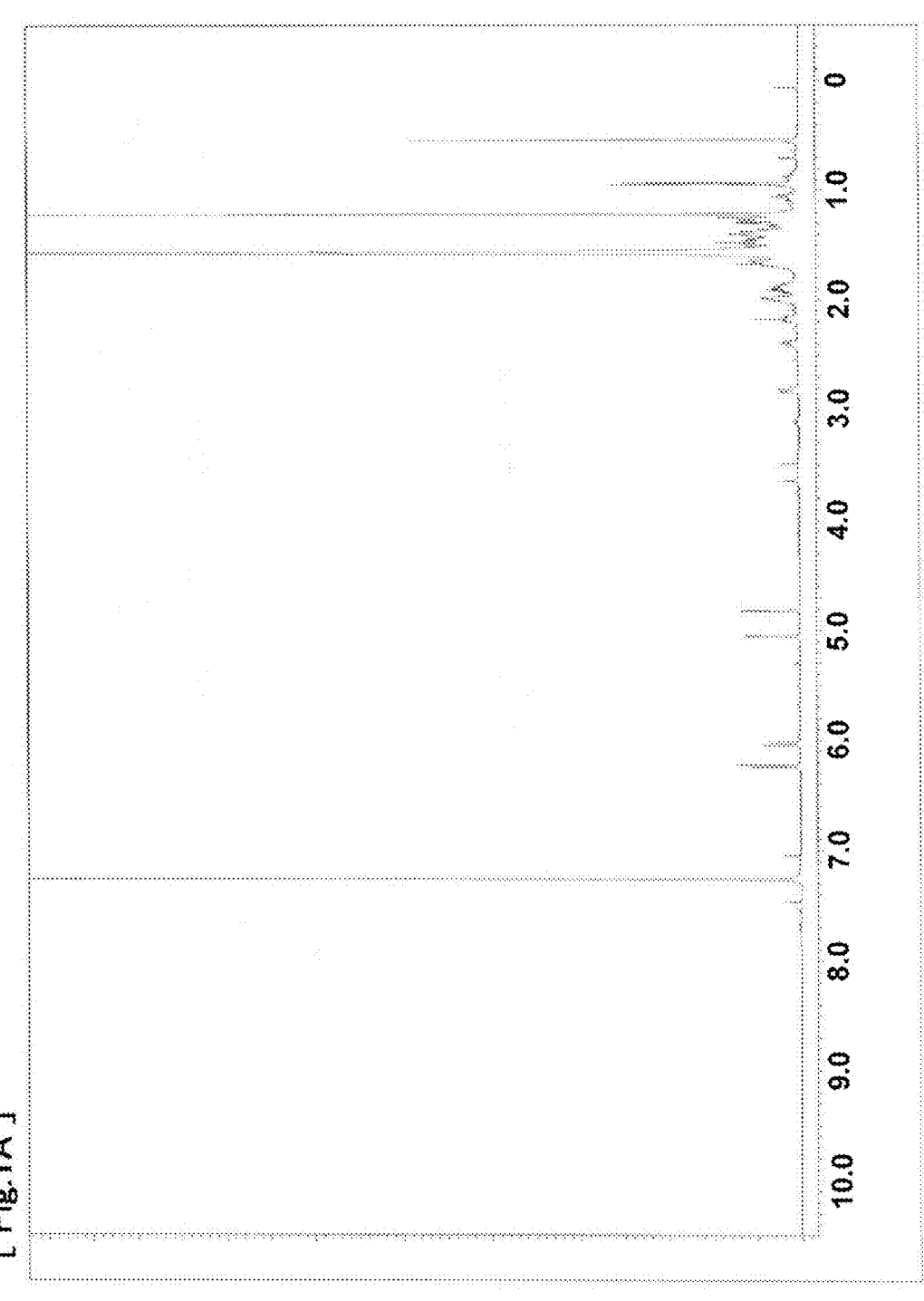

[ Fig.1B ]
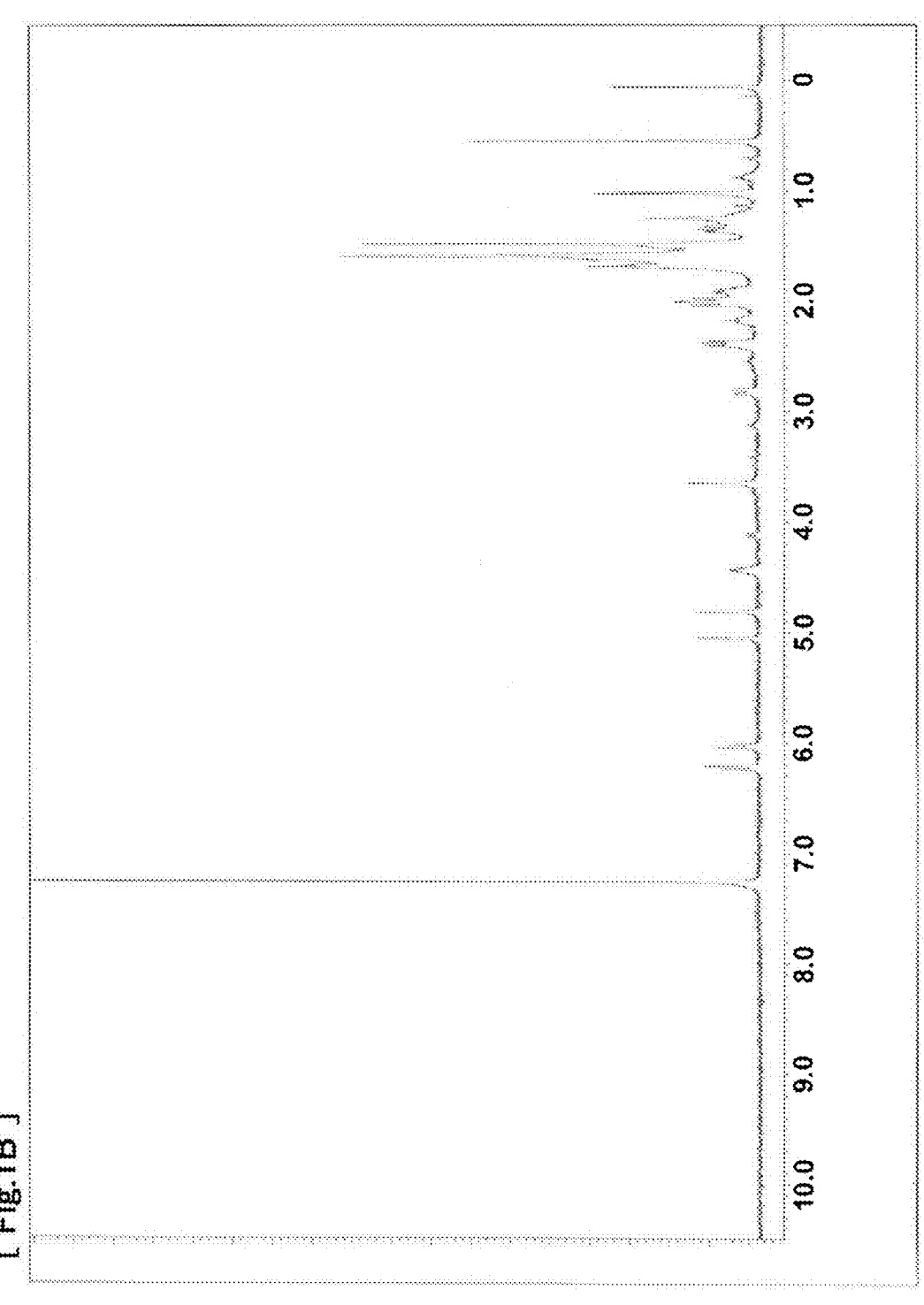

[ Fig.1C ]
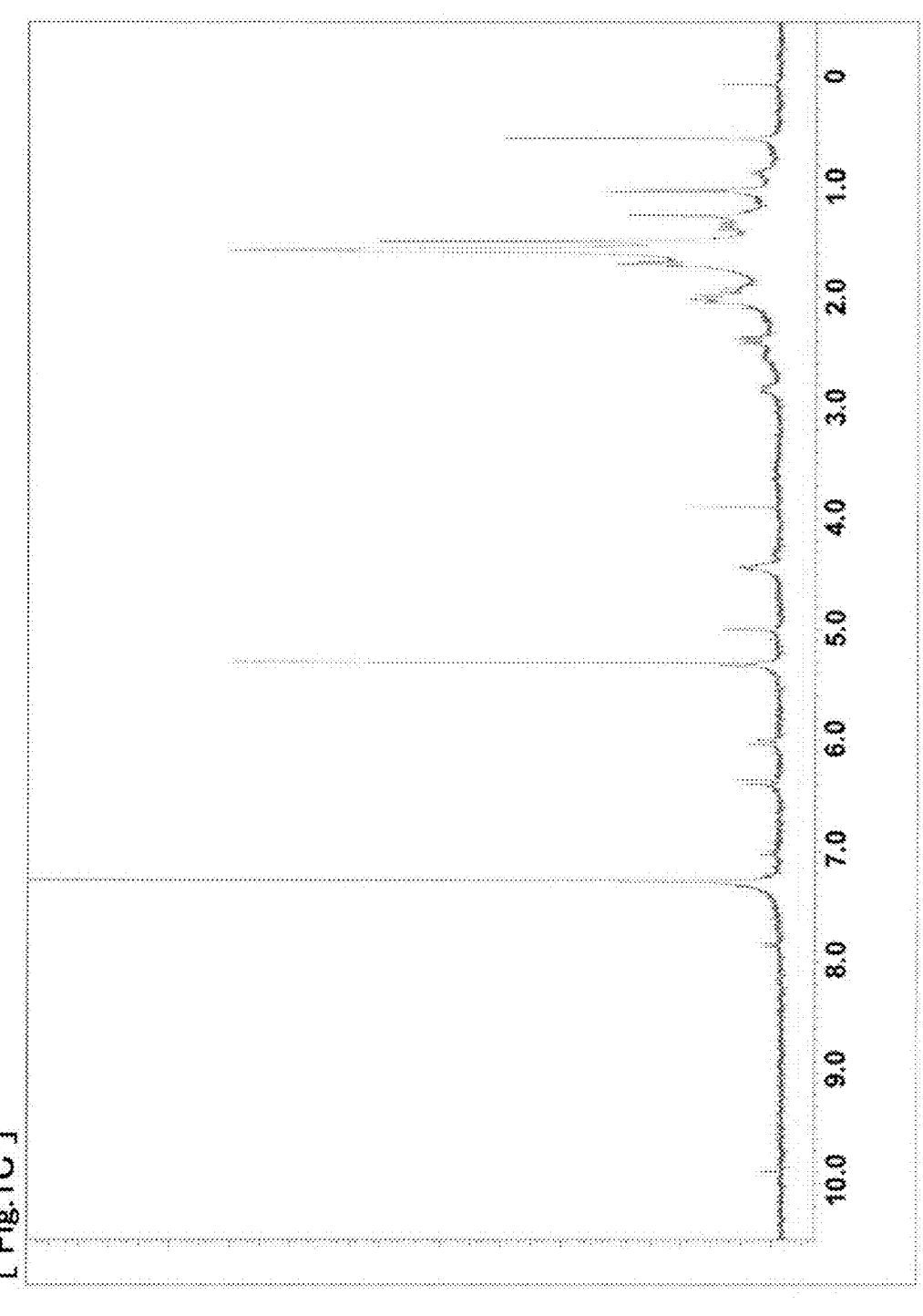

[ Fig.1D ]
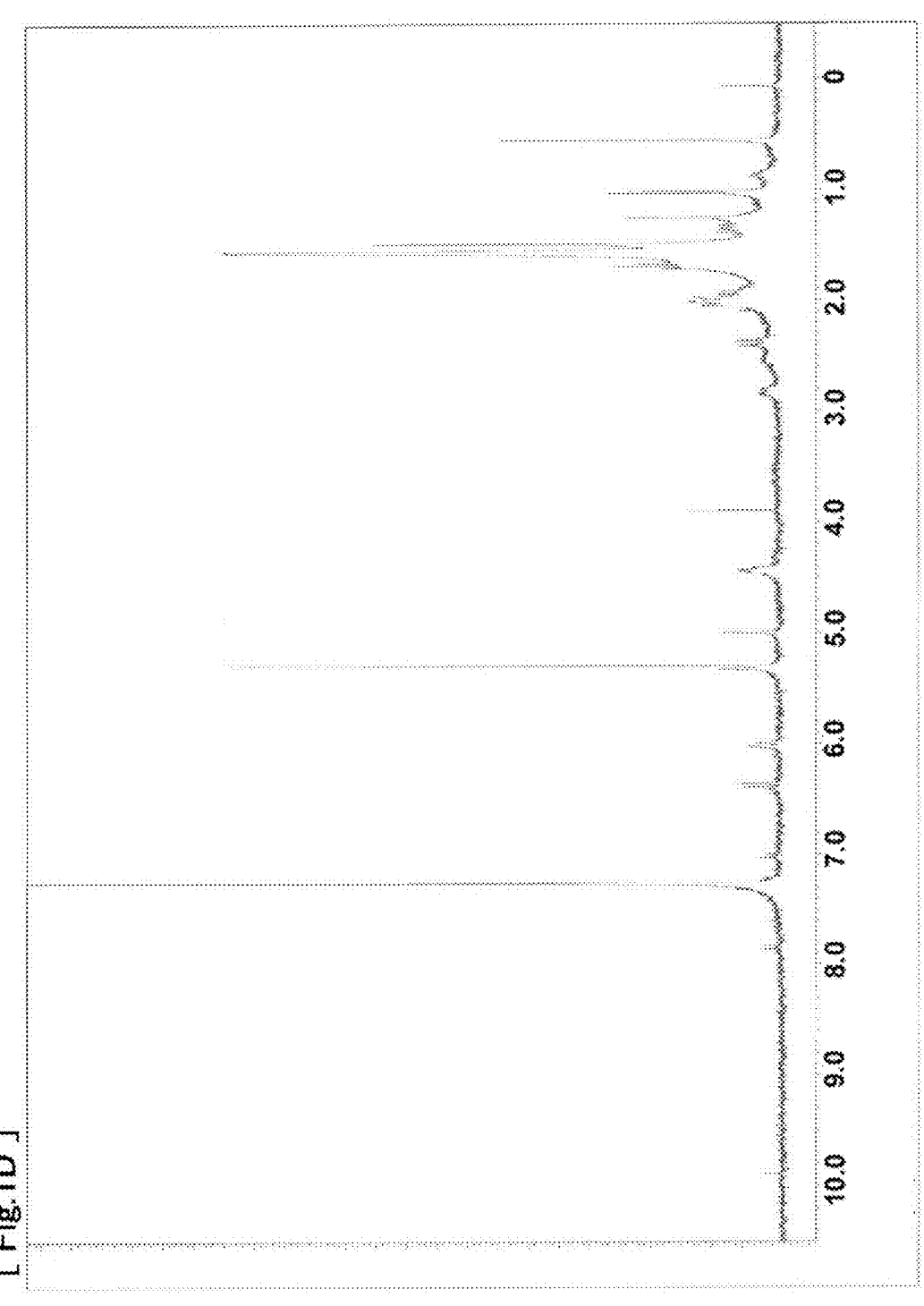

[ Fig.1E ]
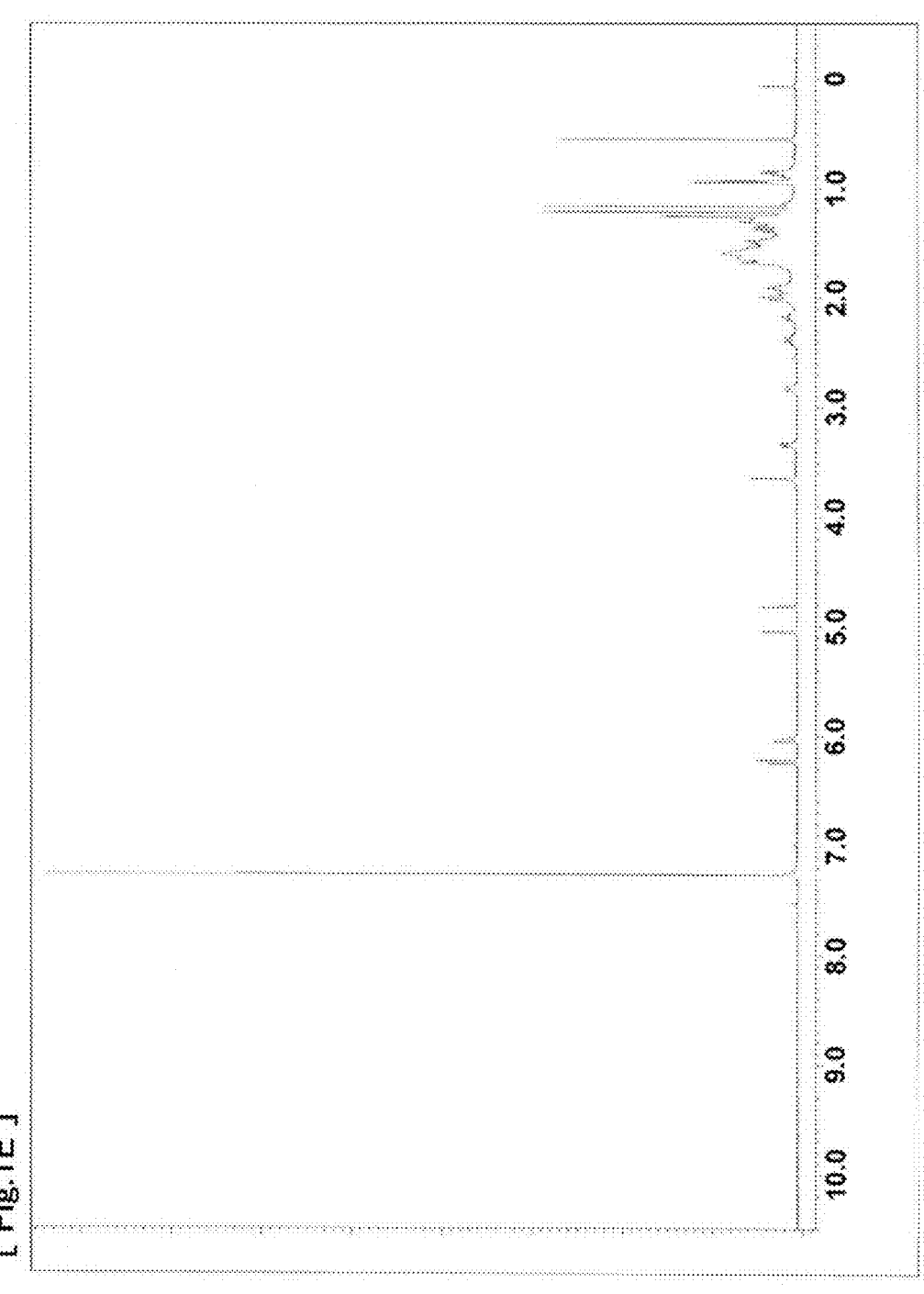

[ Fig.1F ]
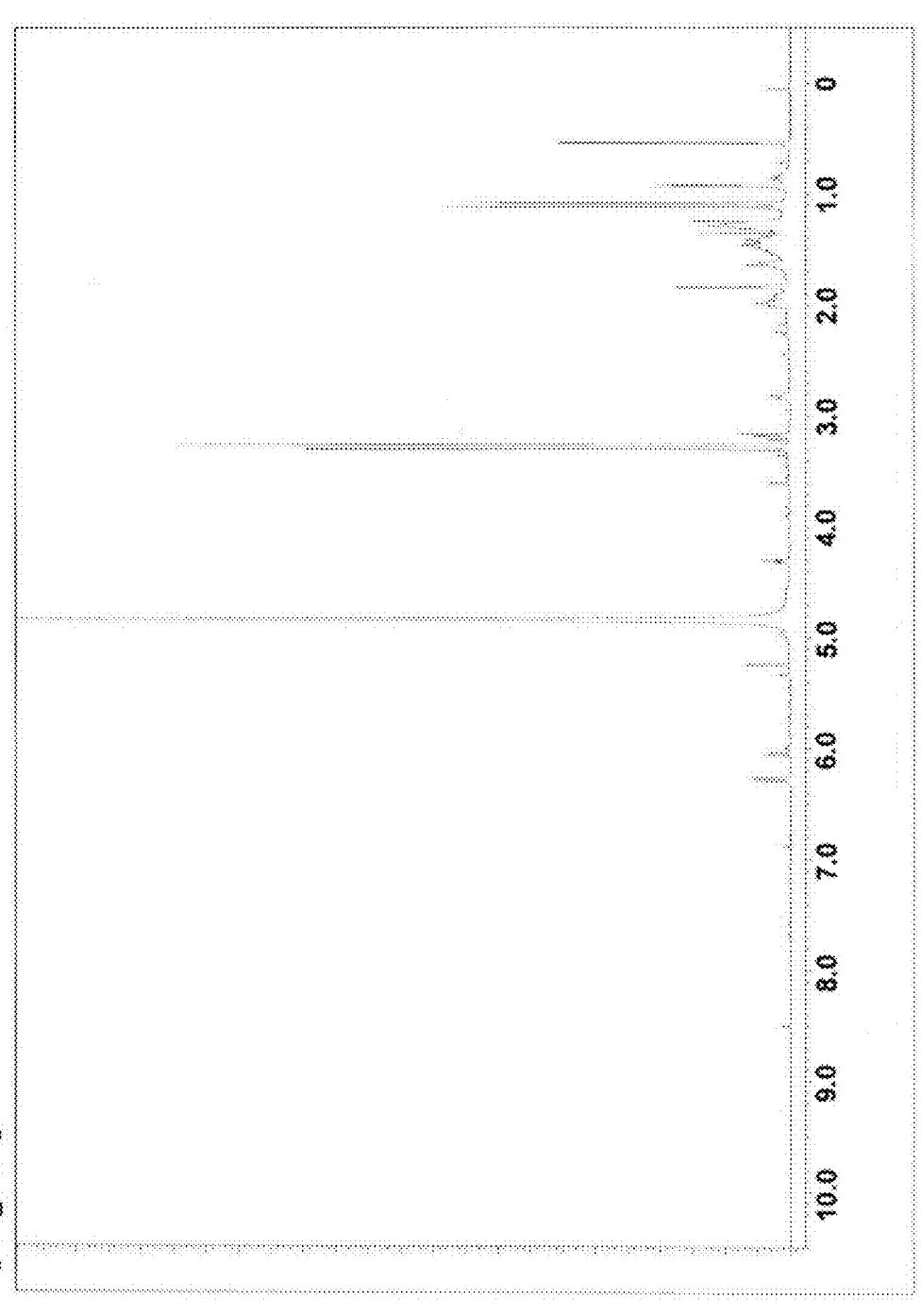

[ Fig.1G ]
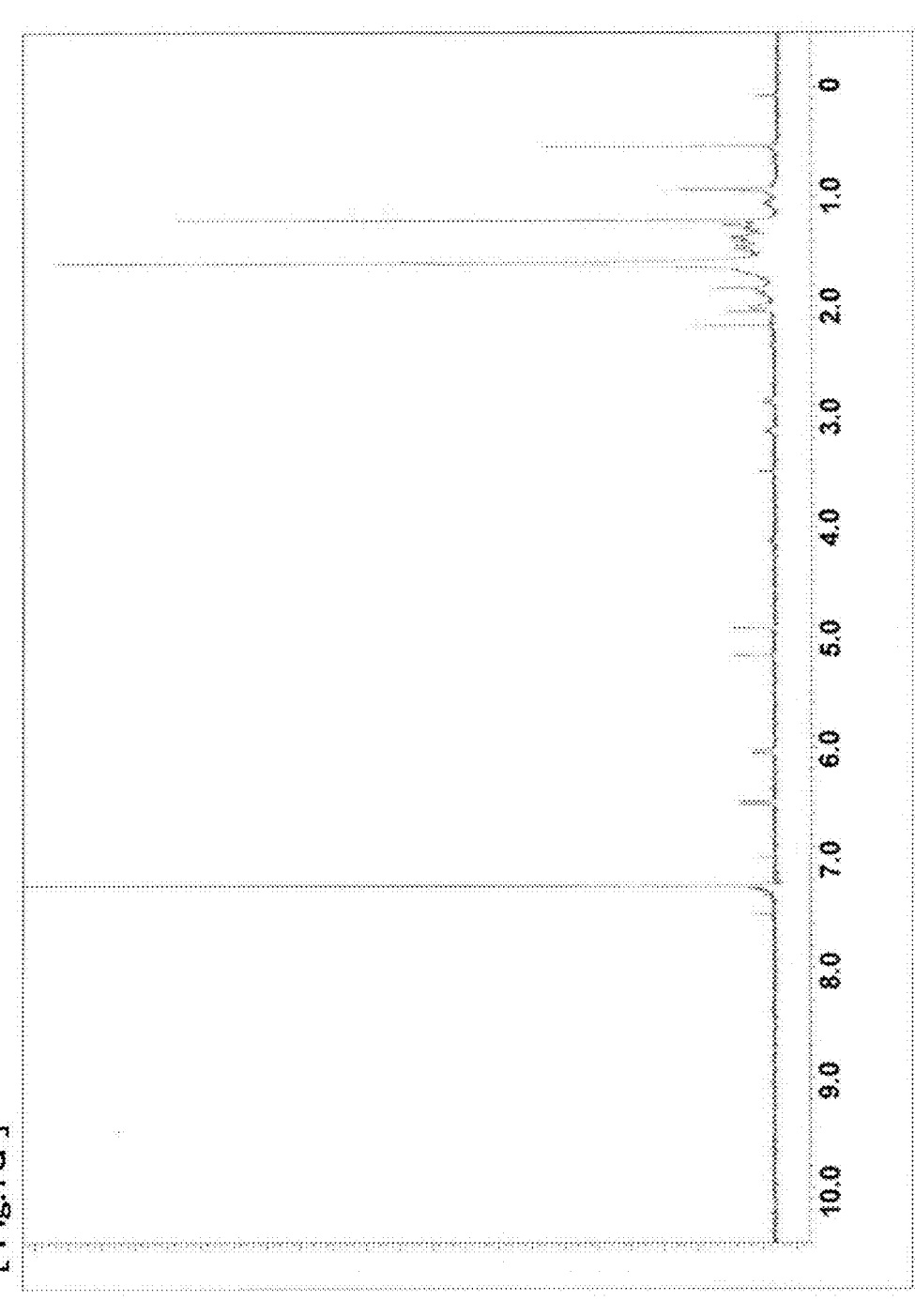

[ Fig.1H ]
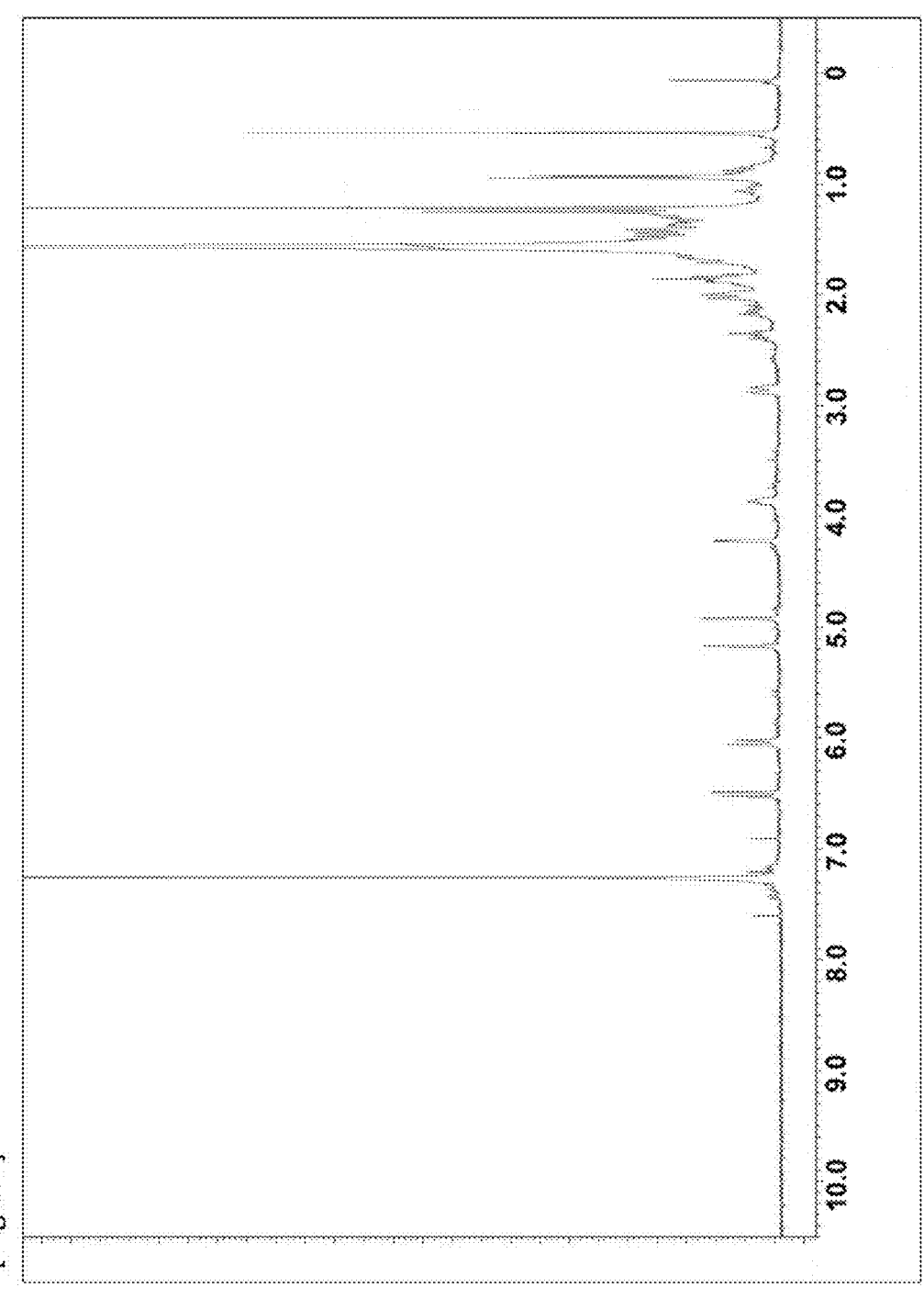

[ Fig. 2A ]
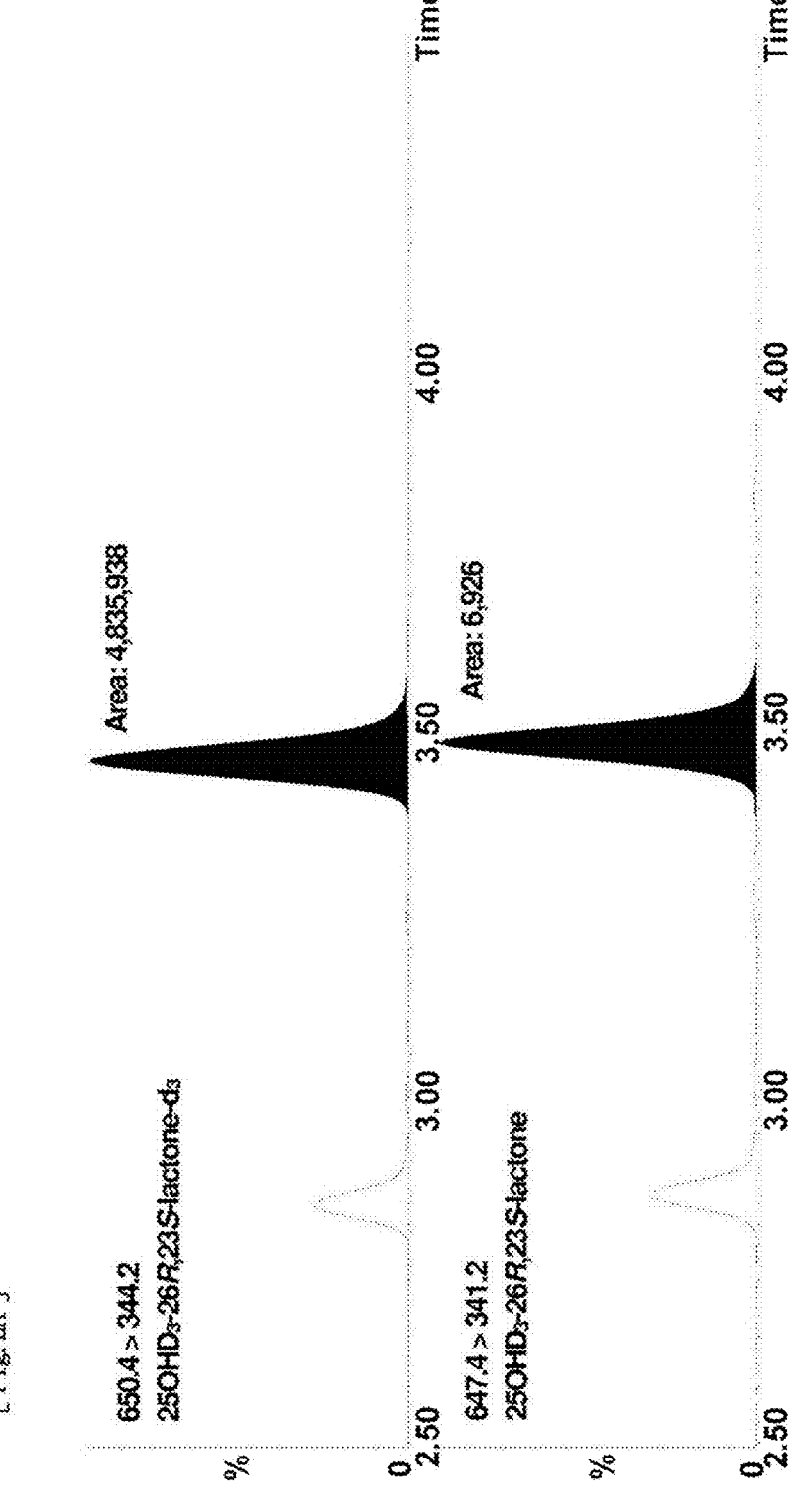

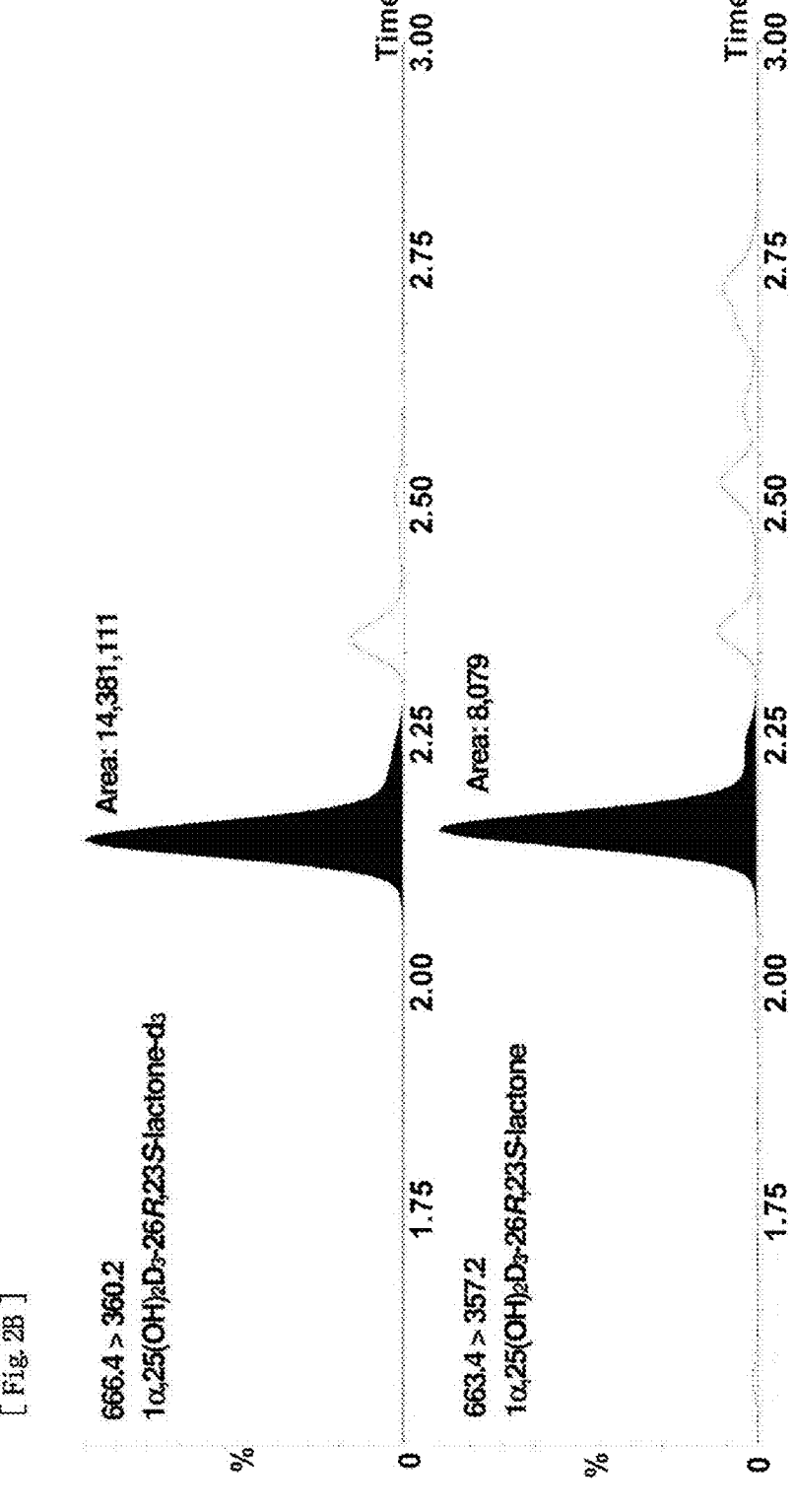
[ Fig. 2B ]

[Fig. 2C]
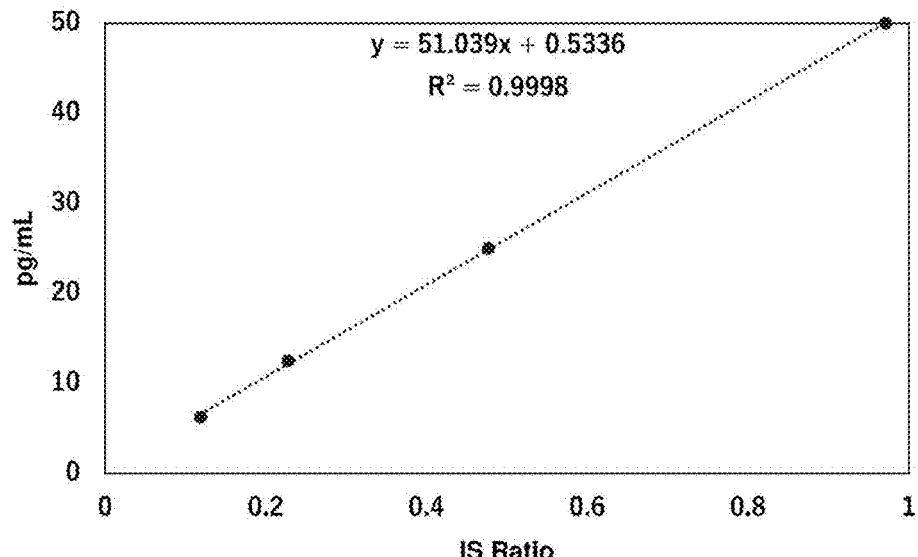
[Fig. 2D]
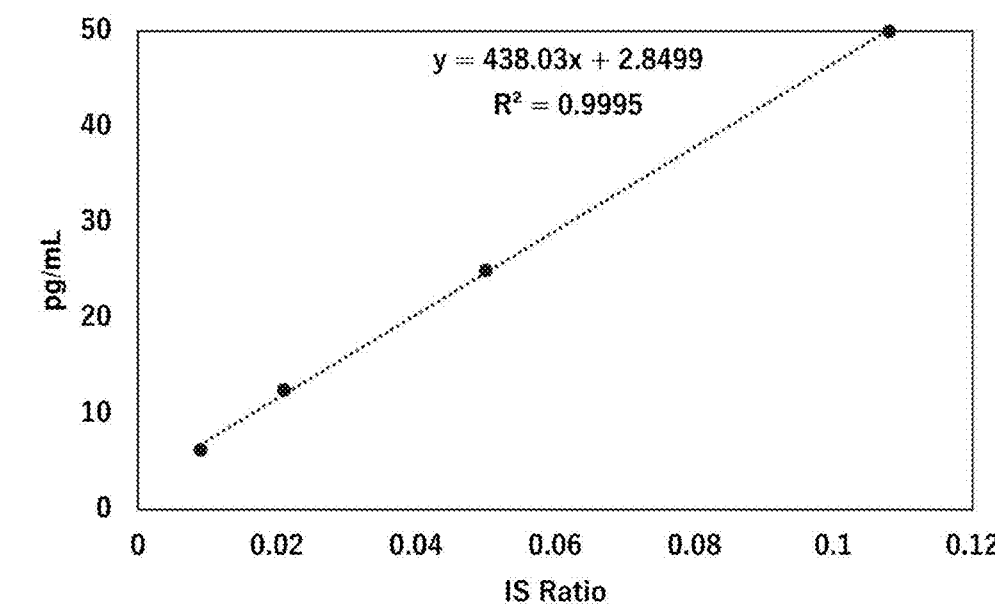

[Fig. 2E]
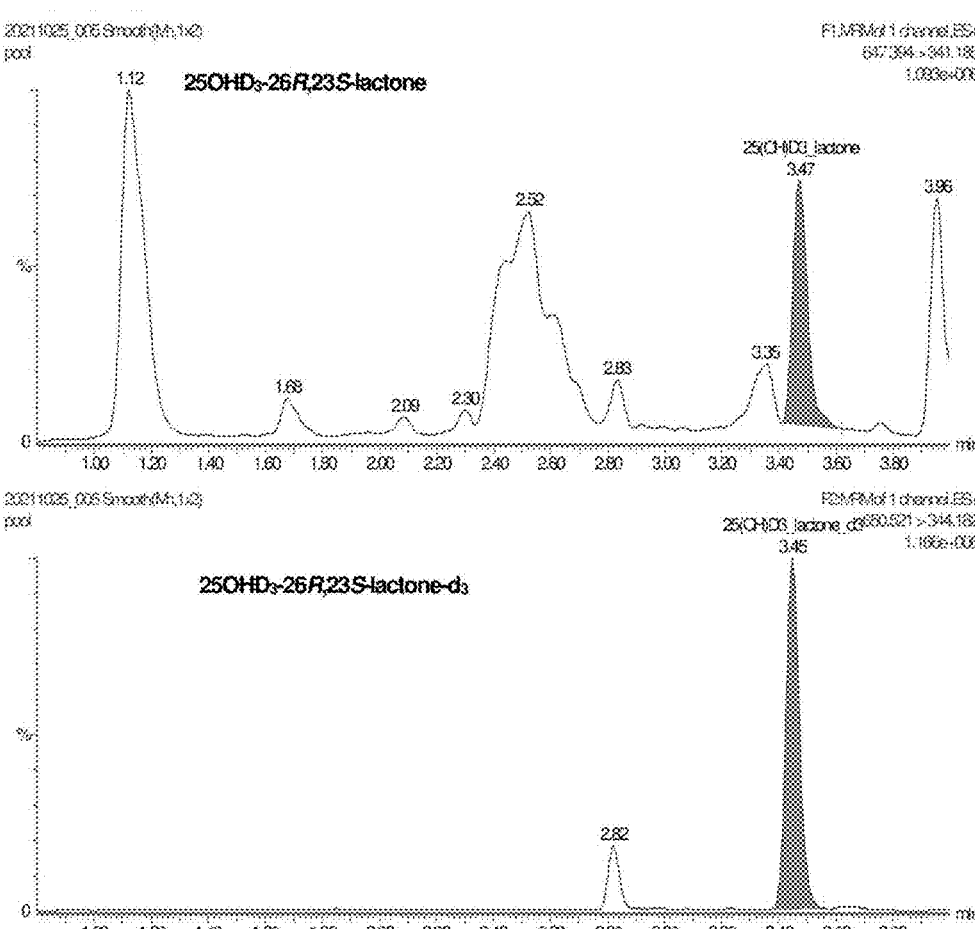

[Fig. 2F]
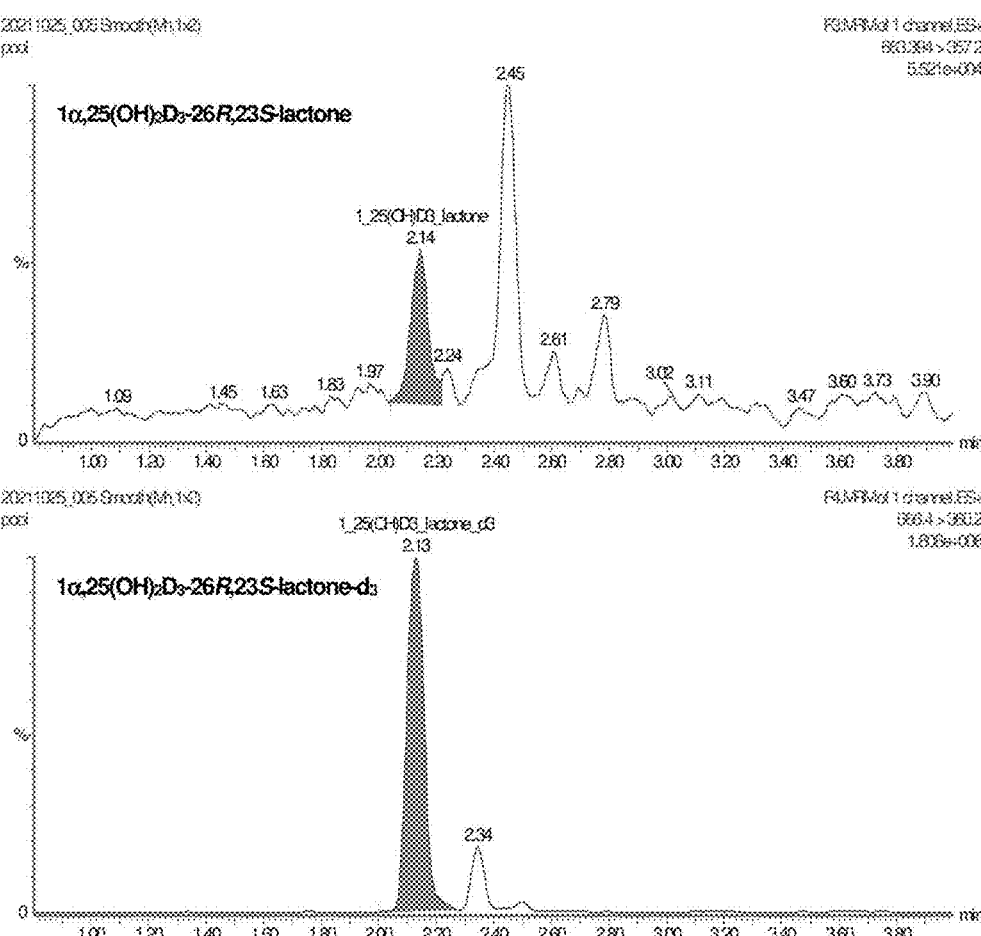

[Fig. 2G]

DAP-PA

R= H: 25OHD₃-26R,23S-lactone
R= OH: 1α,25(OH)₂D₃-26R,23S-lactone

[Fig. 2H]

DAP-PA

R, R'= H: 25OHD₃
R= OH, R'= H: 24R,25(OH)₂D₃
R= H, R'= OH: 4β, 25(OH)₂D₃

[Fig. 3A]
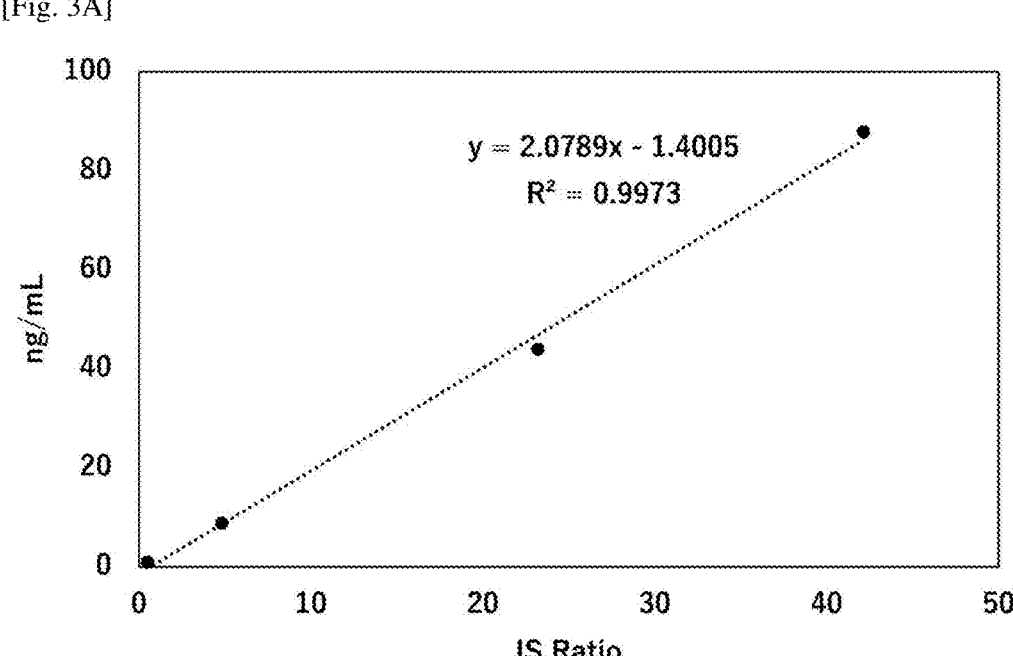
[Fig. 3B]
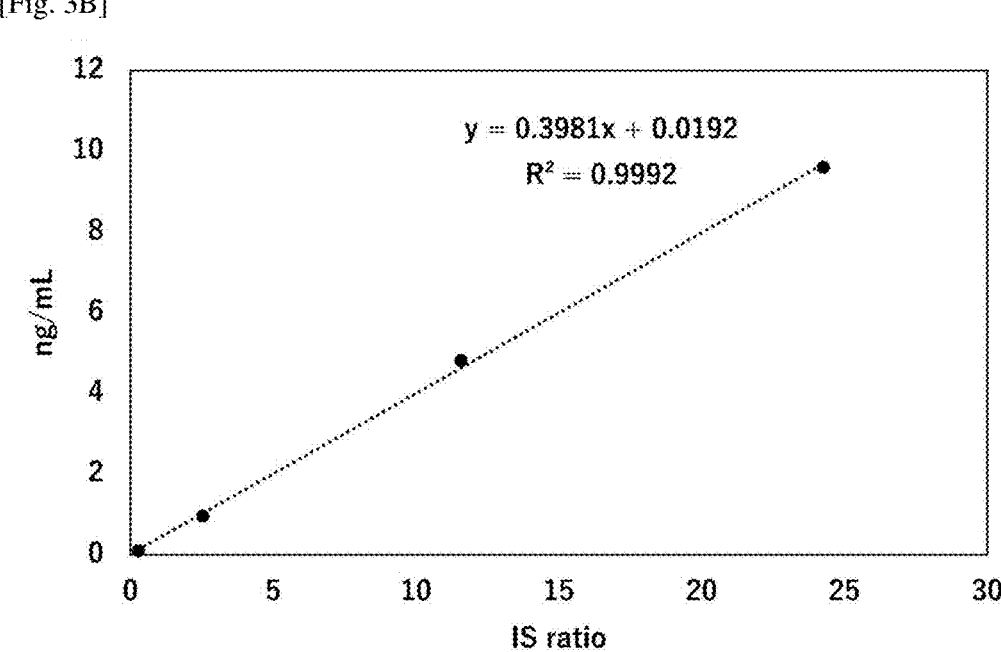

[Fig. 3C]
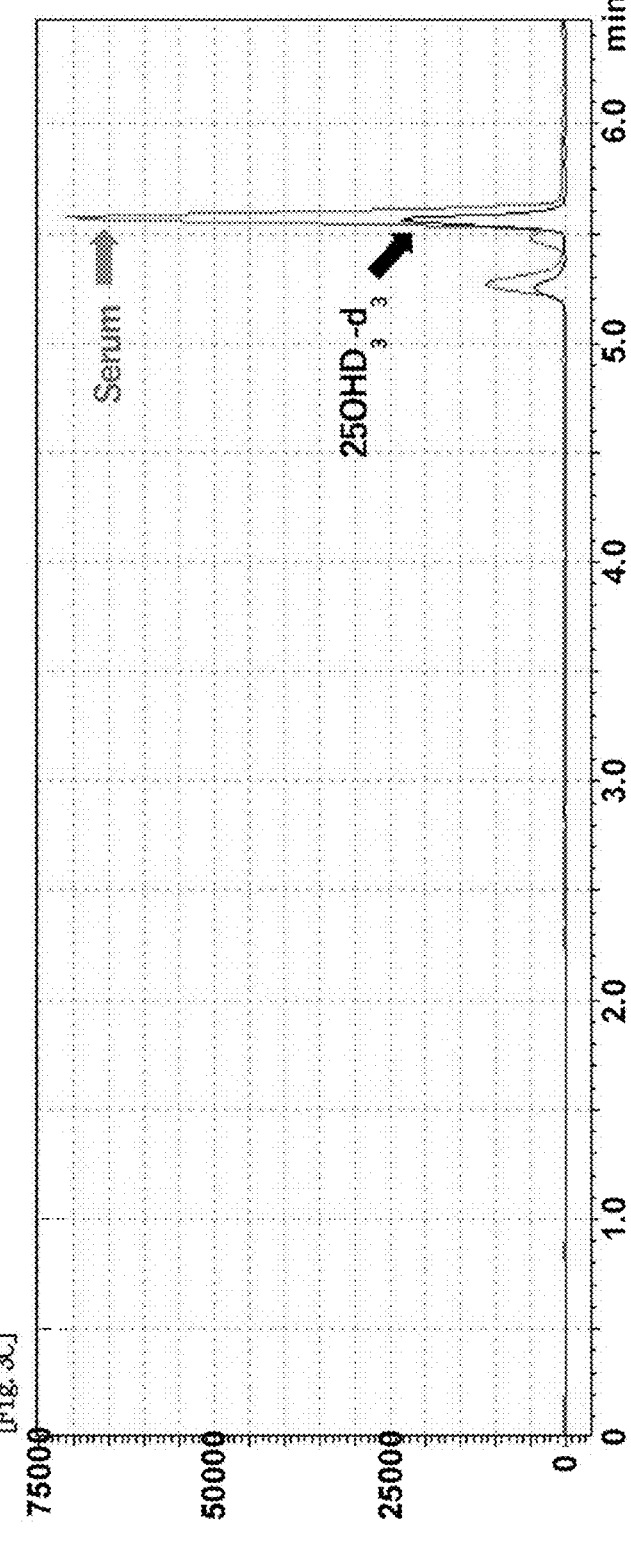

[ Fig. 3D ]
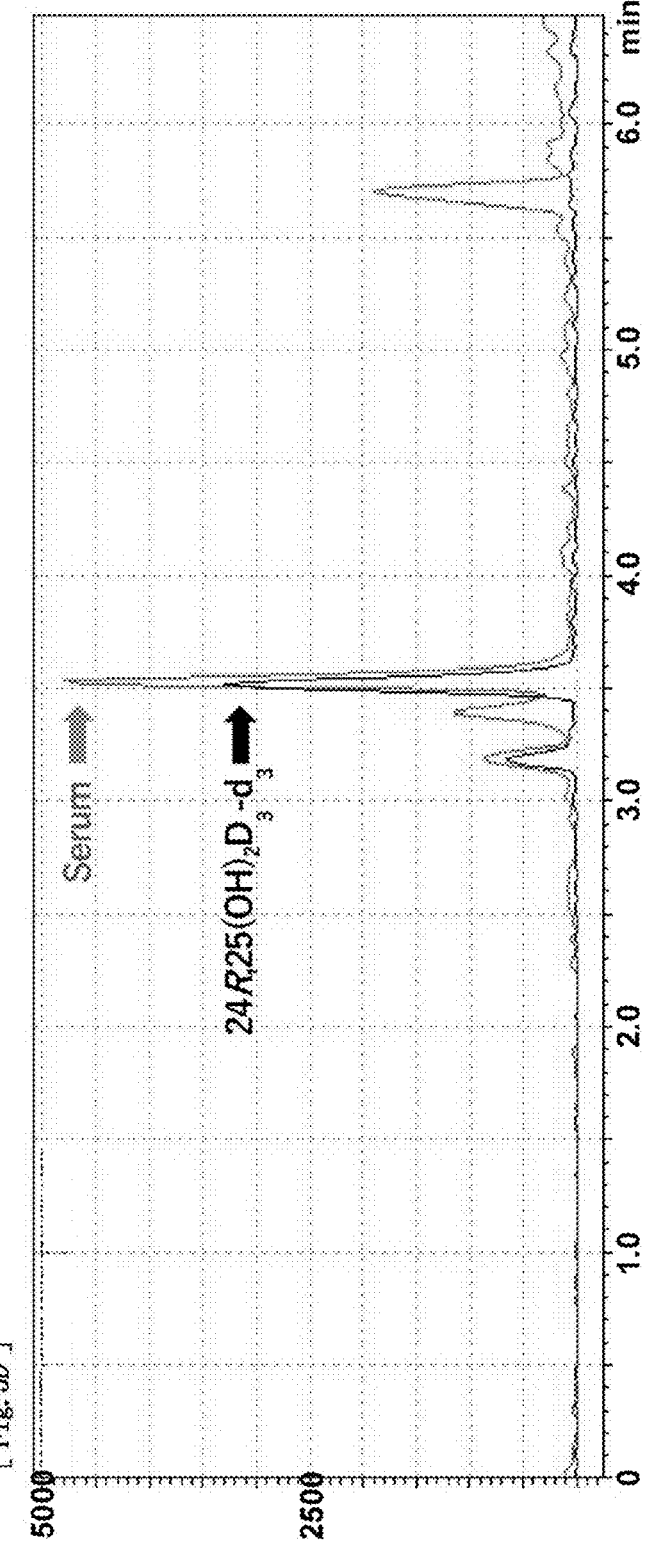

[Fig. 4A]
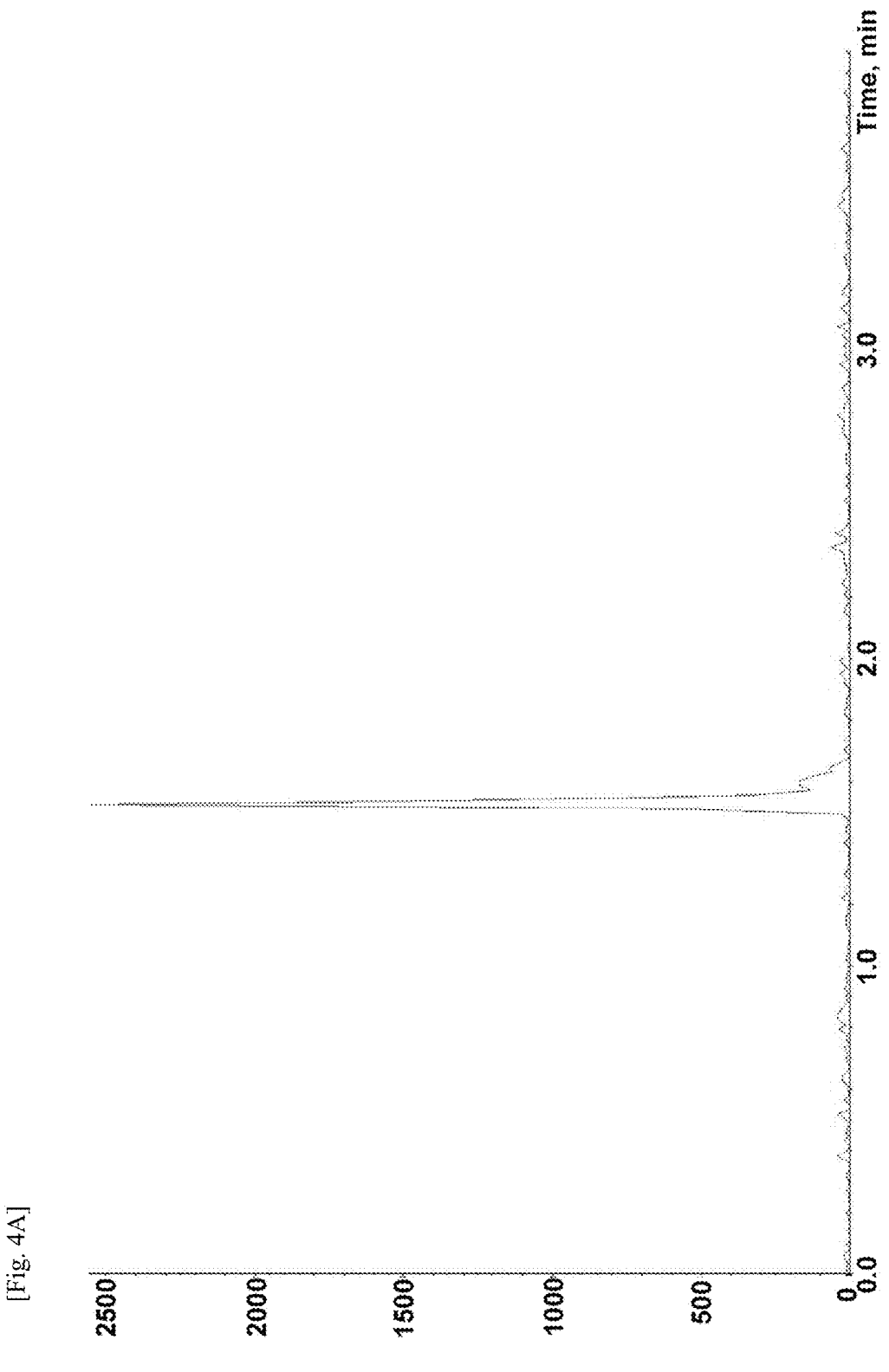

[Fig. 4B]
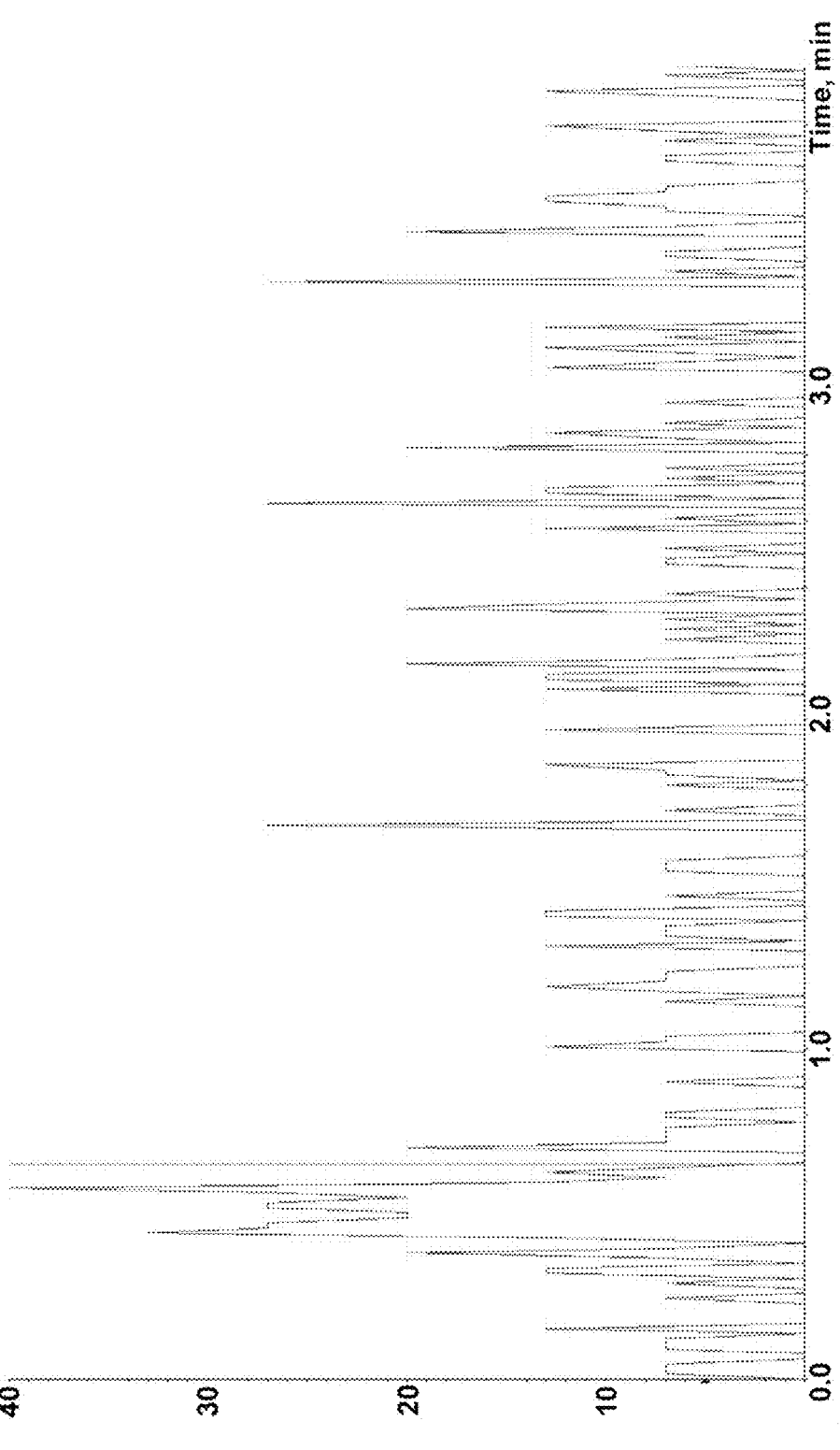

[Fig. 5A]
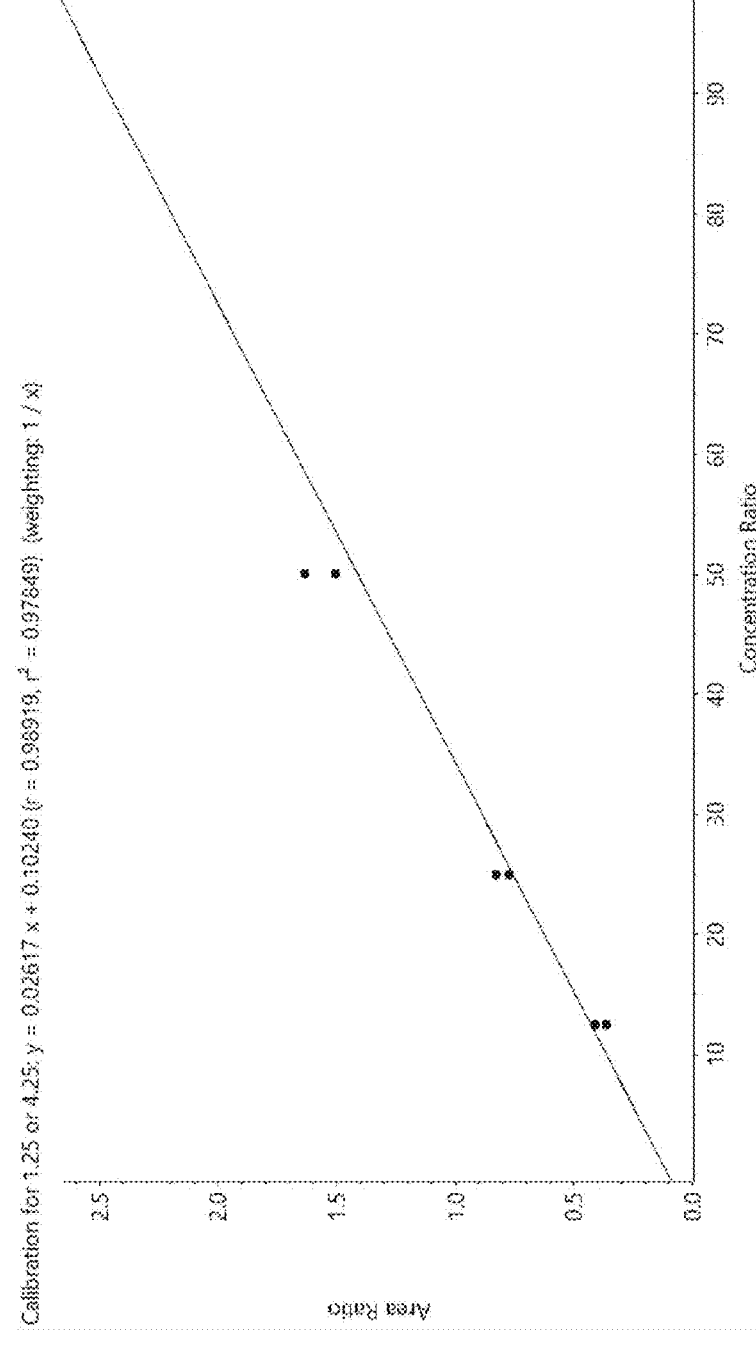
Calibration for 1.25 or 4.25; y = 0.02617 x + 0.10240 (r = 0.98919, r² = 0.97849) (weighting: 1 / x)

[Fig. 5B]
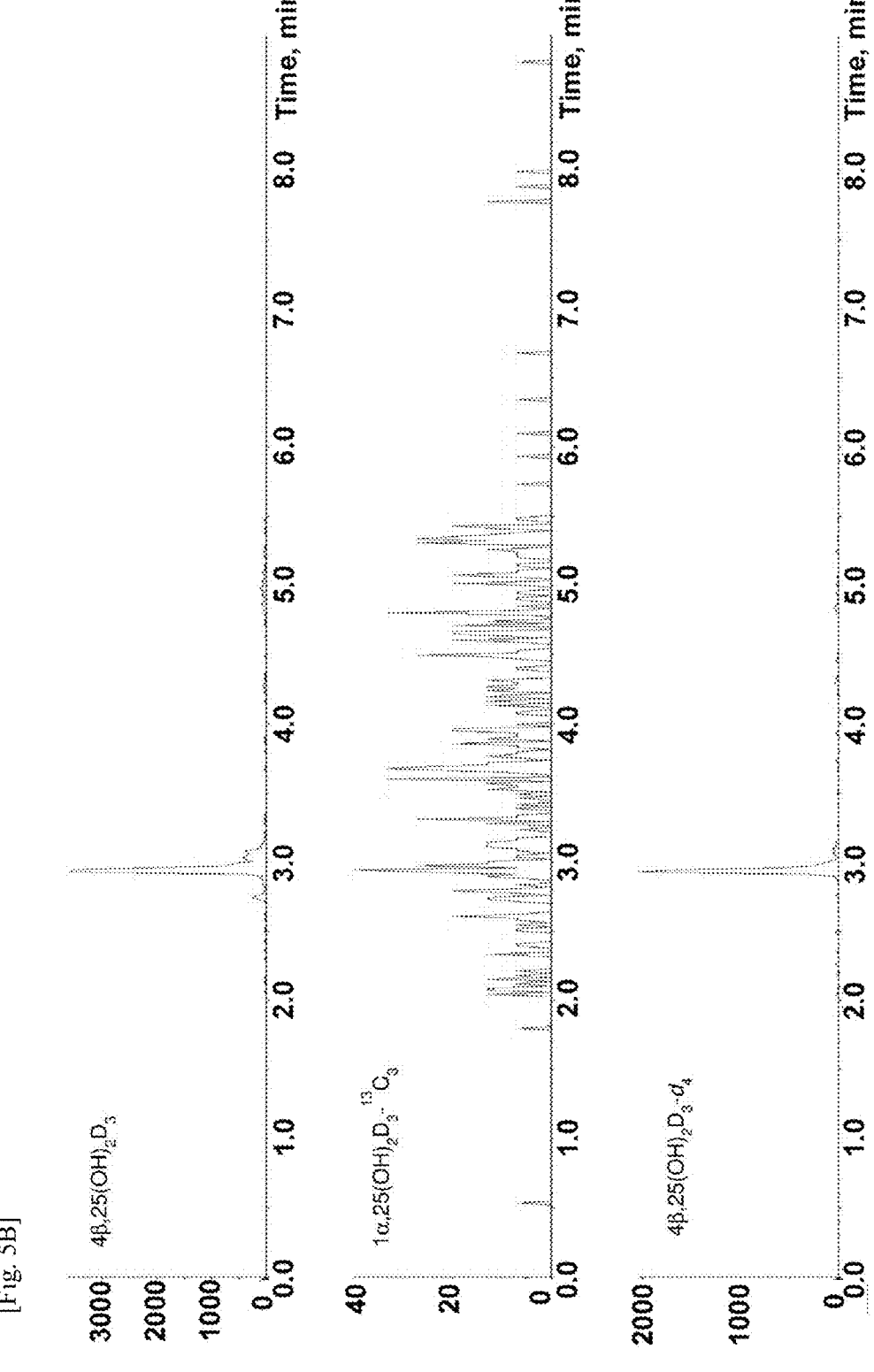

[Fig. 5C]
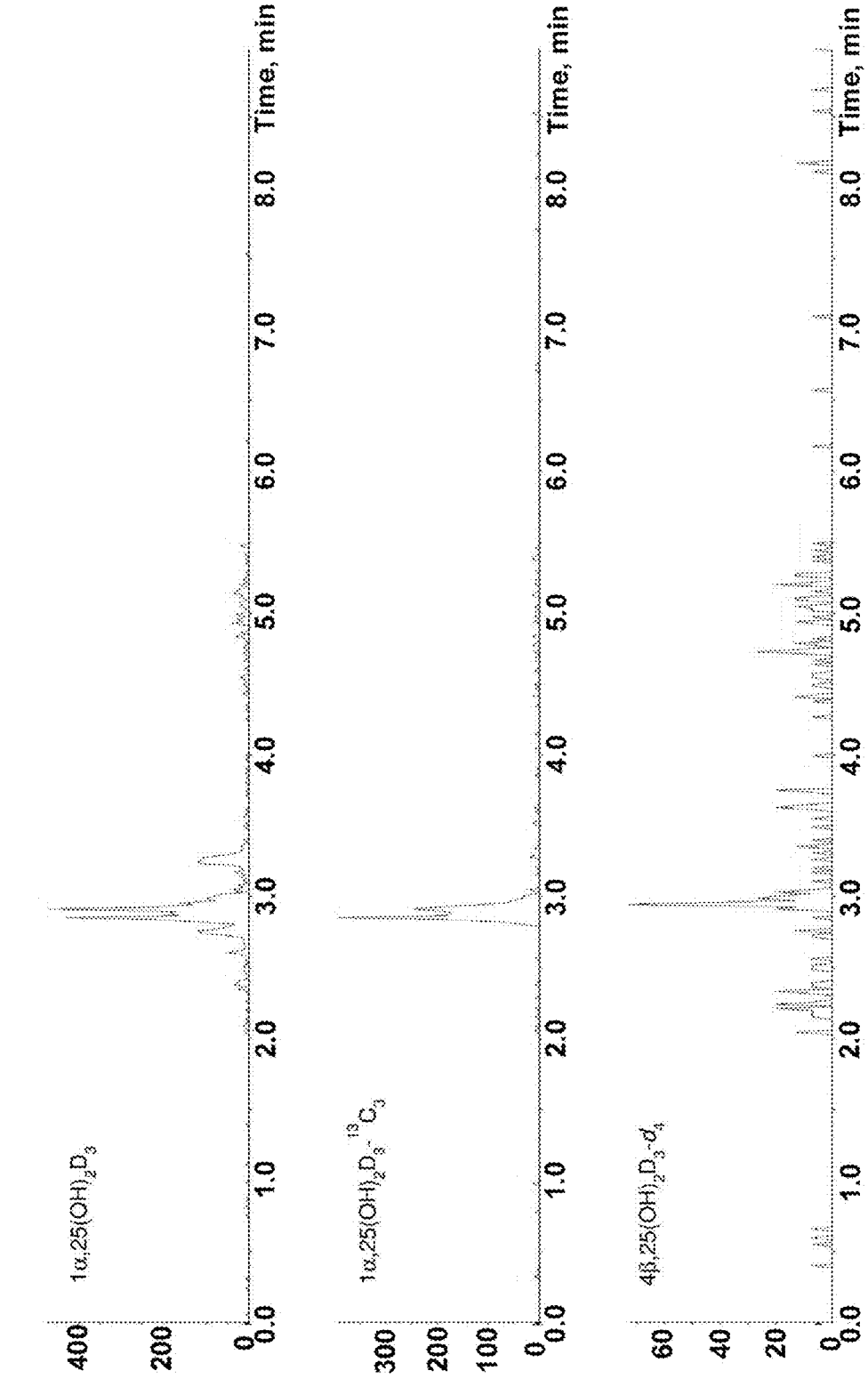

1-hydroxy vitamin D 2-hydroxy vitamin D
or
4-hydroxy vitamin D

[Fig. 8]

1α,25-dihydroxy vitamin $D_3$

4β,25-dihydroxy vitamin $D_3$

[ Fig.9A ]
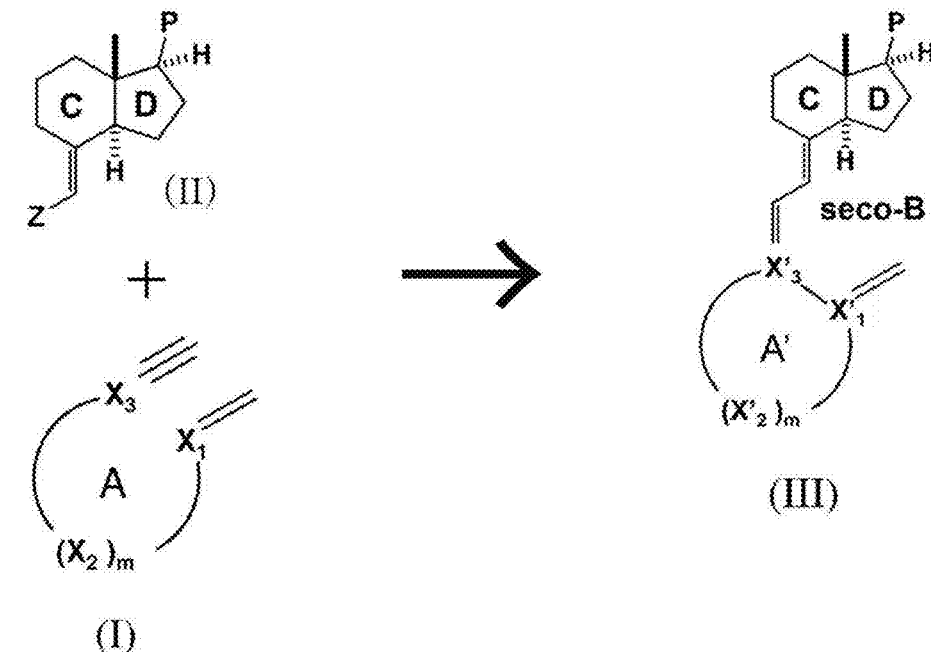
[ Fig.9B ]
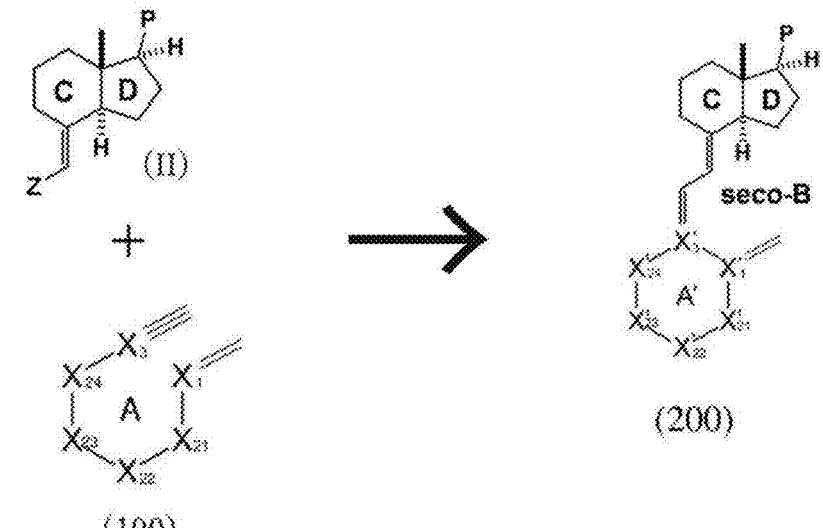

[ Fig.10 ]

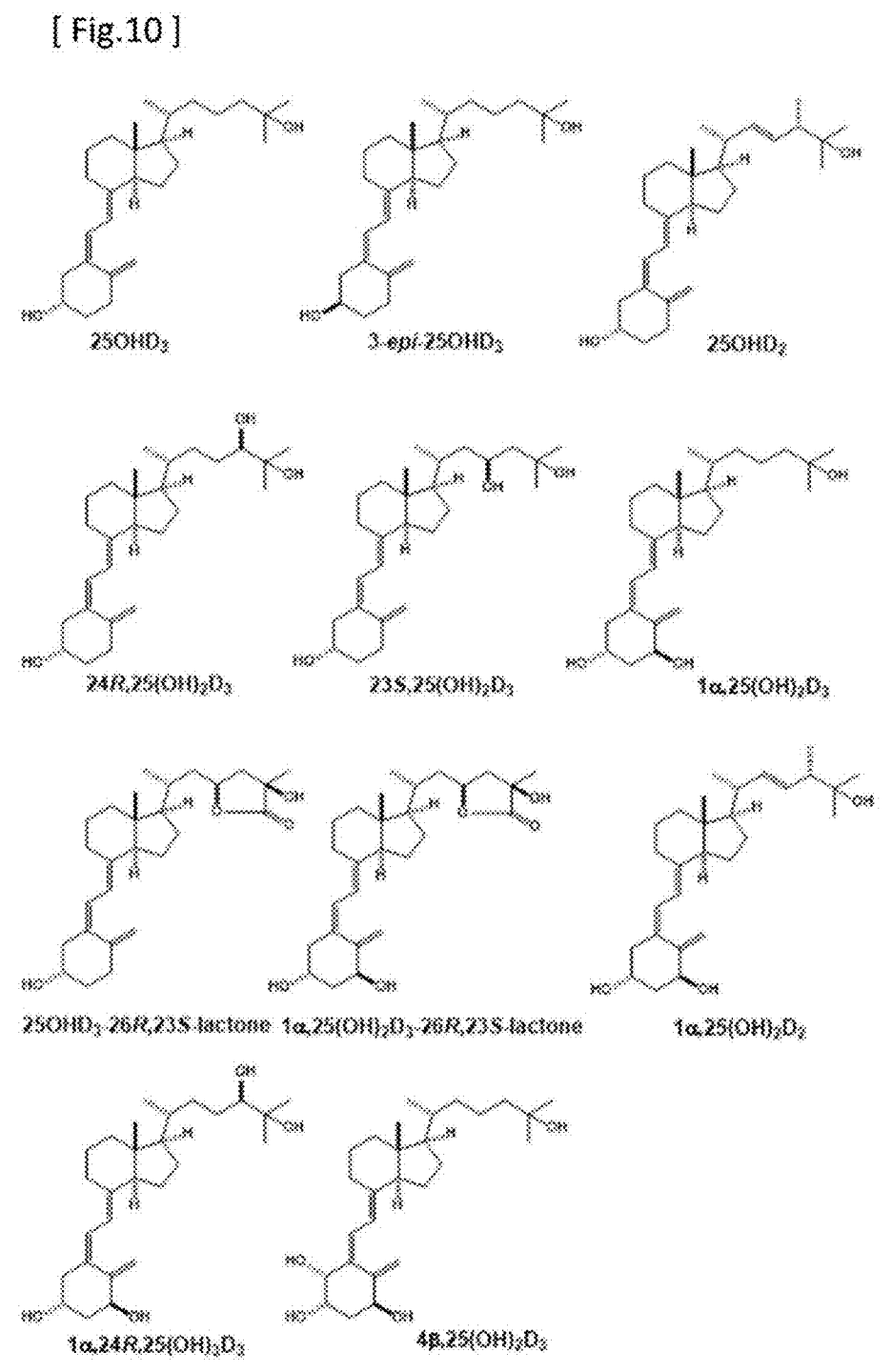

25OHD$_3$     3-epi-25OHD$_3$     25OHD$_2$ 24R,25(OH)$_2$D$_3$     23S,25(OH)$_2$D$_3$     1α,25(OH)$_2$D$_3$ 25OHD$_3$-26R,23S-lactone     1α,25(OH)$_2$D$_3$-26R,23S-lactone     1α,25(OH)$_2$D$_2$

1α,24R,25(OH)$_3$D$_3$     4β,25(OH)$_2$D$_3$

[Fig. 11]
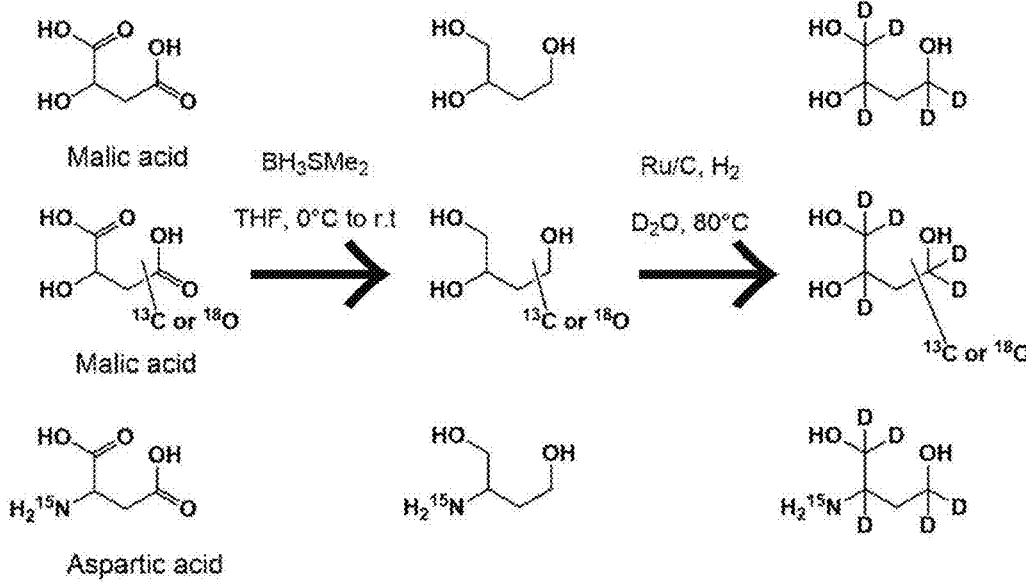

ALKYNE COMPOUND, VITAMIN D COMPOUND, ANALYTICAL METHOD, AND PRODUCTION METHOD

CROSS-REFERENCE TO RELATED APPLICATION

This application claims priority to Japanese Patent Application No. 2021-211040 filed Dec. 24, 2021, the disclosure of which is hereby incorporated by reference in its entirety.

BACKGROUND OF THE INVENTION

Field of the Invention

The present invention relates to an alkyne compound and a vitamin D compound. The present invention also relates to an analytical method using the vitamin D compound and a method for producing the vitamin D compound.

Description of Related Art

Detection and quantification of vitamin D compounds in the living body are highly demanded in the clinical field and the food nutrition field. For example, vitamin D metabolites have been detected and quantified in a biological sample such as blood, urine, body fluid, and spinal fluid. Some techniques for analyzing vitamin D compounds have been disclosed.

For example, Non-Patent Document 1 discloses syntheses of deuterated analogs of 25-hydroxyvitamin D3 and 1α,25-dihydroxyvitamin D3. Non-Patent Document 2 discloses differential diagnosis of vitamin D-related hypercalcemia using serum vitamin D metabolite profiling.

CITATION LIST

Non-Patent Document

[Non-Patent Document 1] Rahul Ray et al., Synthesis of 25-hydroxy-[6,19,19'-2H3vitamin D3 and 1α,25-dihydroxy-[6,19'-2H3] vitamin D3, Steroids, 1992, 57, 142-146.
[Non-Patent Document 2] Martin Kaufmann et al., Differential diagnosis of vitamin D-related hypercalcemia using serum vitamin D metabolite profiling, J. Bone Miner. Res., 2021, 36, 1340-1350.
[Non-Patent Document 3] Aileen Mendoza et al., Controlled lipid β-oxidation and carnitine biosynthesis by a vitamin D metabolite, Cell Chem. Biol., 28, Published: Sep. 9, 2021.
[Non-Patent Document 4] Masahiko Seki et al., A novel caged Cookson-type reagent toward a practical vitamin D derivatization method for mass spectrometric analyses, Rapid Commun. Mass Spectrom., 2020, 34, e8648.

SUMMARY OF THE INVENTION

Technical Problem

The present invention is intended to provide a compound useful for analyzing vitamin D compounds.

Solution to Problem

The inventors of the present invention have found that a specific vitamin D compound labeled with stable isotopes is useful for analyzing vitamin D metabolites. The inventors of the present invention have further found that the vitamin D compound can be produced from a specific alkyne compound.

The present invention provides the following aspects.

[1] An alkyne compound represented by Formula (I) below:

[Chemical Formula 1]

(I)

[in Formula (I),
A is a linear carbon chain having an alkynyl group at an end and having a vinyl group at another end,
$X_1$ is CH or $^{13}CH$,
$X_2$ is CHY, CDY, $^{13}CHY$, $^{13}CDY$, CO, $^{13}CO$, $C^{18}O$, or $^{13}C^{18}O$,
m is an integer from 1 to 4,
when m is 2 or more, $X_2$s are identical or different,
Y is H, D, $NH_2$, $^{15}NH_2$, OH, $^{18}OH$, SH, OR, O(CO)R, $OSO_3H$, $OSO_3Na$, or a sugar substituent, when Formula (I) contains two or more Ys, Ys are identical or different,
R is an alcohol protective group, an alkyl group, an alkenyl group, or an aryl group,
$X_3$ is C or $^{13}C$, and
at least one selected from the group consisting of $X_1$, $X_2$(s), and $X_3$ is modified with a stable isotope D, $^{13}C$, $^{18}O$, or $^{15}N$].

[2] The alkyne compound according to the aspect [1], in which in Formula (I), m is 4, and the alkyne compound is represented by Formula (100):

[Chemical Formula 2]

(100)

[in Formula (100),
A is a linear carbon chain having an alkynyl group at an end and having a vinyl group at another end,
$X_1$ is CH or $^{13}CH$,
$X_{21}$, $X_{22}$, $X_{23}$, and $X_{24}$ are each independently CHY, CDY, $^{13}CHY$, $^{13}CDY$, CO, $^{13}CO$, $C^{18}O$, or $^{13}C^{18}O$,
Y is H, D, $NH_2$, $^{15}NH_2$, OH, $^{18}OH$, SH, OR, O(CO)R, $OSO_3H$, $OSO_3Na$, or a sugar substituent, when Formula (100) contains two or more Ys, Ys are identical or different, R is an alcohol protective group, an alkyl group, an alkenyl group, or an aryl group, $X_3$ is C or $^{13}C$, and at least one selected from the group consisting of $X_1$, $X_{21}$, $X_{22}$, $X_{23}$, $X_{24}$, and $X_3$ is modified with a stable isotope D, $^{13}C$, $^{18}O$, or $^{15}N$].

[3] The alkyne compound according to the aspect [2], in which in Formula (100), at least one selected from the group consisting of $X_{21}$, $X_{22}$, $X_{23}$, and $X_{24}$ is CHY or CDY.

[4] A vitamin D compound represented by Formula (III) below:

[Chemical Formula 3]

(III)

[in Formula (III),

A' represents a cyclic carbon chain corresponding to an A ring of the vitamin D compound, $X'_1$ is C or $^{13}C$, $X'_2$ is CHY', CDY', $^{13}CHY'$, $^{13}CDY'$, CO, $^{13}CO$, $C^{18}O$, or $^{13}C^{18}O$, m is an integer from 1 to 4, when m is 2 or more, $X'_2$s are identical or different, Y' is H, D, $NH_2$, $^{15}NH_2$, OH, $^{18}OH$, SH, OR', O(CO)R', $OSO_3H$, $OSO_3Na$, or a sugar substituent, when Formula (III) contains two or more Y's, Y's are identical or different, R' is an alkyl group, an alkenyl group, or an aryl group, $X'_3$ is C or $^{13}C$, at least one selected from the group consisting of $X'_1$, $X'_2$(s), and $X'_3$ is modified with a stable isotope D, $^{13}C$, $^{18}O$, or $^{15}N$, P is a $C_1$ to $C_{10}$ alkyl group unsubstituted or substituted with a hydroxy group or a $C_2$ to $C_{10}$ alkenyl group unsubstituted or substituted with a hydroxy group, and the alkyl group or the alkenyl group may have a lactone group substituted with a hydroxy group].

[5] The vitamin D compound according to the aspect [4], in which in Formula (III), m is 4, and the vitamin D compound is represented by Formula (200):

[Chemical Formula 4]

(200)

[in Formula (200),

A' is a cyclic carbon chain corresponding to an A ring of the vitamin D compound, $X'_1$ is C or $^{13}C$, $X'_{21}$, $X'_{22}$, $X'_{23}$, and $X'_{24}$ are each independently CHY', CDY', $^{13}CHY'$, $^{13}CDY'$, CO, $^{13}CO$, $C^{18}O$, or $^{13}C^{18}O$, Y' is H, D, $NH_2$, $^{15}NH_2$, OH, $^{18}OH$, SH, OR', O(CO)R', $OSO_3H$, $OSO_3Na$, or a sugar substituent, when Formula (200) contains two or more Y's, Y's are identical or different, R' is an alkyl group, an alkenyl group, or an aryl group, $X'_3$ is C or $^{13}C$, at least one selected from the group consisting of $X'_1$, $X'_{21}$, $X'_{22}$, $X'_{23}$, $X'_{24}$, and $X'_3$ is modified with a stable isotope D, $^{13}C$, $^{18}O$, or $^{15}N$, P is a $C_1$ to $C_{10}$ alkyl group unsubstituted or substituted with a hydroxy group or a $C_2$ to $C_{10}$ alkenyl group unsubstituted or substituted with a hydroxy group, and the alkyl group or the alkenyl group may have a lactone group substituted with a hydroxy group].

[6] The vitamin D compound according to the aspect [5], in which in Formula (200), P has a structure:

[Chemical Formula 5]

[in the structure for P,

Q, Q', Q'', Q''', and Q'''' are each independently H, CH$_2$, CH$_3$, C$_2$H$_5$, O, OH, or a sugar substituent].

[7] An analytical method using the vitamin D compound according to the aspect [4].

[8] The analytical method according to the aspect [7], in which the analytical method comprises analyzing a sample by mass spectrometry, and
in the analyzing, the vitamin D compound is used as an internal standard.

[9] The analytical method according to the aspect [8], in which the mass spectrometry is LC-MS/MS or LC/MS.

[10] The analytical method according to the aspect [7], in which in the analyzing, a vitamin D compound having no hydroxy group at position 1 of an A ring is analyzed separately from a vitamin D compound having a hydroxy group at position 1 of the A ring.

[11] The analytical method according to the aspect [10], in which the vitamin D compound having no hydroxy group at position 1 of the A ring comprises at least one selected from the group consisting of a 2-hydroxyvitamin D compound and a 4-hydroxyvitamin D compound.

[12] The analytical method according to the aspect [10], in which the vitamin D compound having no hydroxy group at position 1 of the A ring comprises at least one selected from the group consisting of a 4β,25-dihydroxyvitamin D3 compound and a 4-hydroxyvitamin D compound.

[13] A method for producing the vitamin D compound according to the aspect [4].

[14] The production method according to the aspect [13], in which an alkyne compound represented by Formula (I):

[Chemical Formula 6]

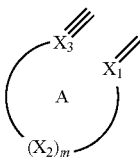

(I)

[in Formula (I),

A is a linear carbon chain having an alkynyl group at an end and having a vinyl group at another end, X$_1$ is CH or $^{13}$CH, X$_2$ is CHY, CDY, $^{13}$CHY, $^{13}$CDY, CO, $^{13}$CO, C$^{18}$O, or $^{13}$C$^{18}$O, m is an integer from 1 to 4, when m is 2 or more, X$_2$s are identical or different, Y is H, D, NH$_2$, $^{15}$NH$_2$, OH, $^{18}$OH, SH, OR, O(CO)R, OSO$_3$H, OSO$_3$Na, or a sugar substituent, when Formula (I) contains two or more Ys, Ys are identical or different, R is an alcohol protective group, an alkyl group, an alkenyl group, or an aryl group, X$_3$ is C or $^{13}$C, and at least one selected from the group consisting of X$_1$, X$_2$(s), and X$_3$ is modified with a stable isotope D, $^{13}$C, $^{18}$O, or $^{15}$N] is used as a material to form the A ring of the vitamin D compound.

Advantageous Effects of Invention

Using the vitamin D compound according to the present invention enables detection and/or quantification of vitamin D metabolites. Using the alkyne compound according to the present invention enables production of the vitamin D compound.

The effect of the invention is not limited to that described in this paragraph and may be any of the effect described in the present specification.

BRIEF DESCRIPTION OF THE DRAWINGS

FIG. 1A shows an NMR spectrum.

FIG. 1B shows an NMR spectrum.

FIG. 1C shows an NMR spectrum.

FIG. 1D shows an NMR spectrum.

FIG. 1E shows an NMR spectrum.

FIG. 1F shows an NMR spectrum.

FIG. 1G shows an NMR spectrum.

FIG. 1H shows an NMR spectrum.

FIG. 2A shows SRM chromatograms of standard 25OHD$_3$-26R,23S-lactone-d$_3$.

FIG. 2B shows SRM chromatograms of standard 1α,25(OH)$_2$D$_3$-26R,23S-lactone-d$_3$.

FIG. 2C shows a calibration curve of standard 25OHD$_3$-26R,23S-lactone.

FIG. 2D shows a calibration curve of standard 1α,25(OH)$_2$D$_3$-26R,23S-lactone.

FIG. 2E shows SRM chromatograms of 25OHD$_3$-26R,23S-lactone in a pooled serum.

FIG. 2F shows SRM chromatograms of 1α,25(OH)$_2$D$_3$-26R,23S-lactone in a pooled serum.

FIG. 2G shows a reaction scheme of derivatization.

FIG. 2H shows a reaction scheme of derivatization.

FIG. 3A shows a calibration curve of standard 25OHD$_3$.

FIG. 3B shows a calibration curve of standard 24R,25(OH)$_2$D$_3$.

FIG. 3C shows an SRM chromatogram of 25OHD$_3$ in a pooled serum.

FIG. 3D shows an SRM chromatogram of 24R,25(OH)$_2$D$_3$ in a pooled serum.

FIG. 4A shows an SRM chromatogram of a non-adsorbed fraction of an antibody column.

FIG. 4B shows an SRM chromatogram of an adsorbed fraction of an antibody column.

FIG. 5A shows a calibration curve of standard 4β,25-(OH)$_2$D$_3$.

FIG. 5B shows SRM chromatograms of a non-adsorbed fraction of an antibody column of a pooled serum.

FIG. 5C shows SRM chromatograms of an adsorbed fraction of an antibody column of a pooled serum.

FIG. 6 is a view showing derivatization of vitamin D compounds and fragmentation of derivatives.

FIG. 7 shows chemical structures of a vitamin D compound having a hydroxy group at position 1 of the A ring and a vitamin D compound having no hydroxy group at position 1 of the A ring.

FIG. 8 shows chemical structures of 1α,25-dihydroxyvitamin D$_3$ and 4β,25-dihydroxyvitamin D$_3$.

FIG. 9A shows an example reaction scheme for producing of the vitamin D compound of the present invention.

FIG. 9B shows an example reaction scheme for producing the vitamin D compound of the present invention.

FIG. 10 shows example vitamin D compounds.

FIG. 11 shows example compounds used to produce the alkyne compounds of the present invention.

DESCRIPTION OF THE INVENTION

Embodiments of the present invention will be described below. However, the present invention is not limited to the following embodiments, which can be arbitrarily changed within the scope of the invention.

1. Description of the Present Invention

Various vitamin D metabolites have been found. For example, one of the most important vitamin D metabolites in terms of physiological activity is $1\alpha,25(OH)_2D_3$, which is also referred to as active vitamin D. Another example of the vitamin D metabolites is a vitamin D lactone, which is reported to suppress fatty acid metabolism (Non-Patent Document 3). Fine structural changes in the side chain structure of vitamin D metabolites may affect physiological activities of the vitamin D metabolites. To elucidate various physiological activities of any vitamin D metabolite, accurate quantification of the vitamin D metabolite is required.

At the present time, $1\alpha,25(OH)_2D_3$ is quantified by immunochemical assay. It is, however, difficult to individually detect or quantify other trace vitamin D metabolites by the immunochemical assay. As a method of detecting or quantifying vitamin D metabolites at high sensitivity, an LC-MS/MS using a derivatization reagent is expected to be used (Non-Patent Document 4). Detection or quantification by the LC-MS/MS essentially involves vitamin D metabolites labeled with stable isotopes.

As described in Non-Patent Document 1, a method of deuterium labeling by H-D exchange with heavy water has been known. However, when stored in a solution, a vitamin D compound labeled by the method may undergo H-D exchange for light water in the solvent. In other words, the vitamin D compound deuterium-labeled by H-D exchange has poor storage stability.

A vitamin D compound has an A ring, a seco-B ring, a C ring, and a D ring (in the description, the C ring and the D ring are also collectively referred to as a "CD ring"). The CD ring has different side chains according to the type of vitamin D compound or has structural diversity. The A ring moiety of the vitamin D compound also has structural diversity, which is lower than that of the CD ring side chain.

The present invention provides an alkyne compound labeled with a stable isotope. The alkyne compound is usable as a substance for forming the A ring moiety. A vitamin D compound produced by using the alkyne compound has an A ring moiety labeled with a stable isotope. By using the alkyne compound, a stable isotope is introduced into the A ring moiety, and thus various vitamin D metabolites labeled with stable isotopes can be produced without introducing a stable isotope into a CD ring side chain. As described above, the structural diversity of the A ring moiety of the vitamin D compound is lower than that of the CD ring side chain. In other words, fewer variations of alkyne compounds can be used to produce various vitamin D compounds. Hence, the alkyne compound according to the present invention can be used to efficiently produce various vitamin D compounds labeled with stable isotopes.

The vitamin D compound according to the present invention is produced from the alkyne compound according to the present invention as a material to form the A ring. The vitamin D compound is not necessarily a compound labeled by H-D exchange with heavy water and accordingly has excellent storage stability.

The vitamin D compound according to the present invention is usable in various analytical methods and is usable specifically in mass spectrometry, more specifically in isotope dilution mass spectrometry. In other words, the present invention also provides an analytical method using the vitamin D compound. In an embodiment, the present invention provides an analytical method comprising detecting or quantifying a vitamin D metabolite. The detecting or quantifying may be carried out with a mass spectrometer, especially with a liquid chromatography mass spectrometer, and more especially by LC-MS/MS. The vitamin D compound according to the present invention is usable regardless of a manufacturer of a mass spectrometer manufacturer.

The vitamin D compound according to the present invention is usable, for example, in the field of clinical test or food inspection. In the field of clinical test or food inspection, the measurement of vitamin D metabolites is highly demanded. The present invention should enable efficient production of compounds labeled with stable isotopes for not only currently known vitamin D metabolites but also vitamin D metabolites that may be found in the future. Hence, the present invention also contributes to speedy creation of measurement environment for various vitamin D metabolites.

The present invention will next be described in further detail.

2. First Embodiment (Alkyne Compound)

The present invention provides an alkyne compound represented by Formula (I) below. The alkyne compound is labeled with a stable isotope as described below. The alkyne compound is usable to produce various vitamin D compounds, and more specifically, the alkyne compound may be used as a compound for forming an A ring moiety of various vitamin D compounds. The alkyne compound is labeled with a stable isotope, and thus various vitamin D compounds labeled with a stable isotope can be produced using the alkyne compound. Vitamin D compounds produced using the alkyne compound have excellent storage stability.

2-1. Structure of Alkyne Compound of Formula (I)

Hereinafter, the alkyne compound of Formula (I) will be described.

[Chemical Formula 7]

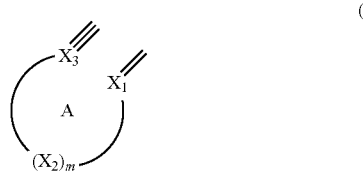

(I)

In Formula (I), A is a linear carbon chain having an alkynyl group at an end and having a vinyl group at another end. In other words, the alkyne compound is a compound having an enyne structure. Hence, the present invention is also said to provide an enyne compound represented by Formula (I).

A is a letter that is attached merely for convenience to explain about a moiety in the vitamin D compound described later and does not represent any substance such as an element constituting the alkyne compound of Formula (I).

In Formula (I), $X_1$ may be CH or $^{13}CH$. In other words, $X_1$ constitutes the alkene moiety of the enyne structure.

When $X_1$ is CH, at least one selected from the group consisting of $X_2(s)$ and $X_3$ is modified with a stable isotope D, $^{13}C$, $^{18}O$, or $^{15}N$.

When $X_1$ is $^{13}$CH, neither $X_2$(s) nor $X_3$ may be modified with a stable isotope, or also in this case, at least one selected from the group consisting of $X_2$(s) and $X_3$ may be modified with a stable isotope D, $^{13}$C, $^{18}$O, or $^{15}$N.

In Formula (I), $X_2$ is CHY, CDY, $^{13}$CHY, $^{13}$CDY, CO, $^{13}$CO, C$^{18}$O, or $^{13}$C$^{18}$O. In Formula (I), m represents the number of $X_2$s in the alkyne compound, and m is an integer from 1 to 4. The alkyne compound of Formula (I) has linearly continuing m pieces of $X_2$(s) between $X_1$ and $X_3$.

When m is 2 or more, $X_2$s may be identical or different from each other. In other words, when the alkyne compound has two or more $X_2$s, the two or more pieces of $X_2$s are each independently selected from CHY, CDY, $^{13}$CHY, $^{13}$CDY, CO, $^{13}$CO, C$^{18}$O, and $^{13}$C$^{18}$O.

Preferably, m is 2, 3, or 4, m is more preferably 3 or 4, and m is even more preferably 4. An embodiment in which m is 4 will be further described with reference to Formula (100).

When at least one of $X_2$(s) is modified with a stable isotope D, $^{13}$C, $^{18}$O, or $^{15}$N, neither $X_1$ nor $X_3$ may be modified with a stable isotope, or also in this case, one or both of $X_1$ and $X_3$ may be modified with a stable isotope.

When none of $X_2$(s) are modified with a stable isotope D, $^{13}$C, $^{18}$O, or $^{15}$N, one or both of $X_1$ and $X_3$ are modified with a stable isotope.

In Formula (I), Y is H, D, NH$_2$, $^{15}$NH$_2$, OH, $^{18}$OH, SH, OR, O(CO)R, OSO$_3$H, OSO$_3$Na, or a sugar substituent. When Formula (I) contains two or more Ys, Ys are identical or different. In other words, when the alkyne compound has two or more Ys, the two or more Ys are each independently selected from H, D, NH$_2$, $^{15}$NH$_2$, OH, $^{18}$OH, SH, OR, O(CO)R, OSO$_3$H, OSO$_3$Na, and a sugar substituent.

In Formula (I), R is an alcohol protective group, an alkyl group, an alkenyl group, or an aryl group. When Formula (I) contains two or more Rs, Rs are identical or different. In other words, when the alkyne compound has two or more Rs, the two or more Rs are each independently selected from an alcohol protective group, an alkyl group, an alkenyl group, and an aryl group.

The alcohol protective group as R in the alkyne compound may be, for example, a silyl alcohol protective group or a benzyl alcohol protective group. Examples of the silyl alcohol protective group include, but are not necessarily limited to, t-butyldimethylsilyl (also referred to as TBS or TBDMS), triisopropylsilyl (also referred to as TIPS), and triethylsilyl (also referred to as TES). Examples of the benzyl alcohol protective group include, but are not necessarily limited to, p-methoxybenzyl (also referred to as PMB), benzyloxymethyl (also referred to as BOM), and benzyl (also referred to as Bn). The structures of these exemplified alcohol protective groups are shown in Table 1.

TABLE 1

Examples of alcohol protective group

TBDMS (t-butyldimethylsilyl)

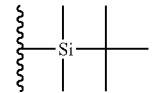

TIPS (triisopropylsilyl)

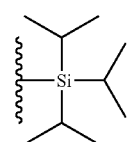

TABLE 1-continued

Examples of alcohol protective group

TES (triethylsilyl)

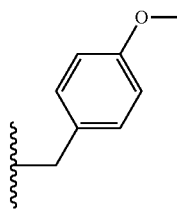

PMB (p-methoxybenzyl)

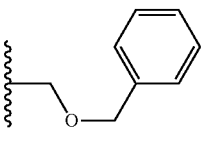 [SMILES: *COCc1ccccc1]

BOM (benzyloxymethyl)

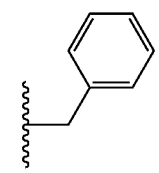 [SMILES: *Cc1ccccc1]

Bn (benzyl)

The alkyl group as R in the alkyne compound may be a substituted or unsubstituted, linear or branched alkyl group having 1 to 10 carbon atoms. The linear or branched alkyl group may, for example, have 1 to 8, 1 to 6, or 1 to 4 carbon atoms. The number of carbon atoms excludes the number of carbon atoms of substituents.

The alkenyl group as R in the alkyne compound may be a linear or branched alkenyl group having 2 to 10 carbon atoms. The linear or branched alkenyl group may, for example, have 2 to 8, 2 to 6, or 2 to 4 carbon atoms. The number of carbon atoms excludes the number of carbon atoms of substituents.

The aryl group as R in the alkyne compound may be a substituted or unsubstituted aryl group having 6 to 20 carbon atoms. The aryl group preferably has 6 to 18 carbon atoms and may, for example, have 6 to 16, 6 to 14, 6 to 12, or 6 to 10 carbon atoms. The number of carbon atoms excludes the number of carbon atoms of substituents. The aryl group may be an unsubstituted aryl group and may be, for example, a phenyl group or a naphthyl group.

In Formula (I), the sugar substituent may, for example, have the following structure.

[Chemical Formula 8]

As for Wo in the sugar substituent represented by the structure, W is a substituent on a ring structure-forming carbon of the sugar, whereas o is the number of the substituents and is an integer from 3 to 5. W may be H, OH, $CH_2OH$, COOH, $NH_2$, or NHAc, and Ws are identical or different. In other words, three to five Ws of the sugar substituent may each independently be selected from H, OH, $CH_2OH$, COOH, $NH_2$, and NHAc.

In an embodiment, at least one of $X_2(s)$ is CHY, CDY, $^{13}$CHY, or $^{13}$CDY, and, for example, each $X_2$ may be CHY, CDY, $^{13}$CHY, or $^{13}$CDY.

In the embodiment, preferably, Y may be H, D, OH, or OR and, for example, may be H, D, or OR. For example, when the alkyne compound contains two or more Ys, the two or more Ys may each independently be selected from H, D, OH, and OR.

In a particularly preferred embodiment, at least one of $X_2(s)$ is CHY or CDY, and, for example, each $X_2$ may be CHY or CDY.

In the embodiment, preferably, Y may be H, D, OH, or OR and, for example, may be H, D, or OR. For example, when the alkyne compound contains two or more Ys, the two or more Ys may each independently be selected from H, D, and OR.

In the embodiment, preferably, the one or more $X_2$s contain at least one CDD and contain at least one CDOR. In the description, the at least one CDOR may be CDO-(an alcohol protective group). The alcohol protective group is as described above.

In Formula (I), $X_3$ is C or $^{13}$C. In other words, $X_3$ constitutes the alkyne moiety of the enyne structure.

In Formula (I), at least one selected from the group consisting of $X_1$, $X_2(s)$, and $X_3$ is modified with a stable isotope D, $^{13}$C, $^{18}$O, or $^{15}$N. In other words, the alkyne compound of Formula (I) is a compound having at least one stable isotope, and the at least one stable isotope may be contained in one or more of $X_1$, $X_2(s)$, and $X_3$.

2-2. Structure of Alkyne Compound of Formula (100)

In a particularly preferred embodiment, in Formula (I), m is 4. In the embodiment, the alkyne compound may be a compound represented by Formula (100). The compound represented by Formula (100) will next be described.

[Chemical Formula 9]

(100)

In Formula (100), A is a linear carbon chain having an alkynyl group at an end and having a vinyl group at another end.

In Formula (100), $X_1$ may be CH or $^{13}$CH.

When $X_1$ is CH, at least one selected from the group consisting of $X_{21}$, $X_{22}$, $X_{23}$, $X_{24}$, and $X_3$ is modified with a stable isotope D, $^{13}$C, $^{18}$O, or $^{15}$N.

When $X_1$ is $^{13}$CH, none of $X_{21}$, $X_{22}$, $X_{23}$, $X_{24}$, and $X_3$ may be modified with a stable isotope, or also in this case, at least one selected from the group consisting of $X_{21}$, $X_{22}$, $X_{23}$, $X_{24}$, and $X_3$ may be modified with a stable isotope D, $^{13}$C, $^{18}$O, or $^{15}$N.

In Formula (100), $X_{21}$, $X_{22}$, $X_{23}$, and $X_{24}$ are each independently selected from CHY, CDY, $^{13}$CHY, $^{13}$CDY, CO, $^{13}$CO, $C^{18}$O, and $^{13}C^{18}$O. In a preferred embodiment, at least one selected from the group consisting of $X_{21}$, $X_{22}$, $X_{23}$, and $X_{24}$ is CHY or CDY, and, for example, each of $X_{21}$, $X_{22}$, $X_{23}$, and $X_{24}$ may be CHY or CDY.

When at least one selected from the group consisting of $X_{21}$, $X_{22}$, $X_{23}$, and $X_{24}$ is modified with a stable isotope D, $^{13}$C, $^{18}$O, or $^{15}$N, neither $X_1$ nor $X_3$ may be modified with a stable isotope, or also in this case, one or both of $X_1$ and $X_3$ may be modified with a stable isotope.

When none of $X_{21}$, $X_{22}$, $X_{23}$, and $X_{24}$ is modified with a stable isotope D, $^{13}$C, $^{18}$O, or $^{15}$N, one or both of $X_1$ and $X_3$ are modified with a stable isotope.

In Formula (100), Y and R of Y may be as described in Formula (I). In other words, Y may be H, D, $NH_2$, $^{15}NH_2$, OH, $^{18}$OH, SH, OR, O(CO)R, $OSO_3H$, $OSO_3Na$, or a sugar substituent. R may be an alcohol protective group, an alkyl group, an alkenyl group, or an aryl group.

In Formula (100), $X_3$ is C or $^{13}$C.

In Formula (100), at least one selected from the group consisting of $X_1$, $X_{21}$, $X_{22}$, $X_{23}$, $X_{24}$, and $X_3$ is modified with a stable isotope D, $^{13}$C, $^{18}$O, or $^{15}$N. The alkyne compound of Formula (100) is a compound having at least one stable isotope, and the at least one stable isotope may be contained in one or more of $X_1$, $X_{21}$, $X_{22}$, $X_{23}$, $X_{24}$, and $X_3$.

2-3. Usage of Alkyne Compound

The alkyne compound according to the present invention may be used to produce a vitamin D compound as described above, and more specifically, may be used as a material to form the A ring moiety of a vitamin D compound.

In an embodiment, by reacting a bromoolefin compound having the CD ring of a vitamin D compound with the alkyne compound according to the present invention, a vitamin D compound may be produced. In the reaction, Br of the bromoolefin compound is reacted with the alkyne moiety of the alkyne compound. This results in the formation of a vitamin D compound. Specific examples of the reaction will be described in the examples.

As the bromoolefin compound, a compound known in the art may be used. The type of the bromoolefin compound (especially the side chain moiety of the D ring) may be appropriately selected by a person skilled in the art according to the type of vitamin D compound to be produced.

A hydroxy group of the alkyne compound to be reacted may be protected by an alcohol protective group, and in this case, the hydroxy group of a vitamin D compound after the reaction is also protected by the alcohol protective group. Hence, deprotection may be carried out after the reaction. A reagent used for the deprotection may be appropriately selected by a person skilled in the art according to conditions such as the type of alcohol protective group.

2-4. Production Method of Alkyne Compound

The alkyne compound of the present invention may be produced, for example, from a linear polyhydric alcohol compound as a starting material. The linear polyhydric alcohol compound may be, for example, a polyhydric alcohol compound having one or multiple hydroxy group(s) at each end of the linear chain. The linear polyhydric alcohol compound may have one or more hydroxy groups on at least one of the carbons other than the terminal carbons. These hydroxy groups may be protected, for example, by a protective group known in the art (such as the above alcohol protective group).

For example, a method for producing the alkyne compound of the present invention may comprise a labeling step of deuterium labeling a linear polyhydric alcohol compound by deuterium labeling reaction, an alkyne group introduction step of introducing an alkyne structure to one end of the deuterium-labeled polyhydric alcohol, and an alkenyl group introduction step of introducing, after the alkyne group introduction step, an alkene structure to the other end of the polyhydric alcohol. As described above, by deuterium labeling a linear polyhydric alcohol compound, introducing an alkyne group, and introducing an alkenyl group, the alkyne compound of the present invention may be produced. Specific examples of the production method will be described in Examples below.

The linear polyhydric alcohol compound is known in the art, and the carbon number of the linear polyhydric alcohol compound and the positions and the number of hydroxy groups may be appropriately selected according to the carbon number of an alkyne compound to be produced and the positions and the number of hydroxy groups in the alkyne compound. By controlling the carbon number, the positions, and the number, various alkyne compounds may be produced.

The labeling step may be carried out by a reaction known in the art. The labeling step may comprise deuteration reaction, for example, using a certain catalyst (such as a ruthenium catalyst). FIG. 11 shows natural materials, malic acid and aspartic acid, as compound examples used to produce the linear polyhydric alcohol compound. As shown in the figure, by subjecting malic acid or aspartic acid to deuteration, a deuterated linear polyhydric alcohol may be prepared. As shown in the figure, a malic acid or an aspartic acid labeled with one or more of $^{13}C$, $^{15}N$, and $^{18}O$ may be subjected to deuteration. By such deuteration, a linear polyhydric alcohol labeled with one or more of $^{13}C$, $^{15}N$, and $^{18}O$ may be produced. By further carrying out the production method using the linear polyhydric alcohol, an alkyne compound labeled with one or more of $^{13}C$, $^{15}N$, and $^{18}O$ may be produced.

A malic acid or an aspartic acid labeled with a plurality of $^{13}Cs$, a plurality of $^{15}Ns$, or a plurality of $^{18}Os$ may be subjected to deuteration. By such deuteration, a linear polyhydric alcohol labeled with a plurality of $^{13}Cs$, a plurality of $^{15}Ns$, or a plurality of $^{18}Os$ may be prepared. By carrying out the production method using the linear polyhydric alcohol, an alkyne compound labeled with a plurality of $^{13}Cs$, a plurality of $^{15}Ns$, or a plurality of $^{18}Os$ may be produced.

As described above, various types of stable isotope-labeled starting materials may be prepared, and an alkyne compound corresponding to each starting material may be produced.

The alkyne group introduction step may be carried out by a reaction known in the art. For example, the alkyne group introduction step may comprise a terminal alkyne introduction reaction in which trimethylsilylacetylene is used to introduce an alkyne group to the one end.

The alkenyl group introduction step may be carried out by a reaction known in the art. For example, the alkenyl group introduction step may comprise a cyano group introduction reaction to introduce a cyano group to the other end and a reaction to change the cyano group into an alkenyl group.

3. Second Embodiment (Vitamin D Compound)

The present invention provides a vitamin D compound represented by Formula (III). The vitamin D compound is labeled with a stable isotope as described herein. The vitamin D compound may be used, for example, in mass spectrometry and, for example, may be used in mass spectrometry for quantification by isotope dilution method. The mass spectrometry may be mass spectrometry for detection and/or quantification of a vitamin D metabolite. The vitamin D compound according to the present invention advantageously has excellent storage stability.

3-1. Structure of Vitamin D Compound of Formula (III)

The vitamin D compound of Formula (III) will next be described.

[Chemical Formula 10]

(III)

In Formula (III), A' represents a cyclic carbon chain. The cyclic carbon chain may be a cyclic carbon chain corresponding to the A ring of a vitamin D compound.

A', seco-B, C, and D are letters that are attached merely for convenience to explain about moieties in a vitamin D compound and do not represent any substance such as an element constituting the vitamin D compound of Formula (III).

In Formula (III), $X'_1$ may be C or $^{13}C$. When the vitamin D compound of Formula (III) is produced by using the alkyne compound of Formula (I), the carbon of $X_1$ in Formula (I) corresponds to the carbon of $X'_1$ in Formula (III).

When $X'_1$ is C, at least one selected from the group consisting of $X'_2(s)$ and $X'_3$ is modified with a stable isotope D, $^{13}C$, $^{18}O$, or $^{15}N$.

When $X'_1$ is $^{13}C$, none of $X'_2(s)$ and $X'_3$ may be modified with a stable isotope, or also in this case, at least one selected from the group consisting of $X'_2(s)$ and $X'_3$ may be modified with a stable isotope D, $^{13}C$, $^{18}O$, or $^{15}N$.

In Formula (III), $X'_2$ is CHY', CDY', $^{13}CHY'$, $^{13}CDY'$, CO, $^{13}CO$, $C^{18}O$, or $^{13}C^{18}O$. The vitamin D compound of Formula (III) has linearly continuing m pieces of $X'_2s$ between $X'_1$ and $X'_3$. In Formula (III), m is an integer from 1 to 4. When m is 2 or more, $X'_2s$ are identical or different. In other words, when the vitamin D compound has two or more $X'_2s$, the two or more $X'_2s$ are each independently selected from CHY', CDY', $^{13}CHY'$, $^{13}CDY'$, CO, $^{13}CO$, $C^{18}O$, and $^{13}C^{18}O$.

Preferably, m is 2, 3, or 4, m is more preferably 3 or 4, and m is even more preferably 4. An embodiment in which m is 4 will be further described later with reference to Formula (300).

When the vitamin D compound of Formula (III) is produced by using the alkyne compound of Formula (I), the carbon of $X_2$ in Formula (I) corresponds to the carbon of $X'_2$ in Formula (III).

When at least one of $X'_2(s)$ is modified with a stable isotope D, $^{13}C$, $^{18}O$, or $^{15}N$, neither $X'_1$ nor $X'_3$ may be modified with a stable isotope, or also in this case, one or both of $X'_1$ and $X'_3$ may be modified with a stable isotope.

When none of $X'_2(s)$ is modified with a stable isotope D, $^{13}C$, $^{18}O$, or $^{15}N$, one or both of $X'_1$ and $X'_3$ are modified with a stable isotope.

In Formula (III), Y' is H, D, $NH_2$, $^{15}NH_2$, OH, $^{18}OH$, SH, OR', O(CO)R', $OSO_3H$, $OSO_3Na$, or a sugar substituent. When Formula (III) contains two or more Y's, Y's are identical or different. In other words, when the alkyne compound has two or more Y's, the two or more Y's are each independently selected from H, D, $NH_2$, $^{15}NH_2$, OH, $^{18}OH$, SH, OR, O(CO)R, $OSO_3H$, $OSO_3Na$, and a sugar substituent.

When the vitamin D compound of Formula (III) is produced by using the alkyne compound of Formula (I), Y in Formula (I) corresponds to Y' in Formula (III).

In Formula (III), R' is an alkyl group, an alkenyl group, or an aryl group. When Formula (III) contains two or more R's, R's are identical or different. In other words, when the alkyne compound has two or more R's, the two or more R's are each independently selected from an alkyl group, an alkenyl group, and an aryl group.

When an alkyne compound of Formula (I) in which Y is OR and R of the OR is an alcohol protective group is used to produce a vitamin D compound of Formula (III), the alcohol protective group of OR in the alkyne compound of Formula (I) may be deprotected into OH in the vitamin D compound of Formula (III).

The alkyl group as R' in the vitamin D compound may be a substituted or unsubstituted, linear or branched alkyl group having 1 to 10 carbon atoms. The linear or branched alkyl group may, for example, have 1 to 8, 1 to 6, or 1 to 4 carbon atoms. The number of carbon atoms excludes the number of carbon atoms of substituents.

The alkenyl group as R' in the vitamin D compound may be a linear or branched alkenyl group having 2 to 10 carbon atoms. The linear or branched alkenyl group may, for example, have 2 to 8, 2 to 6, or 2 to 4 carbon atoms. The number of carbon atoms excludes the number of carbon atoms of substituents.

The aryl group as R' of the vitamin D compound may be a substituted or unsubstituted aryl group having 6 to 20 carbon atoms. The aryl group preferably has 6 to 18 carbon atoms and may, for example, have 6 to 16, 6 to 14, 6 to 12, or 6 to 10 carbon atoms. The number of carbon atoms excludes the number of carbon atoms of substituents. The aryl group may be an unsubstituted aryl group and may be, for example, a phenyl group or a naphthyl group.

In Formula (III), the sugar substituent may, for example, have the following structure.

[Chemical Formula 11]

Wo in the sugar substituent represented by the structure is identical with Wo described in Formula (I), and the description is applied to Wo in Formula (III).

In an embodiment, at least one of $X'_2(s)$ is CHY', CDY', $^{13}CHY'$, or $^{13}CDY'$, and, for example, each $X'_2$ may be CHY', CDY', $^{13}CHY'$, or $^{13}CDY'$.

In the embodiment, preferably, Y' may be H, D, OH, or OR' and, for example, may be H, D, OH, or OR'. For example, when the vitamin D compound contains two or more Y's, the two or more Y's may each independently be selected from H, D, OH, and OR'.

In a particularly preferred embodiment, at least one of $X'_2(s)$ is CHY' or CDY', and, for example, each $X'_2$ may be CHY' or CDY'.

In the embodiment, preferably, Y' may be H, D, or OH and, for example, may be H, D, or OH. For example, when the vitamin D compound contains two or more Y's, the two or more Y's may each independently be selected from H, D, and OH.

In the embodiment, preferably, the one or more $X'_2s$ contain at least one CDD and contain at least one CDOH.

In Formula (III), $X'_3$ is C or $^{13}C$. When the vitamin D compound of Formula (III) is produced by using the alkyne compound of Formula (I), the carbon of $X_3$ in Formula (I) corresponds to the carbon of $X'_3$ in Formula (III).

As shown in Formula (III), $X'_1$ and $X'_3$ may be bonded, or $X'_1$, $X'_2(s)$, and $X'_3$ may form a ring structure. The ring structure corresponds to the A ring in the vitamin D compound.

In Formula (III), at least one selected from the group consisting of $X'_1$, $X'_2(s)$, and $X'_3$ is modified with a stable isotope D, $^{13}C$, $^{18}O$, or $^{15}N$. In other words, the vitamin D compound of Formula (III) is a compound having at least one stable isotope, and the at least one stable isotope may be contained in one or more of $X'_1$, $X'_2(s)$, and $X'_3$.

The vitamin D compound has a seco-B ring, a C ring, and a D ring as shown in Formula (III). To the D ring, P representing a side chain may be bonded.

In Formula (III), P may be a $C_1$ to $C_{10}$ alkyl group unsubstituted or substituted with a hydroxy group or a $C_2$ to $C_{10}$ alkenyl group unsubstituted or substituted with a hydroxy group. The alkyl group or the alkenyl group may have a lactone group substituted with a hydroxy group.

In an embodiment, P in Formula (III) may be represented by:

[Chemical Formula 12]

In the formulae, Q, Q', Q", Q''', and Q'''' are each independently H, $CH_2$, $CH_3$, $C_2H_5$, O, OH, or a sugar substituent.

More specific examples of P are shown below. P may be any of them.

[Chemical Formula 13]

The structure of P is not limited to the above exemplified structures, and any of the D ring side chains in vitamin D compounds known in the art may be used as the P structure.

3-2. Structure of Vitamin D Compound of Formula (200)

In a particularly preferred embodiment, in Formula (III), m is 4. In the embodiment, the vitamin D compound may be a compound represented by Formula (200). The compound represented by Formula (200) will next be described.

[Chemical Formula 14]

(200)

In Formula (200), A' represents a cyclic carbon chain. A' is a moiety corresponding to the A ring of a vitamin D compound.

In Formula (200), $X'_1$ may be C or $^{13}C$. When the vitamin D compound of Formula (200) is produced by using the alkyne compound of Formula (100), the carbon of $X_1$ in Formula (100) corresponds to the carbon of $X'_1$ in Formula (200).

When $X'_1$ is C, at least one selected from the group consisting of $X'_{21}$, $X'_{22}$, $X'_{23}$, $X'_{24}$, and $X'_3$ is modified with a stable isotope D, $^{13}C$, $^{18}O$, or $^{15}N$.

When $X'_1$ is $^{13}C$, none of $X'_{21}$, $X'_{22}$, $X'_{23}$, $X'_{24}$, and $X'_3$ may be modified with a stable isotope, or also in this case, at least one selected from the group consisting of $X'_{21}$, $X'_{22}$, $X'_{23}$, $X'_{24}$, and $X'_3$ may be modified with a stable isotope D, $^{13}C$, $^{18}O$, or $^{15}N$.

In Formula (200), $X'_{21}$, $X'_{22}$, $X'_{23}$, and $X'_{24}$ are each independently selected from CHY', CDY', $^{13}CHY'$, $^{13}CDY'$, CO, $^{13}CO$, $C^{18}O$, and $^{13}C^{18}O$. In a preferred embodiment, at least one selected from the group consisting of $X'_{21}$, $X'_{22}$, $X'_{23}$, and $X'_{24}$ is CHY' or CDY', and, for example, each of $X'_{21}$, $X'_{22}$, $X'_{23}$, and $X'_{24}$ may be CHY' or CDY'.

When the vitamin D compound of Formula (200) is produced by using the alkyne compound of Formula (100), the carbons of $X_{21}$, $X_{22}$, $X_{23}$, and $X_{24}$ in Formula (100) correspond to the carbons of $X'_{21}$, $X'_{22}$, $X'_{23}$, and $X'_{24}$ in Formula (200).

When at least one selected from the group consisting of $X'_{21}$, $X'_{22}$, $X'_{23}$, and $X'_{24}$ is modified with a stable isotope D, $^{13}C$, $^{18}O$, or $^{15}N$, neither $X'_1$ nor $X'_3$ may be modified with a stable isotope, or also in this case, one or both of $X'_1$ and $X'_3$ may be modified with a stable isotope.

When none of $X'_{21}$, $X'_{22}$, $X'_{23}$, and $X'_{24}$ is modified with a stable isotope D, $^{13}C$, $^{18}O$, or $^{15}N$, one or both of $X'_1$ and $X'_3$ are modified with a stable isotope.

In Formula (200), Y' or R' in Y' may be as described in Formula (III). In other words, Y' may be H, D, $NH_2$, $^{15}NH_2$, OH, $^{18}OH$, SH, OR', O(CO)R', $OSO_3H$, $OSO_3Na$, or a sugar substituent. R' is an alkyl group, an alkenyl group, or an aryl group.

In an embodiment, at least one selected from the group consisting of $X'_{21}$, $X'_{22}$, $X'_{23}$, and $X'_{24}$ is CHY', CDY', $^{13}CHY'$, or $^{13}CDY'$, and, for example, each of $X'_{21}$, $X'_{22}$, $X'_{23}$, and $X'_{24}$ may be CHY', CDY', $^{13}CHY'$, or $^{13}CDY'$.

In the embodiment, preferably, Y' may be H, D, OH, or OR' and, for example, may be H, D, OH, or OR'. For example, when the vitamin D compound contains two or more Y's, the two or more Y's may each independently be selected from H, D, OH, and OR'.

In a particularly preferred embodiment, at least one selected from the group consisting of $X'_{21}$, $X'_{22}$, $X'_{23}$, and $X'_{24}$ is CHY' or CDY', and, for example, each of $X'_{21}$, $X'_{22}$, $X'_{23}$, and $X'_{24}$ may be CHY' or CDY'.

In the embodiment, preferably, Y' may be H, D, or OH and, for example, may be H, D, or OH. For example, when the vitamin D compound contains two or more Y's, the two or more Y's may each independently be selected from H, D, and OH.

In the embodiment, preferably, the one or more of $X'_{21}$, $X'_{22}$, $X'_{23}$, and $X'_{24}$ contain at least one CDD and contain at least one CDOH.

In Formula (200), $X'_3$ is C or $^{13}$C. When the vitamin D compound of Formula (200) is produced by using the alkyne compound of Formula (100), the carbon of $X_3$ in Formula (100) corresponds to the carbon of $X'_3$ in Formula (200).

As shown in Formula (200), $X'_1$ and $X'_3$ may be bonded, or $X'_1$, $X'_{21}$, $X'_{22}$, $X'_{23}$, $X'_{24}$, and $X'_3$ may form a ring structure. The ring structure corresponds to the A ring in the vitamin D compound.

In Formula (200), at least one selected from the group consisting of $X'_1$, $X'_{21}$, $X'_{22}$, $X'_{23}$, $X'_{24}$, and $X'_3$ is modified with a stable isotope D, $^{13}$C, $^{18}$O, or $^{15}$N. In other words, the vitamin D compound of Formula (200) is a compound having at least one stable isotope, and the at least one stable isotope may be contained in one or more of $X'_1$, $X'_{21}$, $X'_{22}$, $X'_{23}$, $X'_{24}$, and $X'_3$.

P in Formula (200) is as described in Formula (III), and the description is applied to Formula (200).

The vitamin D compound of the present invention may be a stable isotope-labeled compound of 25-hydroxyvitamin $D_3$ ($25OHD_3$), 3-epi-25-hydroxyvitamin $D_3$ (3-epi-$25OHD_3$), 25-hydroxyvitamin $D_2$ ($25OHD_2$), 24R,25-dihydroxyvitamin $D_3$ ($24R,25(OH)_2D_3$), 23S,25-dihydroxyvitamin $D_3$ ($23S,25(OH)_2D_3$), 1$\alpha$,25-dihydroxyvitamin $D_3$ (1$\alpha$,25$(OH)_2D_3$), 25-hydroxyvitamin $D_3$-26R,23S-lactone ($25OHD_3$-26R,23S-lactone), 1$\alpha$,25-dihydroxyvitamin $D_3$-26R,23S-lactone (1$\alpha$,25$(OH)_2D_3$-26R,23S-lactone), 1$\alpha$,25-dihydroxyvitamin $D_2$ (1$\alpha$,25$(OH)_2D_2$), 1$\alpha$,24R,25-trihydroxyvitamin $D_3$ (1$\alpha$,24R,25$(OH)_3D_3$), or 4$\beta$,25-dihydroxyvitamin $D_3$ (4$\beta$,25$(OH)_2D_3$). The chemical structures of these compounds are shown in FIG. 10. In other words, the vitamin D compound of the present invention may be a vitamin D compound in which the A ring moiety in the chemical structure of a corresponding compound shown in the figure is labeled with a stable isotope in accordance with the present invention. In an embodiment, the vitamin D compound of the present invention may be a vitamin D compound in which at least one of the hydrogen atoms bonded to the carbon atoms that form the A ring moiety in the chemical structure of a corresponding compound is a deuterium atom. The number of deuterium atoms bonded to the carbon atoms that form the A ring moiety may be, for example, 2 or more and specifically 3 or more. The number of deuterium atoms bonded to the carbon atoms that form the A ring moiety may be, for example, 7 or less, specifically 6 or less, and more specifically 5 or less.

3-3. Usage of Vitamin D Compound

The vitamin D compound of the present invention may be used in various analytical methods, especially in mass spectrometry, and, for example, in isotope dilution mass spectrometry. The mass spectrometry may be more specifically LC-MS/MS or LC-MS. Carrying out the analytical method with the vitamin D compound of the present invention enables detection or quantification of a vitamin D compound (for example, a vitamin D metabolite in a biological sample) that has the same chemical structure but is not isotope-labeled.

The vitamin D compound of the present invention may, for example, be used as a standard in the analytical method and may be specifically used as an internal standard.

In the mass spectrometry, the vitamin D compound of the present invention may be derivatized. The derivatization may improve the detection accuracy. For the derivatization, a derivatization reagent known in the art may be used.

In the mass spectrometry, the vitamin D compound of the present invention or the derivatized vitamin D compound may be ionized. The ionization may be carried out, for example, by electrospray ionization (ESI), atmospheric pressure chemical ionization (APCI), or matrix-assisted laser desorption ionization (MALDI) for more efficient ionization and may be carried out by any ionization other than these ionizations. The ionization enables more accurate detection or quantification.

The mass spectrometry may be carried out, for example, with a liquid chromatograph-tandem mass spectrometer (LC-MS/MS) or a matrix-assisted laser desorption/ionization mass spectrometer (MALDI-MS), but the apparatus for carrying out the mass spectrometry step is not limited to them. A specific procedure in the mass spectrometry step may be appropriately designed by a person skilled in the art according to, for example, the ionization method to be used or the apparatus to be used.

3-4. Production Method of Vitamin D Compound

The vitamin D compound of the present invention may be produced by reacting the alkyne compound of the present invention with a compound for forming the CD ring of an intended vitamin D compound. Examples of the compound for forming the CD ring include olefin compounds having the CD ring. As the olefin compound, a compound known in the art may be used. The olefin compound may, for example, be a compound having the structure represented by Formula (II). As the compound, a compound known in the art may be used.

[Chemical Formula 15]

II

In the compound of Formula (II), C and D are moieties to form the C ring and the D ring, respectively, when a vitamin D compound is synthesized.

P in the compound of Formula (II) may be, for example, the same as P described in Formula (III), and a hydroxy group in P may be protected by the alcohol protective group described in the compound of Formula (II). The alcohol protective group may be, for example, TES.

Z in the compound of Formula (II) may be a halogen group or a pseudo halogen group and may be, for example, F, Cl, Br, I, or OTf. In an embodiment, Z is Br, and accordingly the compound of Formula (II) may be a bromoolefin compound.

In other words, the method for producing the vitamin D compound of the present invention may comprise reacting the alkyne compound of Formula (I) with the compound of Formula (II). More specifically, the reacting may comprise reacting the alkynyl group in the alkyne compound of Formula (I) with Z in the compound of Formula (II). By the reaction, a bond is formed between the carbon bonded to Z in the compound of Formula (II) and the carbon that is one of the two carbons constituting the alkynyl group of the alkyne compound of Formula (I) but is not $X_3$, and a seco-B ring is formed. In addition, a bond is formed between $X_1$ and $X_3$ in the alkyne compound of Formula (I), and an A' ring is formed. As described above, the A' ring and the seco-B ring are formed, and the vitamin D compound of the present invention is formed.

4. Third Embodiment (Analytical Method Using Vitamin D Compound)

4-1. Embodiment of Analytical Method

The present invention also provides an analytical method using the vitamin D compound according to the present invention. The analytical method may comprise analyzing a sample by mass spectrometry as described in the section 3-3. The sample may be, for example, a sample containing, as a target to be detected or quantified, a vitamin D compound that has the same chemical structure as the vitamin D compound according to the present invention but is not isotope-labeled or a sample that may contain such an unlabeled compound (or a sample that may contain no such an unlabeled compound). The sample is, for example, a biological sample, specifically may be a body fluid or a sample derived from a body fluid, and more specifically may be serum, blood plasma, blood, urine, spinal fluid, or saliva.

In an embodiment, the vitamin D compound of the present invention may be used as an internal standard in the analytical method. The method of using the vitamin D compound of the present invention as an internal standard may be a method known in the art. For example, in the analytical method, the amount or the concentration of a compound to be analyzed (for example, a vitamin D metabolite) may be determined on the basis of a relation between peak area ratio and concentration ratio of the vitamin D compound of the present invention.

4-2. Alternative Embodiment of Analytical Method

In an alternative embodiment of the analytical method described in the section 4-1, a vitamin D compound having no hydroxy group at position 1 of the A ring may be analyzed separately from a vitamin D compound having a hydroxy group at position 1 of the A ring. More specifically, the vitamin D compound having no hydroxy group at position 1 of the A ring may include at least one of a 2-hydroxyvitamin D compound and a 4-hydroxyvitamin D compound. More specifically, the vitamin D compound having no hydroxy group at position 1 of the A ring may include at least one of a 4β,25-dihydroxyvitamin D3 compound and a 4-hydroxyvitamin D compound. The alternative embodiment will next be described in detail.

As described above, detection and quantification of a vitamin D metabolite in a biological sample are highly demanded in the clinical field and the food nutrition field. Of various vitamin D metabolites, one of the most important metabolites in terms of physiological activity is 1α,25-dihydroxyvitamin $D_3$ also referred to as an active vitamin D, and the selective extraction thereof is extremely important. LC-MS/MS, which combines chromatographic separation and separation in terms of m/z (mass-to-charge ratio) of fragment ions, has high separation performance, and using a derivatization reagent improves the sensitivity.

Figure 6:
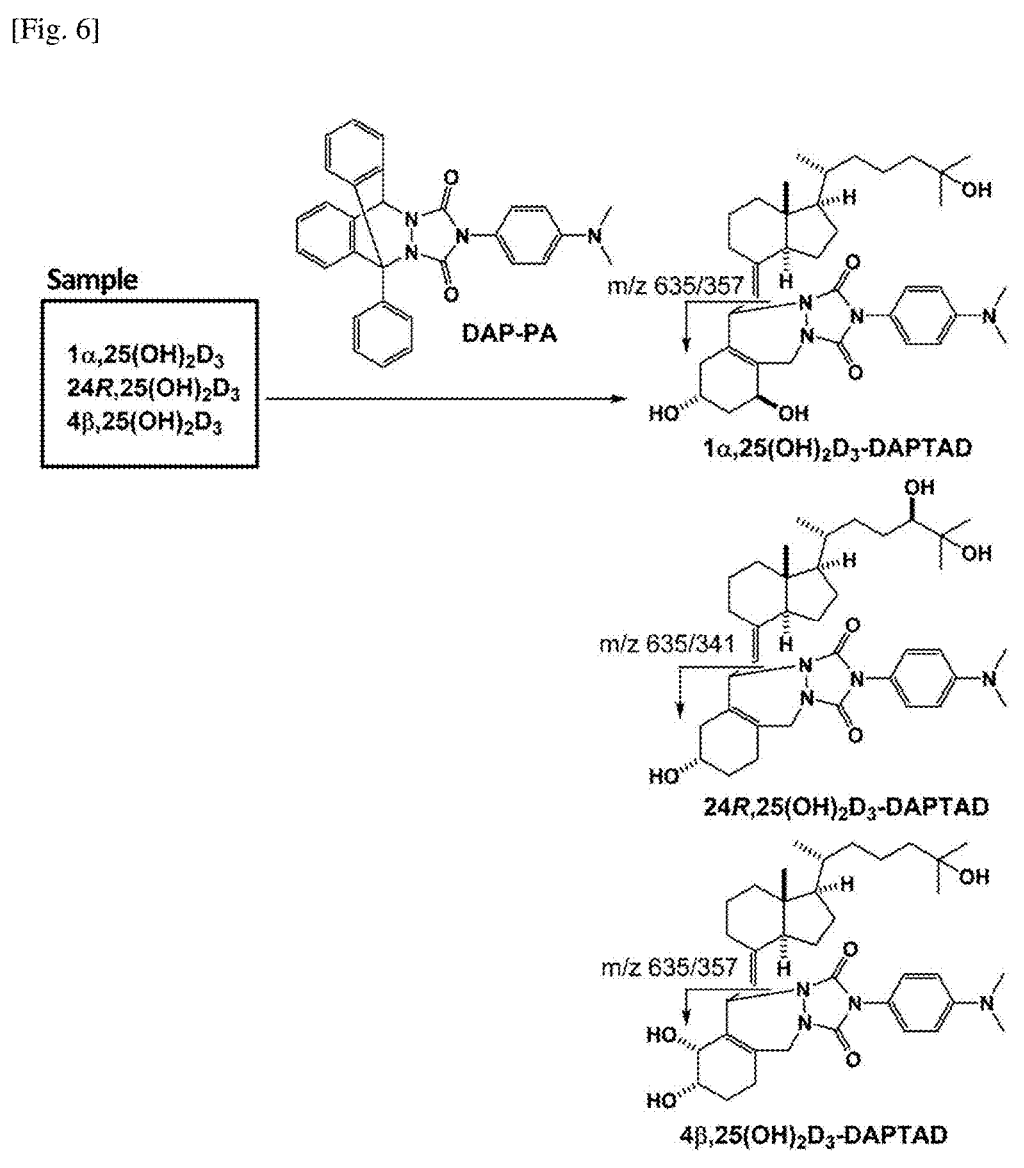

However, two or more vitamin D metabolites having different chemical structures may not be individually detected/quantified only by LC-MS/MS. For example, two or more regioisomers different only in the position of a hydroxy group may not be individually detected/quantified only by LC-MS/MS. An example of such a case will be described with reference to FIG. 6.

As shown in the figure, an example sample (Sample) containing three vitamin D compounds, 1α,25-dihydroxyvitamin $D_3$ (1α,25(OH)$_2$$D_3$), 24R,25-dihydroxyvitamin $D_3$ (24R,25(OH)$_2$$D_3$), and 4β,25-dihydroxyvitamin $D_3$ (4β,25 (OH)$_2$$D_3$), is to be analyzed.

When the sample is derivatized, for example, with a derivatization reagent DAP-PA shown in the figure, three derivatized compounds are formed as shown on the right in the figure. These three derivatives are cleaved at positions of the arrows in the figure. As apparent from the cleaved products, 24R,25-dihydroxyvitamin $D_3$ can be separated from 1α,25-dihydroxyvitamin $D_3$ in terms of m/z of fragment ions, but 4β,25-dihydroxyvitamin $D_3$ cannot be separated. In addition, 1α,25-dihydroxyvitamin $D_3$ and 4β,25-dihydroxyvitamin $D_3$ are difficult to separate by chromatography.

When a sample is subjected to a certain separation treatment, and then the sample after the separation treatment is subjected to analysis treatment using the vitamin D compound according to the present invention, two or more vitamin D compounds that are difficult to separate as described above can be individually detected or quantified. The present invention also provides an analytical method of selectively detecting or quantifying two or more vitamin D compounds that are difficult to separate only by LC-MS/MS. In other words, the analytical method of the present invention also provides an analytical method of individually detecting or quantifying two or more regioisomers of vitamin D compounds. The two or more regioisomers may be regioisomers different in the position of a hydroxy group bonded to the A ring as described above. The two or more regioisomers may have the same molecular weight.

In an embodiment, the analytical method of the present invention may comprise a fractionating step of fractionating a sample into at least one first fraction in which a vitamin D compound having a hydroxy group at position 1 of the A ring is collected and at least one second fraction in which no vitamin D compound having a hydroxy group at position 1 of the A ring is collected, and an analysis step of analyzing one or both of the at least one first fraction and the at least one second fraction by using the vitamin D compound of the present invention.

In the embodiment, the second fraction may contain a vitamin D compound having no hydroxy group at position 1 of the A ring.

The sample does not necessarily contain a vitamin D compound having a hydroxy group at position 1 of the A ring. In other words, the first fraction may be a fraction prepared by carrying out an operation for collecting a vitamin D compound having a hydroxy group at position 1 of the A ring, and the fraction may not contain the vitamin D compound.

The fractionating step and the analysis step will next be described.

4-2-1. Fractionating Step

The sample to be subjected to the fractionating step may be the sample described in the section 4-1.

Figures 7, 8:
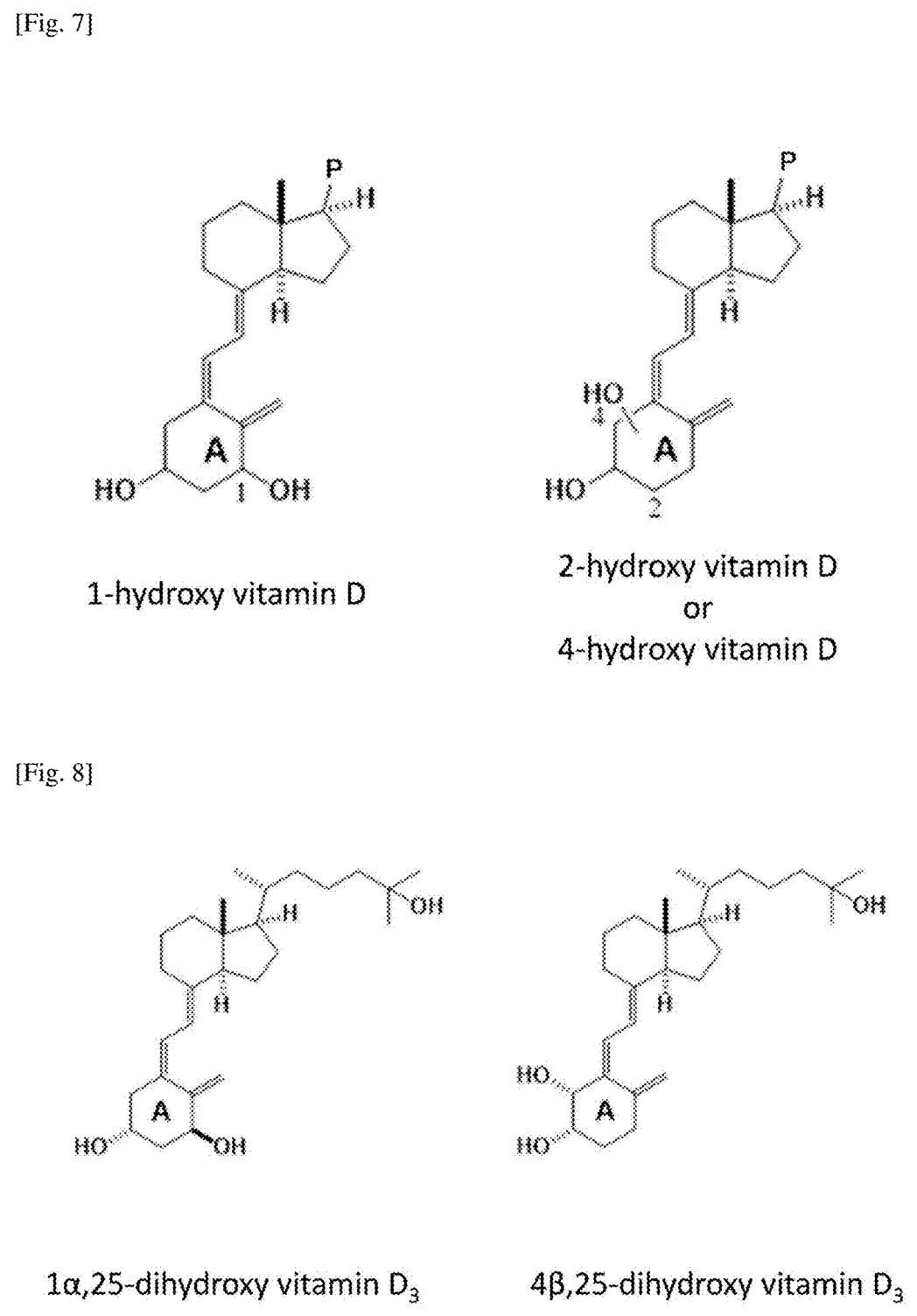

The vitamin D compound having a hydroxy group at position 1 of the A ring may be, for example, a vitamin D compound having the structure shown on the left in FIG. 7 or may be a 1-hydroxyvitamin D compound. The 1-hydroxyvitamin D compound has a hydroxy group at position 1 of the A ring as shown in the figure. The 1-hydroxyvitamin D compound may have a hydroxy group at position 3 of the A ring. P in the 1-hydroxyvitamin D compound may be as described in Formula (III).

The vitamin D compound having no hydroxy group at position 1 of the A ring may be a vitamin D compound having the structure shown on the right in FIG. 7 or may be a 2-hydroxyvitamin D compound or a 4-hydroxyvitamin D compound. The 2-hydroxyvitamin D compound or the 4-hydroxyvitamin D compound has a hydroxy group at position 2 or position 4 of the A ring as shown in the figure. The 2-hydroxyvitamin D compound or the 4-hydroxyvitamin D compound may have a hydroxy group at position 3 of the A ring. P in the 2-hydroxyvitamin D compound or the 4-hydroxyvitamin D compound may be as described in Formula (III).

In particular, the 1-hydroxyvitamin D compound and the 2-hydroxyvitamin D compound or the 4-hydroxyvitamin D compound may be identical with each other except the position of a hydroxy group on the A ring.

The 1-hydroxyvitamin D compound may be, for example, $1\alpha,25$-dihydroxyvitamin $D_3$ as shown on the left in FIG. 8. The 4-hydroxyvitamin D compound may be $4\beta,25$-dihydroxyvitamin $D_3$ as shown on the right in the figure.

In other words, the sample to be subjected to the analytical method may be a sample that may contain $1\alpha,25$-dihydroxyvitamin $D_3$ and/or $4\beta,25$-dihydroxyvitamin $D_3$ as analytical targets.

The sample to be subjected to the analytical method does not necessarily contain a vitamin D compound as the analytical target, or an analysis result may reveal that a sample does not contain any vitamin D compound as the analytical target.

The fractionating step may be carried out with a capturing substance that selectively captures (for example, binds or adsorbs), for example, only the vitamin D compound having a hydroxy group at position 1 of the A ring. Examples of the capturing substance include, but are not necessarily limited to, an antibody and an aptamer. As the capturing substance, a reagent known in the art may be used, and a person skilled in the art may appropriately select the capturing substance according to the vitamin D compound to be captured.

In an embodiment, in the fractionating step, the sample may be loaded on a column containing an antibody that selectively captures only the vitamin D compound having a hydroxy group at position 1 of the A ring. Examples of the column include an antibody column, such as $1,25-(OH)_2$-Vitamin $D_3/D_2$-ImmuTube (Immundiagnostik AG).

By adding the sample to the column, the antibody in the column captures the vitamin D compound having a hydroxy group at position 1 of the A ring. Next, the vitamin D compound having no hydroxy group at position 1 of the A ring that has not been captured is recovered from the column, and the second fraction is prepared. Next, by carrying out a certain elution treatment, the captured vitamin D compound having a hydroxy group at position 1 of the A ring is recovered from the column, and the first fraction is prepared.

4-2-2. Analysis Step

In the analysis step, one or both of the at least one first fraction and the at least one second fraction is analyzed while the vitamin D compound of the present invention is used. The analyzing may be carried out by the mass spectrometry described in the section 4-1.

For example, the second fraction may be subjected to mass spectrometry using, as a standard, the vitamin D compound of the present invention corresponding to a target vitamin D compound that is supposedly contained in the second fraction (a compound having a chemical structure in which the A ring of the target vitamin D compound is labeled with a stable isotope). In an example in which the target vitamin D compound is $4\beta,25$-dihydroxyvitamin $D_3$, LC-MS/MS may be carried out by using, as an internal standard, a compound having a chemical structure in which the A ring of $4\beta,25$-dihydroxyvitamin $D_3$ is labeled with a stable isotope.

The first fraction may be subjected to mass spectrometry using, as a standard, the vitamin D compound of the present invention corresponding to a target vitamin D compound that is supposedly contained in the first fraction (a compound having a chemical structure in which the A ring of the target vitamin D compound is labeled with a stable isotope). In an example in which the target vitamin D compound is $1\alpha,25$-dihydroxyvitamin $D_3$, LC-MS/MS may be carried out by using, as an internal standard, a compound having a chemical structure in which the A ring of $1\alpha,25$-dihydroxyvitamin $D_3$ is labeled with a stable isotope.

By the analytical method as described above, two or more vitamin D compounds that are difficult to separate by only LC-MS/MS can be selectively detected or quantified.

For example, a 2- or 4-hydroxyvitamin D compound may be selectively collected by the analytical method, and the collected 2- or 4-hydroxyvitamin D compound may be analyzed by LC-MS/MS (liquid chromatography-tandem mass spectrometry). The analytical method is usable regardless of the mass spectrometer manufacturer.

Specifically, $4\beta,25$-dihydroxyvitamin $D_3$ is a regioisomer of $1\alpha,25$-dihydroxyvitamin $D_3$, which is referred to as an active vitamin D and is the most important in terms of physiology, and these vitamin $D_3$ compounds have the same molecular weight and the same fragmentation pattern in MS/MS, give substantially the same behavior in HPLC chromatograms, and are extremely difficult to separate. Hence, $4\beta,25$-dihydroxyvitamin $D_3$ is hidden by $1\alpha,25$-dihydroxyvitamin $D_3$, and the physiological role has been unknown. Phenomena that have been thought to be the activity of $1\alpha,25$-dihydroxyvitamin $D_3$ might be derived from $4\beta,25$-dihydroxyvitamin $D_3$. The analytical method of the present invention enables separation and quantification of $4\beta,25$-dihydroxyvitamin $D_3$ and is useful to evaluate the function or activity of $4\beta,25$-dihydroxyvitamin $D_3$. In addition, the analytical method is also useful to more accurately evaluate the function or activity of $1\alpha,25$-dihydroxyvitamin $D_3$. As described above, the analytical method of the present invention is thought to greatly contribute to elucidation of the action mechanism of vitamin D compounds.

5. Fourth Embodiment (Production Method of Vitamin D)

The present invention also provides a method for producing the vitamin D compound of the present invention. The production method may be carried out as described in the section 3-4. In other words, in the production method of the present invention, the alkyne compound represented by Formula (I) may be used as the material for forming the A ring of a vitamin D compound. An example reaction scheme in this case is shown in FIG. 9A. As shown in the figure, in the production method of the present invention, the alkyne compound represented by Formula (I) may be reacted with a compound having the structure represented by Formula (II) to produce the vitamin D compound represented by Formula (III).

In a preferred embodiment, in the production method of the present invention, the alkyne compound represented by Formula (100) may be used as the material for forming the A ring of a vitamin D compound. An example reaction scheme in this case is shown in FIG. 9B. As shown in the figure, in the production method of the present invention, the alkyne compound represented by Formula (100) may be reacted with a compound having the structure represented by Formula (II) to produce the vitamin D compound represented by Formula (200).

EXAMPLES

6. Examples

The present invention will next be described in more detail with reference to examples, but the present invention is not limited to these examples.

6-1. Example 1: Production of Alkyne Compound and Vitamin D Compound (1) Synthesis of Alkyne Compound 10

Through the synthetic route shown below, an alkyne compound 10 was prepared. Each reaction in the synthetic route will be described below.

[Chemical Formula 16]

26

-continued (1-1) Synthesis of d₃-Diol 2

[Chemical Formula 17]

Under a hydrogen atmosphere, diol 1 (4.0 g, 21.0 mmol) was dissolved in deuterium oxide (80 mL), and ruthenium/carbon (4.0 g) was added at room temperature. The whole was stirred at 80° C. for 24 hours. After the stirring, the reaction solution was filtered through Celite (ethyl acetate/methanol=8/1), and the solvent was removed by evaporation. After the solvent removal, the residue was purified by silica gel column chromatography (hexane/ethyl acetate=1/1) to give d₃-diol 2 (3.84 g, yield: 96%) as a colorless liquid.

$^1$H NMR (400 MHz, CDCl$_3$) δ 4.34-4.42 (m, 1H), 4.12-4.17 (m, 1H), 1.68-1.81 (m, 2H), 1.19 (s, 9H).

HRMS (ESI, M+Na) calculated for C$_9$H$_{15}$D$_3$O$_4$Na 216.1291, found 216.1268.

(1-2) Synthesis of d3-Tosylate 3

[Chemical Formula 18]

(1-4) Synthesis of d3-Alkyne 5

[Chemical Formula 20]

Under an argon atmosphere, d3-diol 2 (7.8 g, 40.4 mmol) was dissolved in pyridine (80.8 mL), and tosyl chloride (8.08 mL, 42.4 mmol) was added. The whole was stirred at room temperature for 15 hours. After the stirring, distilled water (80 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=3/1) to give d3-tosylate 3 (7.05 g, yield: 50%) as a colorless liquid.

$^1$H NMR (300 MHz, CDCl3) δ 7.80 (d, J=8.8 Hz, 2H), 7.36 (d, J=8.7 Hz, 2H), 4.23-4.29 (m, 1H), 4.09-4.16 (m, 1H), 2.45 (s, 3H), 1.76-1.83 (m, 1H), 1.67-1.73 (m, 1H), 1.18 (s, 9H).

HRMS (ESI, M+Na) calculated for $C_{16}H_{21}D_3O_6SNa$ 370.1380, found 370.1413.

(1-3) Synthesis of d3-Epoxide 4

[Chemical Formula 19]

Under an argon atmosphere, d3-tosylate 3 (10.8 g, 31.1 mmol) was dissolved in dehydrated dimethylformamide (156 mL), and sodium hydride (1.49 g, 37.3 mmol) was added on ice. The whole was stirred at room temperature for 0.5 hour. After the stirring, distilled water (100 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=8/1) to give d3-epoxide 4 (3.96 g, yield: 73%) as a colorless liquid.

$^1$H NMR (300 MHz, CDCl3) δ 4.22 (t, J=6.0 Hz, 2H), 1.80-1.94 (m, 2H), 1.20 (s, 9H).

HRMS (ESI, M+Na) calculated for $C_9H_{13}D_3O_3Na$ 198.1185, found 198.1213.

Under an argon atmosphere, trimethylsilylacetylene (6.4 mL, 45.6 mmol) was dissolved in dehydrated tetrahydrofuran solution (24.8 mL), and n-butyllithium (1.6 M hexane solution) (13.7 mL, 35.6 mmol) was added dropwise at −78° C. to prepare a reaction mixture. The reaction mixture was stirred at the same temperature for 1 hour, and then a solution of d3-epoxide 4 (3.47 g, 19.8 mmol) in tetrahydrofuran and boron trifluoride-diethyl ether complex (3.23 mL, 25.7 mmol) were sequentially added dropwise. The reaction mixture was stirred at the same temperature for another 30 minutes. To the reaction solution, a saturated aqueous ammonium chloride solution (20 mL) was added, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=10/1) to give d3-alkyne 5 (3.33 g, yield: 61%) as a yellow liquid.

$^1$H NMR (300 MHz, CDCl3) δ 4.27-4.33 (m, 1H), 4.15-4.21 (m, 1H), 1.88-1.95 (m, 1H), 1.75-1.81 (m, 1H), 1.18 (s, 9H), 0.15 (s, 9H).

HRMS (ESI, M+Na) calculated for $C_{14}H_{23}D_3O_3SiNa$ 296.1737, found 296.1732.

(1-5) Synthesis of d3-Alkyne 6

[Chemical Formula 21]

Under an argon atmosphere, d$_3$-alkyne 5 (3.2 g, 11.7 mmol) was dissolved in dehydrated dimethylformamide (23.4 mL), and imidazole (2.15 g, 31.6 mmol), tert-butyldimethylsilyl chloride (3.50 g, 23.4 mmol), and 4-dimethylaminopyridine (143 mg, 1.17 mmol) were added. The whole was stirred at room temperature for 3 hours. After the stirring, distilled water (23 mL) was added to the reaction solution, and the mixture was extracted with a hexane/ethyl acetate mixed solvent. The organic phase was dried over anhydrous magnesium sulfate and was filtered, and the solvent was removed by evaporation. After the solvent removal, the residue was purified by silica gel column chromatography (hexane/ethyl acetate=10/1) to give d$_3$-alkyne 6 (4.61 g, yield: 100%) as a yellow liquid.

$^1$H NMR (300 MHz, CDCl$_3$) δ 4.19-4.25 (m, 1H), 4.05-4.13 (m, 1H), 1.93-2.00 (m, 1H), 1.73-1.79 (m, 1H), 1.22 (s, 9H), 0.88 (s, 9H), 0.14 (s, 9H), 0.08 (d, J=10.5 Hz, 6H).

HRMS (ESI, M+Na) calculated for C$_{20}$H$_{37}$D$_3$O$_3$Si$_2$Na 410.2602, found 410.2578.

(1-6) Synthesis of d$_3$-Alkyne 7

[Chemical Formula 22]

Under an argon atmosphere, d$_3$-alkyne 6 (4.51 g, 11.6 mmol) was dissolved in methanol (107 mL), and sodium methoxide (5.0 M methanol solution) (9.28 mL, 46.4 mmol) was added dropwise on ice. The mixture was stirred at room temperature for 24 hours. After the stirring, a saturated aqueous ammonium chloride solution (20 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=30/1) to give d$_3$-alkyne 7 (2.32 g, yield: 86%) as a yellow liquid.

$^1$H NMR (300 MHz, CDCl$_3$) δ 3.79-3.85 (m, 1H), 3.71-3.77 (m, 1H), 1.99 (s, 1H), 1.91-1.97 (m, 1H), 1.77-1.84 (m, 1H), 0.89 (s, 9H), 0.11 (s, 6H).

HRMS (ESI, M+Na) calculated for C$_{12}$H$_{21}$D$_3$O$_2$SiNa 254.1632, found 254.1631.

(1-7) Synthesis of d$_3$-Alkyne 8

[Chemical Formula 23]

Under an argon atmosphere, d$_3$-alkyne 7 (1.0 g, 4.32 mmol) was dissolved in methylene chloride (14 mL), and triethylamine (2.1 mL, 15.1 mmol), tosyl chloride (1.65 g, 8.64 mmol), and 4-dimethylaminopyridine (52 mg, 0.43 mmol) were added. The whole was stirred at room temperature for 2 hours. Distilled water (20 mL) was added to the reaction solution, and the mixture was extracted with methylene chloride. The organic phase was dried over anhydrous magnesium sulfate and was filtered, and the solvent was removed by evaporation. The residue was purified by silica gel column chromatography (hexane/ethyl acetate=20:1) to give d$_3$-alkyne 8 (1.67 g, yield: 99%) as a colorless liquid.

$^1$H NMR (300 MHz, CDCl$_3$) δ 7.79 (d, J=8.2 Hz, 2H), 7.34 (d, J=8.2 Hz, 2H), 4.13 (dd, J=7.3, 5.5 Hz, 2H), 2.45 (s, 3H), 2.06-1.94 (m, 2H), 1.82 (dt, J=14.2, 5.5 Hz, 1H), 0.82 (s, 9H), 0.02 (d, J=22.9 Hz, 6H).

HRMS (ESI, M+Na) calculated for C$_{19}$H$_{27}$D$_3$O$_4$SSiNa 408.1720, found 408.1677.

(1-8) Synthesis of d$_3$-Alkyne 9

[Chemical Formula 24]

Under an argon atmosphere, d$_3$-alkyne 8 (1.67 g, 4.27 mmol) was dissolved in dimethyl sulfoxide (14 mL), and sodium cyanide (314 mg, 6.41 mmol) was added at room temperature. The whole was stirred at 90° C. for 30 minutes. After the stirring, distilled water (20 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=20:1) to give d$_3$-alkyne 9 (1.0 g, yield: 100%) as a colorless liquid.

$^1$H NMR (300 MHz, CDCl$_3$) δ 2.47-2.37 (m, 2H), 2.08-1.95 (2H), 1.94-1.80 (m, 1H), 0.89 (s, 9H), 0.11 (d, J=1.4 Hz, 6H).

HRMS (ESI, M+Na) calculated for C$_{13}$H$_{20}$D$_3$NOSiNa 263.1635, found 263.1632.

(1-9) Synthesis of d$_3$-Alkyne 10

[Chemical Formula 25]

-continued

10

-continued

DIBAL-H
toluene, 0° C.
98%

12

Under an argon atmosphere, $d_3$-alkyne 9 (506 mg, 2.09 mmol) was dissolved in dehydrated methylene chloride (11 mL), and diisobutylaluminum hydride (1.0 M hexane solution) (2.5 mL, 2.50 mmol) was added dropwise on ice. The whole was stirred for 1 hour. After the stirring, isopropanol (1.75 mL), silica gel, and distilled water were added to the reaction solution, and the whole was stirred for 30 minutes. The mixture was then filtered, and the solvent was removed by evaporation. After the solvent removal, the residue (containing $d_3$-aldehyde) was subjected to the next step without further purification.

Under an argon atmosphere, methyltriphenylphosphonium iodide (2.79 g, 6.90 mmol) was dissolved in dehydrated tetrahydrofuran solution (15 mL), and sodium hexamethyldisilazide (1.9 M tetrahydrofuran solution) (3.2 mL, 6.15 mmol) was added dropwise on ice. The reaction mixture was stirred at the same temperature for 30 minutes, and then a solution of $d_3$-aldehyde (599 mg, 2.46 mmol) in tetrahydrofuran was added dropwise. The reaction mixture was stirred at the same temperature for another 1 hour. After the stirring, distilled water (20 mL) was added to the reaction solution, and the mixture was extracted with ethyl acetate. The organic phase was dried over anhydrous magnesium sulfate and was filtered, and the solvent was removed by evaporation. The residue was purified by silica gel column chromatography (hexane) to give $d_3$-alkyne 10 (461 mg, yield over 2 steps: 61%) as a colorless liquid. The $d_3$-alkyne 10 is also referred to as "alkyne compound 10" in the present description.

$^1$H NMR (300 MHz, CDCl$_3$) δ 5.89-5.76 (m, 1H), 5.03 (dd, J=16.9, 1.8 Hz, 1H), 4.96 (d, J=10.1 Hz, 1H), 2.21-2.00 (m, 2H), 1.97 (s, 1H), 1.79-1.66 (m, 1H), 1.66-1.58 (m, 1H), 0.89 (s, 9H), 0.07 (d, J=4.6 Hz, 6H).

(2) Synthesis of Alkyne Compound 17

Through the synthetic route shown below, an alkyne compound 17 was produced. As shown in the synthetic route, the alkyne compound 17 was synthesized by using $d_3$-alkyne 7 described in the above section (1). Each reaction in the synthetic route will be described below.

[Chemical Formula 26]

IBX
DMSO
72%

7

Ph$_3$P / CO$_2$Et

CH$_2$Cl$_2$, 0° C.
99%

11

Ti(O$^i$Pr)$_4$, L-(+)-DET
TBHP, MS4A

CH$_2$Cl$_2$, -20° C.
91%

13

I$_2$, PPh$_3$
imidazole

THF, -20° C.
88%

14

Zn, AcOH
MeOH
99%

15

(2S, 3R)-
HyperBTM
iPr$_2$NEt,
(CO$^i$Pr)$_2$O toluene,
-60° C.
82%

16

16

TBSCl, imidazole
DMAP

CH$_2$Cl$_2$
82%

17

(2-1) Synthesis of d$_3$-Alkyne 11

[Chemical Formula 27]

7

11

Under an argon atmosphere, d$_3$-alkyne 7 (0.80 g, 3.46 mmol) was dissolved in dimethyl sulfoxide (34.6 mL), and 2-iodoxybenzoic acid (1.93 g, 6.91 mmol) was added. The whole was stirred at 50° C. for 1.5 hours. After the stirring, a saturated aqueous sodium thiosulfate solution (34.6 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=50/1) to give d$_3$-alkyne 11 (0.57 g, yield: 72%) as a colorless liquid.

$^1$H NMR (300 MHz, CDCl$_3$) δ 9.82 (t, J=1.8 Hz, 1H), 2.77-2.64 (m, 2H), 2.02 (s, 1H), 0.86 (d, J=2.7 Hz, 9H), 0.09 (d, J=13.3 Hz, 6H).

HRMS (ESI, M+Na) calculated for C$_{12}$H$_{19}$D$_3$O$_2$SiNa 252.1475, found 252.1503.

(2-2) Synthesis of d$_3$-Alkyne 12

[Chemical Formula 28]

11

12

Under an argon atmosphere, d$_3$-alkyne 11 (0.55 g, 2.41 mmol) was dissolved in dehydrated methylene chloride (24.1 mL), and (ethoxycarbonylmethylene)triphenylphosphorane (1.68 g, 4.83 mmol) was added on ice. The whole was stirred for 1 hour. After the stirring, distilled water (24.1 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=100/1) to give d$_3$-alkyne 12 (0.72 g, yield: 99%) as a colorless liquid.

$^1$H NMR (300 MHz, CDCl$_3$) δ 6.99-6.91 (m, 1H), 5.88 (dd, J=15.6, 1.4 Hz, 1H), 4.18 (q, J=7.2 Hz, 2H), 2.54 (q, J=7.2 Hz, 1H), 2.42 (q, J=7.3 Hz, 1H), 2.00 (s, 1H), 1.28 (t, J=7.1 Hz, 3H), 0.88 (s, 9H), 0.07 (d, J=6.4 Hz, 6H).

HRMS (ESI, M+Na) calculated for C$_{16}$H$_{25}$D$_3$O$_3$SiNa 322.1894, found 322.1939.

(2-3) Synthesis of d$_3$-Alkyne 13

[Chemical Formula 29]

12

13

Under an argon atmosphere, d$_3$-alkyne 12 (0.72 g, 2.41 mmol) was dissolved in dehydrated toluene (24.1 mL), and diisobutylaluminum hydride (1.0 M hexane solution) (7.22 mL, 7.22 mmol) was added dropwise on ice. The whole was stirred for 0.5 hour. After the stirring, isopropanol (5.05 mL), silica gel, and distilled water (24.1 mL) were added to the reaction solution, and the whole was stirred. The mixture was filtered through Celite, and the solvent was removed by evaporation. After the solvent removal, the residue was purified by silica gel column chromatography (hexane/ethyl acetate=10/1) to give d$_3$-alkyne 13 (0.60 g, yield: 98%) as a colorless liquid.

$^1$H NMR (300 MHz, CDCl$_3$) δ 4.11 (d, J=4.1 Hz, 2H), 2.41-2.37 (m, 1H), 2.28 (dd, J=12.6, 4.4 Hz, 1H), 1.98 (s, 1H), 0.89 (s, 9H), 0.07 (d, J=6.9 Hz, 6H).

HRMS (ESI, M+Na) calculated for C$_{14}$H$_{23}$D$_3$O$_2$SiNa 280.1788, found 280.1791.

(2-4) Synthesis of d$_3$-Alkyne 14

[Chemical Formula 30]

13

14

Under an argon atmosphere, methylene chloride (18 mL) was added to MS4A (1.18 g), and Ti(O$^i$Pr)$_4$ (0.21 mL, 0.70 mmol), L-(+)-DET (0.15 mL, 0.85 mmol), and a solution of d$_3$-alkyne 13 (0.60 g, 2.35 mmol) in methylene chloride (6 mL) were added at −20° C. TBHP (3.5 M in CH$_2$Cl$_2$, 1.34 mL, 4.7 mmol) was added dropwise, and the whole was stirred at the same temperature for 1 hour. After the stirring, dimethyl sulfide (2.5 mL) and a saturated aqueous sodium fluoride solution (70 mL) were added to the reaction solution, and the whole was stirred for 12 hours. After the stirring, the reaction solution was filtered through Celite (methylene chloride), and the solvent was removed by evaporation. The residue was extracted with methylene chloride. The organic phase was dried over anhydrous magnesium sulfate and was filtered, and the solvent was removed by evaporation. The residue was purified by silica gel column chromatography (hexane/ethyl acetate=20/1) to give d$_3$-alkyne 14 (0.58 g, yield: 91%) as a colorless liquid.

$^1$H NMR (300 MHz, CDCl$_3$) δ 3.89 (dd, J=12.8, 2.3 Hz, 1H), 3.57 (dd, J=12.6, 4.4 Hz, 1H), 3.08-3.05 (m, 1H), 2.96-2.94 (m, 1H), 1.97 (s, 1H), 1.83-1.80 (m, 1H), 1.74 (q, J=7.2 Hz, 1H), 0.87 (s, 9H), 0.07 (s, 6H).

HRMS (ESI, M+Na) calculated for C$_{14}$H$_{23}$D$_3$O$_3$SiNa 296.1737, found 296.1736.

(2-5) Synthesis of d$_3$-Alkyne 15

[Chemical Formula 31]

Under an argon atmosphere, d$_3$-alkyne 14 (0.51 g, 1.85 mmol) was dissolved in dehydrated tetrahydrofuran solution (9.25 mL), and triphenylphosphine (1.46 g, 5.55 mmol), imidazole (756 mg, 11.1 mmol), and iodine (1.41 g, 5.55 mmol) were sequentially added at −20° C. The whole was stirred at the same temperature for 0.5 hour and then stirred at room temperature for 0.5 hour. After the stirring, a saturated aqueous sodium thiosulfate solution (9.25 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=80/1) to give d$_3$-alkyne 15 (0.62 g, yield: 88%) as a colorless liquid.

$^1$H NMR (400 MHz, CDCl$_3$) δ 3.24-3.19 (m, 1H), 3.13-3.00 (m, 2H), 2.99-2.95 (m, 1H), 1.98 (s, 1H), 1.90-1.82 (m, 1H), 1.74-1.66 (m, 1H), 0.89 (s, 9H), 0.09 (s, 6H).

HRMS (ESI, M+Na) calculated for C$_{14}$H$_{22}$D$_3$IO$_2$SiNa 406.0755, found 406.0762.

(2-6) Synthesis of d$_3$-Alkyne 16

[Chemical Formula 32]

In methanol (14.5 mL), d$_3$-alkyne 15 (0.58 g, 1.51 mmol) was dissolved, and acetic acid (0.58 mL) and zinc metal (346 mg, 5.29 mmol) treated with hydrochloric acid were added. The whole was stirred for 1 hour and was filtered through Celite, and the solvent was removed by evaporation. After the solvent removal, the residue was purified by silica gel column chromatography (hexane/ethyl acetate=80/1) to give d$_3$-alkyne 16 (0.41 g, yield: 99%) as a colorless liquid.

$^1$H NMR (400 MHz, CDCl$_3$) δ 5.92-5.82 (m, 1H), 5.30-5.24 (m, 1H), 5.10 (qt, J=5.0, 1.4 Hz, 1H), 4.42-4.38 (m, 1H), 1.99 (s, 1H), 1.93-1.73 (m, 2H), 0.90 (s, 9H), 0.11 (s, 6H).

HRMS (ESI, M+Na) calculated for C$_{14}$H$_{23}$D$_3$O$_2$SiNa 280.1788, found 280.1804.

(2-7) Optical Resolution of d$_3$-Alkyne 16

[Chemical Formula 33]

Under an argon atmosphere, d$_3$-alkyne 16 (333 mg, 1.29 mmol) was dissolved in dehydrated toluene (26 mL), and (2S,3R)-HyperBTM (40.1 mg, 0.13 mmol, 10% by mole), iPr$_2$NEt (68 μL), and (CO$^i$Pr)$_2$O (65 μL) were added at −60° C. The whole was stirred at −60° C. for 8 hours. After the stirring, distilled water (20 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=100/1) to give d$_3$-alkyne (−)-16 (270 mg, yield: 82%) as a colorless liquid.

(2-8) Synthesis of d₃-Alkyne 17

[Chemical Formula 34]

Under an argon atmosphere, d₃-alkyne (−)-16 (259.1 mg, 1.01 mmol) was dissolved in dimethyl formaldehyde (2.0 mL), and imidazole (116.4 mg, 1.71 mmol), tert-butyldimethylsilyl chloride (167 mg, 1.11 mmol), and 4-dimethylaminopyridine (6.8 mg, 0.056 mmol) were added. The whole was stirred at room temperature for 1 hour. After the stirring, distilled water (10 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=100/1) to give d₃-alkyne 17 (308.9 mg, yield: 82%) as a colorless liquid.

¹H NMR (400 MHz, CDCl₃) δ 5.87-5.76 (m, 1H), 5.20-5.02 (m, 2H), 4.23-4.19 (m, 1H), 1.97 (s, 1H), 1.91-1.78 (m, 1H), 1.65 (dd, J=13.8, 4.8 Hz, 1H), 0.89 (s, 18H), 0.09-0.04 (m, 12H).

HRMS (ESI, M+Na) calculated for $C_{20}H_{37}D_3O_3Si_2Na$ 394.2653, found 394.2677.

(3) Synthesis of Alkyne Compound 30

Through the synthetic route shown below, an alkyne compound 30 was produced. Each reaction in the synthetic route will be described below.

[Chemical Formula 35]

-continued

-continued (3-3) Synthesis of $d_5$-Ester 21

[Chemical Formula 38]

30

(3-1) Synthesis of $d_5$-Triol 19

[Chemical Formula 36]

Under a hydrogen atmosphere, triol 18 (1.62 g, 15.3 mmol) was dissolved in deuterium oxide (30 mL), and ruthenium/carbon (5%, 1.62 g, 16.0 mmol) was added at room temperature. The whole was stirred at 80° C. for 72 hours. After the stirring, the reaction solution was filtered through Celite (ethyl acetate/methanol=8/1), and the solvent was removed by evaporation. After the solvent removal, the residue was purified by silica gel column chromatography (ethyl acetate/methanol=8/1) to give $d_5$-triol 19 (1.62 g, yield: 100%) as a colorless liquid.

$^1$H NMR (300 MHz, D$_2$O) δ 3.13 (s, 1H), 1.45 (dd, J=31.0, 14.1 Hz, 2H).

HRMS (ESI, M+Na) calculated for C$_4$H$_5$D$_5$O$_3$Na 134.0842, found 134.0823.

(3-2) Synthesis of $d_5$-Alcohol 20

[Chemical Formula 37]

Under an argon atmosphere, d$_3$-triol 19 (500 mg, 4.50 mmol) was dissolved in acetone (7 mL), and p-toluenesulfonic acid (55.6 mg, 0.292 mmol) was added. The whole was stirred at room temperature for 12 hours. After the stirring, triethylamine (0.233 mL) was added to the reaction solution, and the solvent was removed by evaporation. After the solvent removal, the residue was purified by silica gel column chromatography (hexane/ethyl acetate=1/1) to give d$_5$-alcohol 20 (538 mg, yield: 79%) as a colorless liquid.

$^1$H NMR (300 MHz, CDCl$_3$) δ 2.10 (s, 1H), 1.81 (s, 2H), 1.43 (s, 3H), 1.36 (s, 3H).

HRMS (ESI, M+Na) calculated for C$_7$H$_9$D$_5$O$_5$Na 174.1155, found 174.1156.

Under an argon atmosphere, d$_5$-alcohol 20 (538 mg, 3.56 mmol) was dissolved in methylene chloride (7.1 mL), and triethylamine (1.49 mL, 10.7 mmol) and benzoyl chloride (0.615 mL, 5.34 mmol) were added. The whole was stirred at room temperature for 5 hours. After the stirring, distilled water (7 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=4/1) to give d$_5$-ester 21 (909 mg, yield: 100%) as a colorless liquid.

$^1$H NMR (300 MHz, CDCl$_3$) δ 8.04-8.01 (m, 2H), 7.58-7.53 (m, 1H), 7.45-7.41 (m, 2H), 2.08-1.96 (m, 2H), 1.42 (s, 3H), 1.36 (s, 3H).

HRMS (ESI, M+Na) calculated for C$_{14}$H$_{13}$D$_5$O$_4$Na 278.1417, found 278.1400.

(3-4) Synthesis of $d_5$-Diol 22

[Chemical Formula 39]

Ester 21 (909 mg, 3.56 mmol) was dissolved in distilled water (1.34 mL), and acetic acid (8.04 mL) was added at room temperature. The whole was stirred for 12 hours, and the solvent was removed by evaporation. After the solvent removal, the residue was purified by silica gel column chromatography (hexane/ethyl acetate=1/1) to give d$_5$-diol 22 (784 mg, yield: 88%) as a colorless liquid.

$^1$H NMR (300 MHz, CDCl$_3$) δ 8.03-8.00 (m, 2H), 7.58-7.52 (m, 1H), 7.45-7.40 (m, 2H), 2.73 (s, 2H), 1.85 (dd, J=23.4, 14.1 Hz, 2H).

HRMS (ESI, M+Na) calculated for C$_{11}$H$_9$D$_5$O$_4$Na 238.1104, found 238.1125.

(3-5) Synthesis of $d_5$-Bissilyl Ether 23

[Chemical Formula 40]

Under an argon atmosphere, $d_5$-triol 22 (784 mg, 3.64 mmol) was dissolved in methylene chloride (18 mL), and 2,6-lutidine (1.12 mL, 9.47 mmol) and tert-butyldimethylsilyl triflate (2.09 ml, 9.11 mmol) were added on ice. The whole was stirred at room temperature for 30 minutes. After the stirring, distilled water (18 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=20/1) to give $d_5$-bissilyl ether 23 (1.77 g, yield: 100%) as a colorless liquid.

$^1$H NMR (300 MHz, CDCl$_3$) δ 8.06-8.03 (m, 2H), 7.58-7.53 (m, 1H), 7.44 (t, J=7.6 Hz, 2H), 2.07 (d, J=14.1 Hz, 1H), 1.82-1.75 (m, 1H), 0.89 (s, 18H), 0.06 (t, J=2.4 Hz, 12H).

HRMS (ESI, M+Na) calculated for $C_{23}H_{37}D_5O_4Si_2Na$ 466.2833, found 466.2862.

(3-6) Synthesis of $d_5$-Alcohol 24

[Chemical Formula 41]

Under an argon atmosphere, $d_5$-bissilyl ether 23 (195 mg, 0.438 mmol) was dissolved in methanol (2 mL) and dichloromethane (2 mL), and camphorsulfonic acid (5.1 mg, 0.0219 mmol) was added. The whole was stirred at room temperature for 1 hour. After the stirring, a saturated aqueous sodium hydrogen carbonate solution (4 mL) was added to the reaction solution, and the solvent was removed by evaporation. After the solvent removal, the residue was purified by silica gel column chromatography (hexane/ethyl acetate) to give $d_5$-alcohol 24 (77 mg, yield: 58%) as a colorless liquid.

$^1$H NMR (300 MHz, CDCl$_3$) δ 8.04-8.01 (m, 2H), 7.59-7.54 (m, 1H), 7.44 (t, J=7.7 Hz, 2H), 2.02-1.76 (m, 2H), 0.94-0.89 (m, 9H), 0.12-0.07 (m, 6H).

HRMS (ESI, M+Na) calculated for $C_{17}H_{23}D_5O_4SiNa$ 352.1968, found 352.2010.

(3-7) Synthesis of $d_4$-Alkyne 25

[Chemical Formula 42]

Under an argon atmosphere, oxalyl chloride (0.24 mL, 2.8 mmol) was dissolved in dehydrated methylene chloride (7 mL), and dimethyl sulfoxide (0.497 mL, 7.00 mmol) was added dropwise at −78° C. The reaction mixture was stirred at the same temperature for 10 minutes, and a solution of $d_5$-alcohol 24 (461 mg, 1.40 mmol) in methylene chloride (7 mL) and triethylamine (1.94 mL, 14.0 mmol) were sequentially added dropwise. The reaction mixture was stirred at the same temperature for another 1 hour. After the stirring, distilled water (14 mL) was added to the reaction solution, and the mixture was extracted with ethyl acetate. The organic phase was dried over anhydrous magnesium sulfate and was filtered, and the solvent was removed by evaporation. After the solvent removal, the residue (containing $d_4$-aldehyde) was subjected to the next step without further purification.

Under an argon atmosphere, trimethylsilylacetylene (0.996 mL, 7.2 mmol) was dissolved in dehydrated tetrahydrofuran solution (12 mL), and n-butyllithium (2.6 M hexane solution) (2.3 mL, 6.0 mmol) was added dropwise at −78° C. to prepare a reaction mixture. The reaction mixture was stirred at the same temperature for 30 minutes, and then a solution of $d_4$-aldehyde (772 mg, 2.40 mmol) in tetrahydrofuran (12 mL) was sequentially added dropwise. After the dropwise addition, the reaction mixture was stirred at the same temperature for another 15 minutes. After the stirring, a saturated aqueous ammonium chloride solution (24 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=30/1) to give $d_4$-alkyne 25 (910 mg, yield: 90%) as a colorless liquid.

$^1$H NMR (300 MHz, CDCl$_3$) δ 8.06-8.02 (m, 2H), 7.59-7.54 (m, 1H), 7.45 (t, J=7.6 Hz, 2H), 2.38-1.89 (m, 2H), 0.93-0.90 (m, 9H), 0.16-0.06 (m, 15H).

HRMS (ESI, M+Na) calculated for $C_{22}H_{32}D_4O_4Si_2Na$ 447.2301, found 447.2289.

(3-8) Synthesis of $d_4$-Alkyne 26

[Chemical Formula 43]

Under an argon atmosphere, $d_4$-alkyne 25 (297 mg, 0.700 mmol) was dissolved in methylene chloride (7 mL), and 2,6-lutidine (0.199 mL, 1.68 mmol) and tert-butyldimethylsilyl triflate (0.193 ml, 0.840 mmol) were added on ice. The whole was stirred at room temperature for 1 hour. After the stirring, distilled water (7 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=40/1) to give $d_4$-bissilyl ether 26 (381 mg, yield: 100%) as a colorless liquid.

$^1$H NMR (300 MHz, CDCl$_3$) δ 8.06-8.03 (m, 2H), 7.55 (t, J=7.4 Hz, 1H), 7.44 (t, J=7.6 Hz, 2H), 2.19-1.90 (m, 2H), 0.93-0.87 (m, 18H), 0.24-0.03 (m, 21H).

HRMS (ESI, M+Na) calculated for $C_{28}H_{46}D_4O_4Si_3Na$ 561.3166, found 561.3141.

(3-9) Synthesis of $d_4$-Alkyne 27

[Chemical Formula 44]

In methanol (2 mL), $d_4$-alkyne 26 (314 mg, 0.587 mmol) was dissolved, and potassium carbonate (324 mg, 2.35 mmol) was added on ice. The whole was stirred at room temperature for 1 hour. After the stirring, distilled water (2 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=30/1) to give $d_4$-alcohol 27 (152 mg, yield: 76%) as a colorless liquid.

$^1$H NMR (300 MHz, CDCl$_3$) δ 2.41 (s, 1H), 1.99-1.59 (m, 2H), 0.90 (d, J=1.7 Hz, 18H), 0.16-0.09 (m, 12H).

HRMS (ESI, M+Na) calculated for $C_{18}H_{34}D_4O_3Si_2Na$ 385.2508, found 385.2549.

(3-10) Synthesis of $d_4$-Alkyne 28

[Chemical Formula 45]

Under an argon atmosphere, $d_4$-alcohol 27 (136 mg, 0.375 mmol) was dissolved in dehydrated tetrahydrofuran solution (1.6 mL), and triphenylphosphine (509 mg, 2.40 mmol), imidazole (76.6 mg, 1.13 mmol), and iodine (306 mg, 1.20 mmol) were sequentially added at −20° C. The whole was stirred for 30 minutes and then was stirred at room temperature for 20 minutes. After the stirring, a saturated sodium thiosulfate solution (1.6 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane) to give $d_4$-iodide 28 (174 mg, yield: 98%) as a colorless liquid.

$^1$H NMR (300 MHz, CDCl$_3$) δ 2.39 (s, 1H), 2.20-2.06 (m, 2H), 0.90 (d, J=2.1 Hz, 18H), 0.14-0.12 (m, 12H).

HRMS (ESI, M+Na) calculated for $C_{18}H_{33}D_4IO_2Si_2Na$ 495.1526, found 495.1497.

(3-11) Synthesis of $d_4$-Nitrile 29

[Chemical Formula 46]

Under an argon atmosphere, $d_4$-iodide 28 (174 mg, 0.369 mmol) was dissolved in dimethylformamide (0.9 mL), and sodium cyanide (27.1 mg, 0.554 mmol) was added at room temperature. The whole was stirred at 90° C. for 20 minutes. After the stirring, a saturated aqueous sodium hydrogen carbonate solution (1 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=80/1) to give $d_4$-nitrile 29 (130 mg, yield: 94%) as a colorless liquid.

<sup></sup>¹H NMR (300 MHz, CDCl₃) δ 2.42 (s, 1H), 1.98 (dd, J=24.1, 13.8 Hz, 2H), 0.90 (s, 18H), 0.14-0.11 (m, 12H).

$^1$H NMR (300 MHz, CDCl$_3$) δ 2.42 (s, 1H), 1.98 (dd, J=24.1, 13.8 Hz, 2H), 0.90 (s, 18H), 0.14-0.11 (m, 12H).

HRMS (ESI, M+Na) calculated for $C_{19}H_{33}D_4NO_2Si_2Na$ 394.2540, found 394.2512.

(3-12) Synthesis of $d_4$-Alkyne 30

[Chemical Formula 46]

Under an argon atmosphere, $d_4$-nitrile 29 (108 mg, 0.291 mmol) was dissolved in dehydrated dichloromethane (1.5 mL), and diisobutylaluminum hydride (1.0 M hexane solution) (0.35 mL, 0.35 mmol) was added dropwise on ice. The whole was stirred for 20 minutes. After the stirring, isopropanol (0.245 mL), silica gel (700 mg), and distilled water (1 mL) were added to the reaction solution, and the whole was stirred for 30 minutes. The mixture was filtered through Celite, and the solvent was removed by evaporation. After the solvent removal, the residue (containing $d_4$-aldehyde) was subjected to the next step without further purification.

Under an argon atmosphere, methyltriphenylphosphonium iodide (623 mg, 1.54 mmol) was dissolved in dehydrated tetrahydrofuran solution (1.5 mL), and sodium hexamethyldisilazide (1.9 M tetrahydrofuran solution) (0.766 mL, 1.46 mmol) was added dropwise on ice. The reaction mixture was stirred at the same temperature for 30 minutes, and then a solution of $d_4$-aldehyde (109 mg, 0.291 mmol) in tetrahydrofuran (1.5 mL) was added dropwise to prepare a reaction mixture. The reaction mixture was stirred at the same temperature for another 30 minutes. After the stirring, a saturated aqueous ammonium chloride solution (3 mL) was added to the reaction solution, and the mixture was extracted with ethyl acetate. The organic phase was dried over anhydrous magnesium sulfate and was filtered, and the solvent was removed by evaporation. The residue was purified by silica gel column chromatography (hexane/ethyl acetate=100/0) to give $d_4$-alkyne 30 (55.9 mg, yield: 52%) as a colorless liquid.

$^1$H NMR (300 MHz, CDCl$_3$) δ 5.88-5.77 (m, 1H), 5.05-4.94 (m, 2H), 2.35 (s, 1H), 1.78-1.56 (m, 2H), 0.91 (s, 18H), 0.12 (dd, J=13.8, 7.9 Hz, 12H).

HRMS (ESI, M+Na) calculated for $C_{20}H_{36}D_4O_2Si_2Na$ 395.2716, found 395.2699.

(4) Synthesis of Isotope-Unlabeled Alkyne Compound 42

In the experiments described later, isotope-unlabeled vitamin D compounds were used. To produce the vitamin D compounds, an isotope-unlabeled alkyne compound 42 was produced through the synthetic route shown below. Each reaction in the synthetic route will be described below.

[Chemical Formula 48]

-continued

41

1. DIBAL-H
   CH$_2$Cl$_2$, 0° C.

2. Ph$_3$PCH$_3$I, NaHMDS
   THF, 0° C.

52% (2 steps)

42

(4-1) Synthesis of Alcohol 32

[Chemical Formula 49]

31 p-TsOH•H$_2$O acetone

52%

32

Under an argon atmosphere, triol 31 (4.0 g, 37.3 mmol) was dissolved in acetone (60 mL), and p-toluenesulfonic acid (461 mg, 2.4 mmol) was added. The whole was stirred at room temperature for 12 hours. To the reaction solution, triethylamine (1.9 mL) was added, and the solvent was removed by evaporation. After the solvent removal, the residue was purified by silica gel column chromatography (hexane/ethyl acetate=1/1) to give alcohol 32 (2.8 g, yield: 52%) as a colorless liquid.

(4-2) Synthesis of Ester 33

[Chemical Formula 50]

32

BzCl, Et$_3$N

CH$_2$Cl$_2$

100%

33

Under an argon atmosphere, alcohol 32 (2.8 g, 3.6 mmol) was dissolved in methylene chloride (40 mL), and triethyl-amine (8 mL, 58.0 mmol) and benzoyl chloride (3.3 mL, 29.0 mmol) were added. The whole was stirred at room temperature for 5 hours. After the stirring, distilled water (40 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=4/1) to give ester 33 (4.8 g, yield: 100%) as a colorless liquid.

(4-3) Synthesis of Diol 34

[Chemical Formula 51]

33

AcOH

H$_2$O

88%

34

Ester 33 (5.6 g, 22.6 mmol) was dissolved in distilled water (6.5 mL), and acetic acid (40 mL) was added at room temperature. The whole was stirred for 12 hours, and the solvent was removed by evaporation. After the solvent removal, the residue was purified by silica gel column chromatography (hexane/ethyl acetate=1/1) to give diol 34 (4.4 g, yield: 88%) as a colorless liquid.

(4-4) Synthesis of Bissilyl Ether 35

[Chemical Formula 52]

34

TBSOTf,
2,6-lutidine

CH$_2$Cl$_2$, 0° C.

100%

35

Under an argon atmosphere, diol 34 (300 mg, 1.4 mmol) was dissolved in methylene chloride (7.0 mL), and 2,6-lutidine (0.44 mL, 3.7 mmol) and tert-butyldimethylsilyl triflate (0.82 ml, 3.6 mmol) were added on ice. The whole was stirred at room temperature for 30 minutes. After the stirring, distilled water (7.0 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=20/1) to give bissilyl ether 35 (627 mg, yield: 100%) as a colorless liquid.

(4-5) Synthesis of Alcohol 36

[Chemical Formula 53]

35

CSA,

MeOH/CH$_2$Cl$_2$

54%

36

Under an argon atmosphere, bissilyl ether 35 (627 mg, 1.4 mmol) was dissolved in methanol (8.5 mL) and dichloromethane (8.5 mL), and camphorsulfonic acid (40 mg, 0.17 mmol) was added. The whole was stirred at room temperature for 1 hour. After the stirring, a saturated aqueous sodium hydrogen carbonate solution (17 mL) was added to the reaction solution, and the solvent was removed by evaporation. After the solvent removal, the residue was purified by silica gel column chromatography (hexane/ethyl acetate=10/1) to give alcohol 36 (77 mg, yield: 54%) as a colorless liquid.

(4-6) Synthesis of Alkyne 37

[Chemical Formula 54]

(4-7) Synthesis of Alkyne 38

[Chemical Formula 55]

Under an argon atmosphere, alkyne 37 (264 mg, 0.63 mmol) was dissolved in methylene chloride (6.0 mL), and 2,6-lutidine (0.22 mL, 1.9 mmol) and tert-butyldimethylsilyl triflate (0.22 ml, 0.94 mmol) were added on ice. The whole was stirred at room temperature for 1 hour. After the stirring, distilled water (6.0 mL) was added to the reaction solution, and the mixture was extracted with methylene chloride. The organic phase was dried over anhydrous magnesium sulfate and was filtered, and the solvent was removed by evaporation. After the solvent removal, the residue was purified by silica gel column chromatography (hexane/ethyl acetate=40/1) to give alkyne 38 (334 mg, yield: 100%) as a colorless liquid.

$^{1}$H NMR (300 MHz, CDCl$_3$) δ 8.06-8.03 (m, 2H), 7.58-7.53 (m, 1H), 7.44 (t, J=7.4 Hz, 2H), 4.54-4.36 (m, 2H), 4.28 (d, J=4.5 Hz, 1H), 3.94-3.89 (m, 1H), 2.19-1.92 (m, 2H), 0.91-0.87 (m, 18H), 0.15-0.02 (m, 21H).

HRMS (ESI, M+Na) calculated for C$_{28}$H$_{50}$O$_4$Si$_3$Na 557.2915, found 557.2872.

(4-8) Synthesis of Alkyne 39

Under an argon atmosphere, oxalyl chloride (0.48 mL, 5.6 mmol) was dissolved in dehydrated methylene chloride (7.0 mL), and dimethyl sulfoxide (1.0 mL, 14.0 mmol) was added dropwise at −78° C. The reaction mixture was stirred at the same temperature for 10 minutes, and a solution of alcohol 36 (902 mg, 2.78 mmol) in methylene chloride (7.0 mL) and triethylamine (3.9 mL, 27.8 mmol) were sequentially added dropwise. The reaction mixture was stirred at the same temperature for another 1 hour. After the stirring, distilled water (14 mL) was added to the reaction solution, and the mixture was extracted with ethyl acetate. The organic phase was dried over anhydrous magnesium sulfate and was filtered, and the solvent was removed by evaporation. After the solvent removal, the residue was filtered by silica gel column chromatography (hexane/ethyl acetate=1/1) to give an aldehyde. The aldehyde was subjected to the next step without further purification.

Under an argon atmosphere, trimethylsilylacetylene (1.0 mL, 7.2 mmol) was dissolved in dehydrated tetrahydrofuran solution (12 mL), and n-butyllithium (2.6 M hexane solution) (2.3 mL, 6.0 mmol) was added dropwise at −78° C. The reaction mixture was stirred at the same temperature for 30 minutes, and then a solution of the aldehyde in tetrahydrofuran (12 mL) was sequentially added dropwise. The reaction mixture was stirred at the same temperature for another 15 minutes. After the stirring, a saturated aqueous ammonium chloride solution (24 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=30/1) to give alkyne 37 (910 mg, yield: 90%) as a colorless liquid.

$^{1}$H NMR (300 MHz, CDCl$_3$) δ 8.05-8.03 (m, 2H), 7.59-7.53 (m, 1H), 7.44 (t, J=7.6 Hz, 2H), 4.56-4.26 (m, 3H), 4.04-3.99 (m, 1H), 2.33-1.87 (m, 2H), 0.92-0.88 (m, 9H), 0.16-0.08 (m, 15H).

HRMS (ESI, M+Na) calculated for C$_{22}$H$_{36}$O$_4$Si$_2$Na 443.2050, found 443.2017.

[Chemical Formula 56]

Alkyne 38 (206 mg, 0.39 mmol) was dissolved in methanol (1.3 mL), and potassium carbonate (213 mg, 1.5 mmol) was added on ice. The whole was stirred at room temperature for 1 hour. After the stirring, distilled water (1.3 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=10/1) to give alkyne 39 (104 mg, yield: 76%) as a colorless liquid.

$^{1}$H NMR (300 MHz, CDCl$_3$) δ 4.36 (q, J=2.2 Hz, 1H), 3.94 (q, J=4.8 Hz, 1H), 3.80-3.75 (m, 2H), 2.41 (d, J=2.1 Hz, 1H), 2.15-1.82 (m, 3H), 0.90 (d, J=1.7 Hz, 18H), 0.16-0.09 (m, 12H).

HRMS (ESI, M+Na) calculated for $C_{18}H_{38}O_3Si_2Na$ 381.2257, found 381.2263.

(4-9) Synthesis of Iodide 40

[Chemical Formula 57]

Under an argon atmosphere, alkyne 39 (136 mg, 0.38 mmol) was dissolved in dehydrated tetrahydrofuran solution (1.6 mL), and triphenylphosphine (193 mg, 0.91 mmol), imidazole (76.6 mg, 1.1 mmol), and iodine (306 mg, 1.2 mmol) were sequentially added at −20° C. The whole was stirred for 30 minutes and then was stirred at room temperature for 20 minutes. After the stirring, a saturated sodium thiosulfate solution (1.6 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=100/0) to give iodide 40 (149 mg, yield: 84%) as a colorless liquid.

$^1$H NMR (300 MHz, CDCl$_3$) δ 4.25 (q, J=2.1 Hz, 1H), 3.79-3.68 (m, 1H), 3.41-3.18 (m, 2H), 2.39 (d, J=2.4 Hz, 1H), 2.19-2.12 (m, 2H), 0.90 (d, J=2.1 Hz, 18H), 0.14-0.12 (m, 12H).

HRMS (ESI, M+Na) calculated for $C_{18}H_{37}IO_2Si_2Na$ 491.1274, found 491.1243.

(4-10) Synthesis of Nitrile 41

[Chemical Formula 58]

Under an argon atmosphere, iodide 40 (133 mg, 0.28 mmol) was dissolved in dimethylformamide (0.7 mL), and sodium cyanide (21.0 mg, 0.43 mmol) was added at room temperature. The whole was stirred at 90° C. for 20 minutes. After the stirring, a saturated aqueous sodium hydrogen carbonate solution (1.0 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=80/1) to give nitrile 41 (105 mg, yield: 94%) as a colorless liquid.

$^1$H NMR (300 MHz, CDCl$_3$) δ 4.27 (q, J=2.1 Hz, 1H), 3.85-3.80 (m, 1H), 2.51-2.36 (m, 3H), 2.12-1.89 (m, 2H), 0.90 (s, 18H), 0.15-0.11 (m, 12H).

HRMS (ESI, M+Na) calculated for $C_{19}H_{37}NO_2Si_2Na$ 390.2261, found 390.2249.

(4-11) Synthesis of Alkyne 42

[Chemical Formula 59]

Under an argon atmosphere, nitrile 41 (32.5 mg, 0.089 mmol) was dissolved in dehydrated dichloromethane (0.4 mL), and diisobutylaluminum hydride (1.0 M hexane solution) (0.11 mL, 0.11 mmol) was added dropwise on ice. The whole was stirred for 20 minutes. After the stirring, isopropanol (0.074 mL), silica gel (200 mg), and distilled water (1 mL) were added to the reaction solution, and the whole was stirred for 30 minutes. The mixture was then filtered through Celite, and the solvent was removed by evaporation. After the solvent removal, the residue was filtered by silica gel column chromatography (hexane/ethyl acetate=10/1) to give an aldehyde. The aldehyde was subjected to the next step without further purification.

Under an argon atmosphere, methyltriphenylphosphonium iodide (623 mg, 1.5 mmol) was dissolved in dehydrated tetrahydrofuran solution (0.75 mL), and sodium hexamethyldisilazide (1.9 M tetrahydrofuran solution) (0.77 mL, 1.5 mmol) was added dropwise on ice. The reaction mixture was stirred at the same temperature for 30 minutes, and then a solution of the aldehyde (109 mg, 0.29 mmol) in tetrahydrofuran (0.75 mL) was added dropwise. The reaction mixture was stirred at the same temperature for another 30 minutes. After the stirring, a saturated aqueous ammonium chloride solution (3 mL) was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=100/0) to give alkyne 42 (55.9 mg, yield: 62%) as a colorless liquid.

$^1$H NMR (300 MHz, CDCl$_3$) δ 5.89-5.76 (m, 1H), 5.05-4.93 (m, 2H), 4.23 (q, J=2.3 Hz, 1H), 3.73 (dd, J=10.8, 4.6 Hz, 1H), 2.35 (d, J=2.4 Hz, 1H), 2.20-2.07 (m, 2H), 1.79-1.59 (m, 2H), 0.91 (s, 18H), 0.11 (dd, J=13.4, 7.6 Hz, 12H).

HRMS (ESI, M+Na) calculated for $C_{20}H_{40}O_2Si_2Na$ 391.2465, found 391.2442.

(6) Synthesis of Vitamin D Compound 44 (25OHD$_3$-3,4,4'-d$_3$, Also Referred to as "25OHD$_3$-d$_3$")

As shown in the following reaction scheme, alkyne compound 10 (d$_3$-alkyne 10) produced in the above section (1) was reacted with bromoolefin 43 to produce vitamin D compound 44.

[Chemical Formula 60]

43

+

10

1. Pd(PPh$_3$)$_4$, Et$_3$N, PhMe

2. MsOH, MeOH

44

Under an argon atmosphere, d$_3$-alkyne 10 (10 mg, 0.04 mmol) and bromoolefin 43 (29.3 mg, 0.06 mmol) were dissolved in dehydrated toluene (1.0 mL) and triethylamine (1.0 mL), and tetrakis(triphenylphosphine)palladium was added. The whole was stirred at 90° C. for 1 hour. After the stirring, the reaction solution was filtered through Celite (ethyl acetate), and the solvent was removed by evaporation. After the solvent removal, the residue (containing vitamin D3-3,25-bissilyl ether-d$_3$ described later (VD$_3$-3,25-bissilyl ether-d$_3$)) was filtered by silica gel column chromatography (hexane/ethyl acetate=50/1). The product was subjected to the next step without further purification.

Under an argon atmosphere, VD$_3$-3,25-bissilyl ether-d$_3$ was dissolved in methanol (0.5 mL), and methanesulfonic acid (10 μL) was added dropwise on ice. The whole was stirred for 30 minutes. After the stirring, a saturated aqueous sodium hydrogen carbonate solution was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=1:1) and reversed-phase HPLC to give vitamin D compound 44 (25OHD$_3$-d$_3$, 0.29 mg, yield over 2 steps: 1.8%) as a colorless solid.

The determined physical properties of the produced vitamin D compound 44 are shown below. The NMR spectrum is shown in FIG. 1A.

$^1$H NMR (400 MHz, CDCl$_3$) δ 6.23 (d, J=11.5 Hz, 1H), 6.03 (d, J=11.5 Hz, 1H), 5.05 (s, 1H), 4.82 (s, 1H), 2.82 (d, J=12.6 Hz, 1H), 2.37-2.42 (m, 1H), 2.15-2.20 (m, 1H), 1.96-2.04 (m, 2H), 1.84-1.94 (m, 2H), 1.25-1.70 (m, 16H), 1.21 (s, 6H), 0.95 (d, J=5.2 Hz, 3H), 0.54 (s, 3H).

HRMS (ESI, M+Na) calculated for C$_{27}$H$_{41}$D$_3$O$_2$Na 426.3427, found 426.3454.

(7) Synthesis of Vitamin D Compound 46 (25OHD$_3$-3,4,4'-d$_3$-26R,23S-Lactone, Also Referred to as "25OHD$_3$-26R, 23S-Lactone-d$_3$")

The same synthesis as in the section (6) was carried out except that bromoolefin 45 was used in place of bromoolefin 43 to synthesize vitamin D compound 46.

[Chemical Formula 61]

45

46

The determined physical properties of the produced vitamin D compound 46 are shown below. The NMR spectrum is shown in FIG. 1B.

$^1$H NMR (400 MHz, CDCl$_3$) δ 6.23 (d, J=11.4 Hz, 1H), 6.03 (d, J=10.5 Hz, 1H), 5.05 (s, 1H), 4.81 (s, 1H), 4.54-4.36 (m, 1H), 3.75-3.56 (m, 2H), 2.83 (d, J=12.8 Hz, 1H), 2.51-2.31 (m, 2H), 2.26-2.10 (m, 1H), 2.11-1.80 (m, 6H), 1.81-1.43 (m, 8H), 1.42-1.15 (m, 6H), 1.02 (d, J=6.4 Hz, 3H), 0.55 (s, 3H).

HRMS (ESI, M+Na) calculated for C$_{27}$H$_{37}$D$_3$O$_4$Na 454.3013, found 454.3009.

(8) Synthesis of Vitamin D Compound 47 (1α,25(OH)$_2$D$_3$-3,4,4'-d$_3$, Also Referred to as "1α,25(OH)$_2$D$_3$-d$_3$")

The same synthesis as in the section (6) was carried out except that alkyne compound 17 was used in place of alkyne compound 10 to synthesize vitamin D compound 47.

HRMS (ESI, M+Na) calculated for $C_{27}H_{37}D_3O_5Na$ 470.2962, found 470.2963.

(10) Synthesis of Vitamin D Compound 50 (24R,25 $(OH)_2D_3$-3,4,4'-$d_3$, Also Referred to as "24R,25$(OH)_2D_3$-$d_3$")

The same synthesis as in the section (6) was carried out except that bromoolefin 49 was used in place of bromoolefin 43 to synthesize vitamin D compound 50.

[Chemical Formula 62]

47

The determined physical properties of the produced vitamin D compound 47 are shown below.

The NMR spectrum is shown in FIG. 1C.

$^1$H NMR (300 MHz, CDCl$_3$) δ 6.38 (d, J=11.0 Hz, 1H), 6.01 (d, J=11.7 Hz, 1H), 5.33 (s, 1H), 5.00 (s, 1H), 4.42-4.42 (m, 1H), 2.82 (d, J=12.4 Hz, 1H), 1.25-2.05 (m, 20H), 1.21 (s, 6H), 0.93 (d, J=6.2 Hz, 3H), 0.54 (s, 3H).

HRMS (ESI, M+Na) calculated for $C_{27}H_{41}D_3O_3Na$ 442.3376, found 442.3336.

(9) Synthesis of Vitamin D Compound 48 (1α,25$(OH)_2D_3$-3,4,4'-$d_3$-26R,23S-Lactone, Also Referred to as "1α,25 $(OH)_2D_3$-26R,23S-Lactone-$d_3$")

The same synthesis as in the section (6) was carried out except that bromoolefin 45 was used in place of bromoolefin 43 and alkyne compound 17 was used in place of alkyne compound 10 to synthesize vitamin D compound 48.

[Chemical Formula 63]

48

The determined physical properties of the produced vitamin D compound 48 are shown below. The NMR spectrum is shown in FIG. 1D.

$^1$H NMR (300 MHz, CDCl$_3$) δ 6.37 (d, J=11.4 Hz, 1H), 6.01 (d, J=10.7 Hz, 1H), 5.33 (s, 1H), 5.00 (s, 1H), 4.46-4.46 (m, 2H), 2.83 (d, J=13.1 Hz, 1H), 2.39 (dd, J=13.2, 5.0 Hz, 1H), 1.25-2.05 (m, 20H), 1.02 (d, J=6.5 Hz, 3H), 0.55 (s, 3H).

[Chemical Formula 64]

49

50

The determined physical properties of the produced vitamin D compound 50 are shown below. The NMR spectrum is shown in FIG. 1E.

$^1$H NMR (400 MHz, CDCl$_3$) δ 6.23 (d, J=11.0 Hz, 1H), 6.03 (d, J=11.4 Hz, 1H), 5.05 (s, 1H), 4.82 (s, 1H), 3.34 (t, J=6.0 Hz, 1H), 2.83 (d, J=12.8 Hz, 1H), 2.35-2.42 (m, 1H), 2.18-2.20 (m, 1H), 1.16-2.01 (m, 24H), 0.94 (d, J=6.4 Hz, 3H), 0.55 (s, 3H).

HRMS (ESI, M+Na) calculated for $C_{27}H_{41}D_3O_3Na$ 442.3376, found 442.3402.

(11) Synthesis of Vitamin D Compound 51 (1α,24R,25 $(OH)_3$-3,4,4'-$d_3D_3$, Also Referred to as "1α,24R,25 $(OH)_3D_3$-$d_3$")

The same synthesis as in the section (6) was carried out except that bromoolefin 49 was used in place of bromoolefin 43 and alkyne compound 17 was used in place of alkyne compound 10 to synthesize vitamin D compound 51.

[Chemical Formula 65]

51

The determined physical properties of the produced vitamin D compound 51 are shown below. The NMR spectrum is shown in FIG. 1F.

$^1$H NMR (500 MHz, CD$_3$OD) δ 6.36 (d, J=11.5 Hz, 1H), 6.12 (d, J=11.5 Hz, 1H), 5.33 (s, 1H), 4.90 (s, 1H), 4.38 (t, J=6.0 Hz, 1H), 3.24 (d, J=9.7 Hz, 1H), 2.87-2.92 (m, 1H), 1.24-2.09 (m, 18H), 1.20 (s, 3H), 1.16 (s, 3H), 1.00 (d, J=6.3 Hz, 3H), 0.62 (s, 3H).

HRMS (ESI, M+Na) calculated for C$_{27}$H$_{41}$D$_3$O$_4$Na 458.3326, found 458.3334.

(12) Synthesis of Vitamin D Compound 52 (4β,25(OH)$_2$D$_3$-1,1',3,4-d$_3$, Also Referred to as "4β,25(OH)$_2$D$_3$-d$_4$")

The same synthesis as in the section (6) was carried out except that alkyne compound 30 was used in place of alkyne compound 10 to synthesize vitamin D compound 52.

[Chemical Formula 66]

43

+

30

1. Pd(PPh$_3$)$_4$, Et$_3$N, PhMe

2. TBAF, THF

52

Under an argon atmosphere, alkyne compound 30 (d$_4$-alkyne, 6.5 mg, 0.027 mmol) and bromoolefin 43 (9.8 mg, 0.032 mmol) were dissolved in dehydrated toluene (0.3 mL) and triethylamine (0.3 mL), and tetrakis(triphenylphosphine)palladium was added. The whole was stirred at 90° C. for 1 hour. After the stirring, the reaction solution was filtered through Celite (ethyl acetate), and the solvent was removed by evaporation. After the solvent removal, the residue (containing vitamin D$_3$-3,4,25-trisilyl ether-d$_4$ described later (VD$_3$-3,4,25-trisilyl ether-d$_4$)) was filtered by silica gel column chromatography (hexane/ethyl acetate=50/1). The product was subjected to the next step without further purification.

Under an argon atmosphere, VD$_3$-3,4,25-trisilyl ether-d$_4$ was dissolved in tetrahydrofuran solution (0.4 mL), and tetra-n-butylammonium fluoride (1 M tetrahydrofuran solution) (0.075 mL, 0.075 mmol) was added dropwise on ice. The whole was stirred for 12 hours. After the stirring, a saturated aqueous ammonium chloride solution was added to the reaction solution, and the mixture was extracted with ethyl acetate. The organic phase was dried over anhydrous magnesium sulfate and was filtered, and the solvent was removed by evaporation. After the solvent removal, the residue was purified by silica gel column chromatography (hexane/ethyl acetate=1:1) and reversed-phase HPLC to give vitamin D compound 52 (d4-4β,25(OH)$_2$ vitamin D$_3$, 1.8 mg, yield over 2 steps: 27%) as a colorless solid.

The determined physical properties of the produced vitamin D compound 52 are shown below. The NMR spectrum is shown in FIG. 1G.

$^1$H NMR (400 MHz, CDCl$_3$) δ 6.51 (d, J=11.4 Hz, 1H), 6.04 (d, J=11.4 Hz, 1H), 5.17 (d, J=2.3 Hz, 1H), 4.92 (d, J=2.3 Hz, 1H), 2.86 (d, J=13.7 Hz, 1H), 2.00-1.98 (m, 2H), 1.90-1.80 (m, 2H), 1.53-1.34 (m, 5H), 1.32-1.25 (m, 1H), 1.22 (s, 6H), 1.09-1.04 (m, 1H), 0.94 (d, J=6.4 Hz, 3H), 0.54 (s, 3H).

HRMS (ESI, M+Na) calculated for C$_{27}$H$_{40}$D$_4$O$_3$Na 443.3439, found 443.3459.

(13) Synthesis of Isotope-Unlabeled Vitamin D Compound 54 (4β,25(OH)$_2$D$_3$)

The same synthesis as in the section (12) was carried out except that isotope-unlabeled alkyne compound 53 was used in place of alkyne compound 30 to synthesize vitamin D compound 54.

[Chemical Formula 67]

53

54

The physical properties of the produced vitamin D compound 54 are shown below. The NMR spectrum is shown in FIG. 1H.

$^1$H NMR (500 MHz, CDCl$_3$) δ 6.51 (d, J=10.9 Hz, 1H), 6.04 (d, J=11.5 Hz, 1H), 5.17 (s, 1H), 4.92 (s, 1H), 4.22 (s, 1H), 3.86 (s, 1H), 2.86 (d, J=13.2 Hz, 1H), 2.38-2.35 (m, 1H), 2.18-2.13 (m, 1H), 2.01 (d, J=10.9 Hz, 2H), 1.85 (d, J=6.3 Hz, 3H), 1.71-1.33 (m, 17H), 1.21 (s, 6H), 1.05 (q, J=9.9 Hz, 1H), 0.93 (d, J=6.3 Hz, 3H), 0.54 (s, 3H).

HRMS (ESI, M+Na) calculated for C$_{27}$H$_{40}$D$_4$O$_3$Na 439.3188, found 439.3181.

6-2. Example 2: LC-MS/MS Analysis of 25OHD$_3$-26R,23S-Lactone and 1α,25(OH)$_2$D$_{3-26}$R,23S-Lactone in Pooled Serum The stable isotope-labeled vitamin D compounds synthesized in Example 1 were used to quantify two vitamin D compounds in a pooled serum by LC-MS/MS. The quantification was carried out in the following procedure.

(1) Preparation of Calibrator

Solutions of standard 25OHD$_3$-26R,23S-lactone or standard 1α,25(OH)$_2$D$_3$-26R,23S-lactone in 30% acetonitrile were prepared at the concentrations shown in Table 2.

TABLE 2

| | Calibrators | | | |
|---|---|---|---|---|
| | Cal1 | Cal2 | Cal3 | Cal4 |
| Concentration | 12.5 | 25 | 50 | 100 |

(2) Preparation of IS (Internal Standard) Solution

A solution of standard vitamin D compound 46 (25OHD$_3$-26R,23S-lactone-d$_3$) and standard vitamin D compound 48 (1α,25(OH)$_2$D$_3$-26R,23S-lactone-d$_3$) in 30% acetonitrile was prepared at the concentrations shown in Table 3.

TABLE 3

| | IS (internal standard) solution | |
|---|---|---|
| | 25OHD$_3$-26R,23S-lactone-d$_3$ | 1α,25(OH)$_2$D$_3$-26R,23S-lactone-d$_3$ |
| Concentration (pg/mL) | 200 | 200 |

(3) Sample Pretreatment

Samples were pretreated in the following procedure.

(3-1) SLE (solid-liquid) extraction

1) First, 100 μL of a serum and 200 μL of an IS solution were mixed.

2) Next, 300 μL of the serum/IS mixed solution was loaded on an SLE column.

3) Next, 600 μL of hexane/ethyl acetate (50/50, v/v) was added, and the sample was eluted.

The procedure was repeated three times.

(3-2) Drying: nitrogen blowing or centrifugal concentration for about 20 minutes.

(3-3) Derivatization

Figures 2G, 2H:
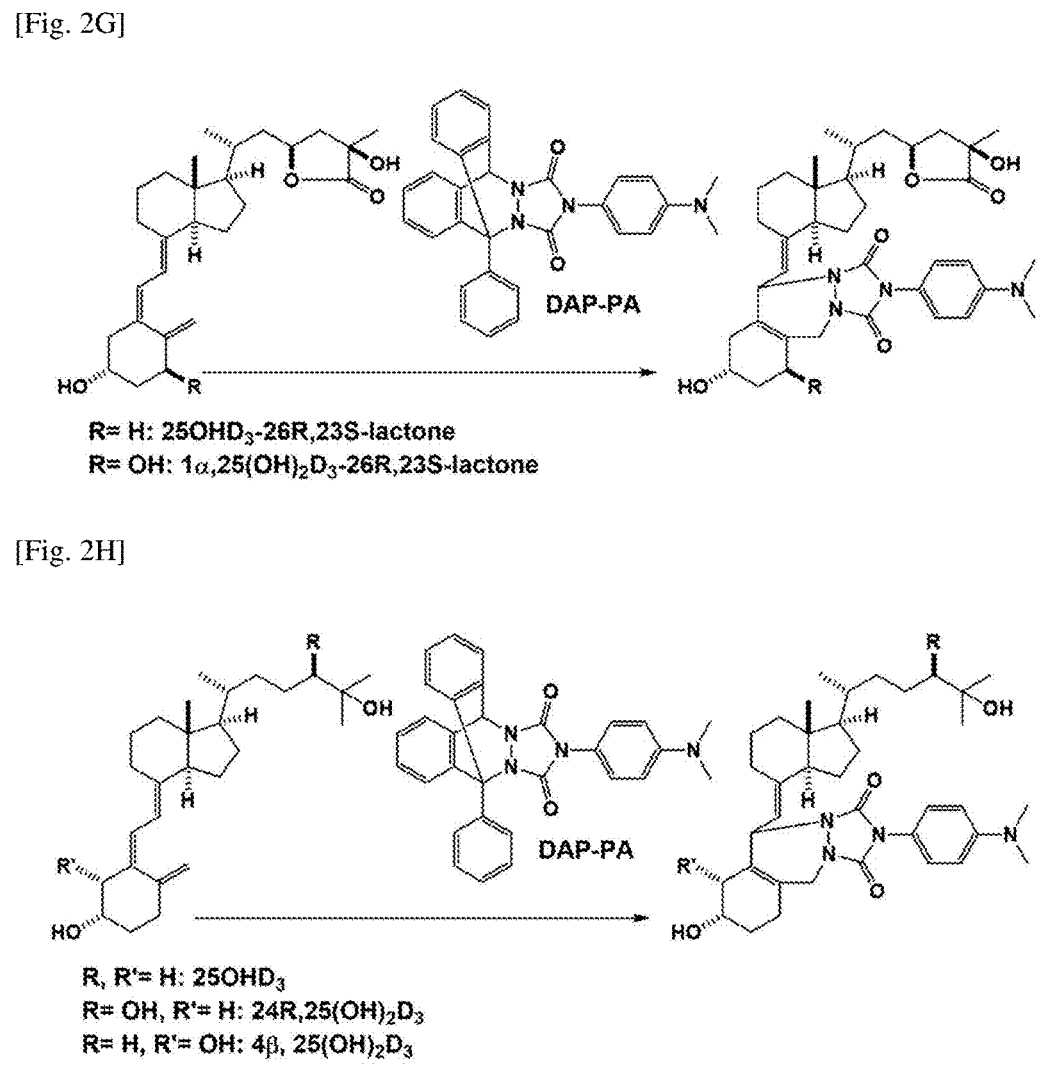

1) A derivatization reagent DAP-PA was preliminary warmed (80° C., 15 minutes) (the structure of DAP-PA and the derivatization reaction are as shown in FIG. 2G).

2) To the dried sample, 100 μL of DAP-PA (preliminary warmed) was added.

3) The mixture was allowed to stand at room temperature (15 minutes).

4) Drying: centrifugal concentration for about 15 minutes.

5) The residue was dissolved in 50 μL of a redissolving solution (50% acetonitrile).

(4) LC Analysis Conditions

LC analysis conditions are as follows:

Apparatus: ACQUITY UPLC I-Class (Waters)

Analytical column: CAPCELL CORE C18 2.1 mmI.D× 75 mm (Osaka Soda)

Elution conditions: flow rate, 0.4 mL/min; solvent A, 0.1% formic acid-water; solvent B, 0.1% formic acid-acetonitrile Detailed elution conditions are as shown in Table 4.

TABLE 4

| | Elution conditions | | | | | | | |
|---|---|---|---|---|---|---|---|---|
| | Time (min) | | | | | | | |
| | 0 | 2 | 3 | 3.5 | 4 | 4.01 | 4.7 | 6 |
| B (%) | 30 | 45 | 45 | 52 | 90 | 90 | 30 | 30 |

(5) MS/MS Analysis Conditions

MS/MS analysis conditions are as follows:

Apparatus: Xevo TQ-XS triple-quadrupole mass spectrometer (Waters)

Ionization conditions: ESI positive ion mode

SRM parameters were as shown in Table 5.

TABLE 5

| | SRM parameters | |
|---|---|---|
| | SRM (m/z) | CE (eV) |
| 25OHD$_3$-lactone-DAP | 647.4 > 341.2 | 28 |
| 25OHD$_3$-lactone-d$_3$-D AP | 650.4 > 344.2 | 28 |

TABLE 5-continued

| SRM parameters | | |
| --- | --- | --- |
| | SRM (m/z) | CE (eV) |
| 1α,25(OH)$_2$D$_3$-lactone-DAP | 663.4 > 357.2 | 28 |
| 1α,25(OH)$_2$D$_3$-lactone-d3-DAP | 666.4 > 360.2 | 28 |

(6) Analytical Results of Standards

The analytical results of standards are shown in FIG. 2A to FIG. 2D.

FIG. 2A shows SRM chromatograms of standard 25OHD$_3$-26R,23S-lactone-d$_3$.

FIG. 2B shows SRM chromatograms of standard 1α,25 (OH)$_2$D$_3$-26R,23S-lactone-d$_3$.

FIG. 2C shows a calibration curve of standard 25OHD$_3$-26R,23S-lactone.

FIG. 2D shows a calibration curve of standard 1α, 25(OH)$_2$D$_3$-26R,23S-lactone.

(7) Quantitative Values of 25OHD$_3$-26R,23S-Lactone and 1α,25(OH)$_2$D$_3$-26R,23S-Lactone in Pooled Serum On the basis of the above analytical results, 25OHD$_3$-26R,23S-lactone and 1α,25(OH)$_2$D$_3$-26R,23S-lactone in a pooled serum were quantified as shown in Table 6. In this manner, using the vitamin D compounds of the present invention as standards (specifically as internal standards) in mass spectrometry enables quantification of vitamin D metabolites in a sample (specifically in a biological sample).

FIG. 2E shows SRM chromatograms of 25OHD$_3$-26R, 23S-lactone in the pooled serum.

FIG. 2F shows SRM chromatograms of 1α,25(OH)$_2$D$_3$-26R,23S-lactone in the pooled serum.

TABLE 6

| Quantitative values of 25OHD$_3$-26R,23S-lactone and 1α,25(OH)$_2$D$_3$-26R,23S-lactone in pooled serum | |
| --- | --- |
| 25OHD$_3$-26R,23S-lactone | 38.3 pg/mL |
| 1α,25(OH)$_2$D$_3$-26R,23S-lactone | 8.9 pg/mL |

6-3. Example 3: LC-MS/MS Analysis of 25OHD$_3$ and 24R,25(OH)$_2$D$_3$ in Pooled Serum The stable isotope-labeled vitamin D compounds synthesized in Example 1 were used to quantify the two vitamin D compounds in a pooled serum by LC-MS/MS. The quantification was carried out in the following procedure.

(1) Calibrator

JeoQuant Kit for LC/MS/MS Analysis of Vitamin D Metabolites (JEOL) was used as a calibrator. The concentrations were shown in Table 7.

TABLE 7

| Calibrators | | | | |
| --- | --- | --- | --- | --- |
| Concentration (ng/mL) | Cal1 | Cal2 | Cal3 | Cal4 |
| 25OHD$_3$ | 0.876 | 8.78 | 43.9 | 87.8 |
| 24R,25(OH)$_2$D$_3$ | 0.096 | 0.96 | 4.81 | 9.6 |

(2) IS Solution

Solutions of standard vitamin D compound 44 (25OHD$_3$-d$_3$) and standard vitamin D compound 50 (24R,25(OH)$_2$D$_3$-d$_3$) in 30% acetonitrile were prepared at the concentrations shown in Table 8.

TABLE 8

| IS solutions | | |
| --- | --- | --- |
| | 25(OH)D$_3$-d$_3$ | 24R,25(OH)$_2$D$_3$-d$_3$ |
| Concentration (pg/mL) | 100 | 100 |

(3) Sample Pretreatment

Samples were pretreated in the following procedure.

(3-1) SLE (solid-liquid) extraction

1) First, 50 μL of a serum and IS solutions (20 μL of 25OHD$_3$-d$_3$, 2 μL of 24R,25(OH)$_2$D$_3$-d$_3$) were mixed, and the mixture was diluted with 230 μL of 30% acetonitrile solution.

2) Next, 302 μL of the serum/IS mixed solution was loaded on an SLE column.

3) Next, 600 μL of hexane/ethyl acetate (50/50, v/v) was added, and the sample was eluted.

The procedure was repeated twice.

(3-2) Centrifugal concentration for about 20 minutes (3-3) Derivatization

1) To the sample, 100 μL of a derivatization reagent DAP-PA was added, and the mixture was heated at 80° C. for 15 minutes (see FIG. 2H).

2) Drying: centrifugal concentration for about 15 minutes.

3) The residue was dissolved in 100 μL of a redissolving solution (50% acetonitrile).

(4) LC Analysis Conditions

Apparatus: UFLC LC-20AD (Shimadzu Corporation)

Analytical column: CAPCELL CORE C18 2.1 mmI.D× 100 mm (Osaka Soda)

Elution conditions: flow rate, 0.3 mL/min; solvent A, 0.1% formic acid-water; solvent B, 0.1% formic acid-acetonitrile Detailed elution conditions were as shown in Table 9.

TABLE 9

| Elution conditions | | | | | | |
| --- | --- | --- | --- | --- | --- | --- |
| | Time (min) | | | | | |
| | 0 | 0.5 | 3.5 | 3.51 | 5 | 5.01 | 6.5 |
| B (%) | 30 | 60 | 60 | 90 | 90 | 30 | 30 |

(5) MS/MS Analysis Conditions

Apparatus: LCMS8040 triple-quadrupole mass spectrometer (Shimadzu Corporation)

Ionization conditions: ESI positive ion mode

SRM parameters were as shown in Table 10.

TABLE 10

| SRM parameters | | |
| --- | --- | --- |
| | SRM (m/z) | CE (eV) |
| 25OHD$_3$-DAP | 619.5 > 341.2 | 24 |
| 25OHD$_3$-d$_3$-DAP | 622.5 > 344.2 | 24 |
| 24R,25(OH)$_2$D$_3$-DAP | 635.45 > 341.2 | 24 |
| 24R,25(OH)$_2$D$_3$-d$_3$-DAP | 638.45 > 344.2 | 24 |

(6) Analytical Results of Standards

The analytical results of standards are shown in FIG. 3A to FIG. 3D.

FIG. 3A is a calibration curve of standard 25OHD$_3$.

FIG. 3B is a calibration curve of standard 24R, 25(OH)$_2$D$_3$.

US 12,630,505 B2

63 64

(7) Quantitative Values of 25OHD$_3$ and 24R,25(OH)$_2$D$_3$ in Pooled Serum

On the basis of the above analytical results, 25OHD$_3$ and 24R,25(OH)$_2$D$_3$ in a pooled serum were quantified as shown in Table 11. In this manner, using the vitamin D compounds of the present invention as standards (specifically as internal standards) in mass spectrometry enables quantification of vitamin D metabolites in a sample (specifically a biological sample).

FIG. 3C shows an SRM chromatogram of 25OHD$_3$ in the pooled serum.

FIG. 3D shows an SRM chromatogram of 24R,25 (OH)$_2$D$_3$ in the pooled serum.

TABLE 11

| Quantitative values of 25OHD$_3$ and 24R,25(OH)$_2$D$_3$ in pooled serum | |
| --- | --- |
| 25OHD$_3$ | 5.06 ng/mL |
| 24R,25(OH)$_2$D$_3$ | 0.54 ng/mL |

6-4. Example 4: Separation Measurement of 4β,25-(OH)$_2$D$_3$

There are two or more vitamin D compounds having groups at different positions on the A ring or having different types of groups on the A ring, but the vitamin D compounds after derivatization for mass spectrometry may be cleaved to give fragments having the same molecular weight. The two or more vitamin D compounds have been difficult to separately detect or quantify.

Using the vitamin D compounds of the present invention and carrying out an analytical method in a particular procedure enable individual detection and/or quantification of the two or more vitamin D compounds.

An example quantification of 4β,25-(OH)$_2$D$_3$ by the analytical method will next be described.

(1) Material

Standard: 4β,25-(OH)$_2$D$_3$ (vitamin D compound 54 produced in Example 1)

Stable isotope-labeled compound: 4β,25-(OH)$_2$D$_3$-d$_4$ (vitamin D compound 52 produced in Example 1)

Vitamin D free serum: MSG1000 (Golden West Biologicals)

Antibody column: 1,25-(OH)$_2$-vitamin D$_3$/D$_2$ Immuno Tube (trademark) Extraction Kit (Immunodiagnostik)

SLE column: Isolute SLE+ column (Biotage)

Derivatization reagent (DAP-PA): JeoQuant Kit for LC-MS/MS Analysis of Vitamin D Metabolites (JEOL)

(2) IS (Internal Standard) Solution

An aqueous 4β,25-(OH)$_2$D$_3$-d$_4$ solution was prepared at the concentration shown below.

TABLE 12

| Concentration of IS (internal standard) solution | |
| --- | --- |
| | 4β,25-(OH)$_2$D$_3$-d$_4$ |
| Concentration (ng/mL) | 10 |

(3) Sample Pretreatment (3-1) In a microtube, 200 μL of a vitamin D free serum prepared to have a 4β,25-(OH)$_2$D$_3$ concentration of 50 pg/mL and 30 μL of IS were placed to prepare a sample.

(3-2) The sample was loaded on an antibody column, and the column sealed with a cap was gently shaken.

(3-3) The sample was rotated and mixed at room temperature for 1 hour with a rotator to be subjected to antigen-antibody reaction.

(3-4) The outlet of the antibody column was released, and the column was centrifuged at 550 g for 2 minutes to collect a non-adsorbed fraction.

(3-5) Into the column, 500 μL of WASHSOL supplied with the antibody column kit was added, and the column was centrifuged at 550 g for 2 minutes. The operation was repeated twice, and the eluate was discarded.

(3-6) Into the column, 250 μL of ELUREAG supplied with the antibody column kit was added, and the column was centrifuged at 550 g for 2 minutes to elute an adsorbed fraction, which was collected.

(3-7) The non-adsorbed fraction was loaded on an SLE column, was allowed to stand for 10 minutes, and was eluted with 600 μL of ethyl acetate/hexane (50/50, v/v). This operation was repeated three times, and the combined eluate was concentrated with a centrifugal evaporator.

(3-8) The adsorbed fraction was directly concentrated with a centrifugal evaporator.

(4) Derivatization

Each of the adsorbed fraction and the non-adsorbed fraction was subjected to derivatization as described below.

(4-1) A derivatization reagent was heated at 80° C. for 15 minutes, and 100 μL of the reagent was added to the concentrated, dried sample (see FIG. 2H).

(4-2) The mixture was allowed to stand for 15 minutes at room temperature and was concentrated with a centrifugal evaporator.

(4-3) The residue was dissolved in 50 μL of a redissolving solution (aqueous 50% acetonitrile solution).

(5) LC Analysis Conditions

After the derivatization treatment, liquid chromatography was carried out under the following conditions.

Apparatus: Agilent 1290 Infinity liquid chromatography system

Analytical column: CAPCELL CORE C18 2.1 mmI.D× 75 mm (Osaka Soda)

Elution conditions: flow rate, 0.4 mL/min; solvent A, 0.1% formic acid-water; solvent B, 0.1% formic acid-acetonitrile Detailed elution conditions were as shown in Table 13.

TABLE 13

| | Elution conditions | | | | | | | |
| --- | --- | --- | --- | --- | --- | --- | --- | --- |
| | Time (min) | | | | | | | |
| | 0 | 0.5 | 0.51 | 1.8 | 1.81 | 2.8 | 2.81 | 4 |
| B (%) | 50 | 50 | 65 | 65 | 90 | 90 | 50 | 50 |

(6) MS/MS Analysis Conditions

After the liquid chromatography, mass spectrometry was carried under the following conditions.

Apparatus: QTRAP4500 triple-quadrupole mass spectrometer (AB SCIEX)

Ionization conditions: ESI positive ion mode

SRM parameters were as shown in Table 14.

TABLE 14

| SRM parameters | | |
| --- | --- | --- |
| | SRM (m/z) | CE (eV) |
| 4β,25-(OH)$_2$D$_3$-DAP | 635.2 > 357.0 | 35 |
| 4β,25-(OH)$_2$D$_3$-d$_4$-DAP | 639.2 > 361.0 | 35 |
| 1α,25(OH)$_2$D$_3$-DAP | 635.2 > 357.0 | 35 |
| 1α,25(OH)$_2$D$_3$-$^{13}$C3-DAP | 638.2 > 357.0 | 35 |

(7) Analytical Results

FIG. 4A shows an SRM chromatogram of the non-adsorbed fraction of the antibody column.

FIG. 4B shows an SRM chromatogram of the adsorbed fraction of the antibody column.

These results showed that 4β,25-(OH)$_2$D$_3$ was contained in only in the non-adsorbed fraction of the antibody column. This reveals that by subjecting the non-adsorbed fraction to mass spectrometry, 4β,25-(OH)$_2$D$_3$ separated from other components can be detected and/or quantified.

6-5. Example 5: LC-MS/MS Analysis of 4β,25-(OH)$_2$D$_3$ in Pooled Serum (1) Materials Standards: 4β,25-(OH)$_2$D$_3$ (vitamin D compound 54 produced in Example 1), 1α,25-(OH)$_2$D$_3$(SIGMA)

Stable isotope-labeled compounds: 4β,25-(OH)$_2$D$_3$-d$_4$, (vitamin D compound 52 produced in Example 1), 1α,25-(OH)$_2$D$_3$-$^{13}$C$_3$ (SIGMA)

Vitamin D free serum: MSG1000 (Golden West Biologicals)

Antibody column: 1,25-(OH)$_2$-vitamin D$_3$/D$_2$ Immuno Tube (trademark) Extraction Kit (Immunodiagnostik)

SLE column: Isolute SLE+ column (Biotage)

Derivatization reagent (DAP-PA): JeoQuant Kit for LC-MS/MS Analysis of Vitamin D Metabolites (JEOL)

(2) Calibrators

To vitamin D free serums, 4β,25-(OH)$_2$D$_3$ was added at the following concentrations to prepare calibrators.

TABLE 15

| [Calibrators][] | | | | |
| --- | --- | --- | --- | --- |
| | Cal1 | Cal2 | Cal3 | Cal4 |
| Concentration (pg/mL) | 12.5 | 25 | 50 | 100 |

(3) IS (Internal Standard) Solution

An aqueous 4β,25-(OH)$_2$D$_3$-d$_4$ solution was prepared at the following concentration.

TABLE 16

| IS (internal standard) solution | |
| --- | --- |
| | 4β,25-(OH)$_2$D$_3$-d$_4$ |
| Concentration (pg/mL) | 200 |

(4) Sample Pretreatment (4-1) In a microtube, 200 μL of a calibrator or a pooled serum, 180 μL of IS, and 20 μL of additives were placed, and the whole was stirred to prepare a sample. To the calibrator, 10 μL of an aqueous 1α,25-(OH)$_2$D$_3$ solution (1 ng/mL) and 10 μL of an aqueous 1α,25-(OH)$_2$D$_3$-$^{13}$C$_3$ solution (1 ng/mL) were added as the additives. To the pooled serum, 10 μL of an aqueous 1α,25-(OH)$_2$D$_3$-$^{13}$C$_3$ solution (1 ng/mL) and 10 μL of water were added.

(4-2) The sample was loaded on an antibody column, and the column sealed with a cap was gently shaken.

(4-3) The sample was rotated and mixed at room temperature for 1 hour with a rotator to be subjected to antigen-antibody reaction.

(4-4) The outlet of the antibody column was released, and the column was centrifuged at 550 g for 2 minutes to collect a non-adsorbed fraction.

(4-5) Into the column, 500 μL of WASHSOL supplied with the antibody column kit was added, and the column was centrifuged at 550 g for 2 minutes. The operation was repeated twice, and the eluate was discarded.

(4-6) Into the column, 250 μL of ELUREAG supplied with the antibody column kit was added, and the column was centrifuged at 550 g for 2 minutes to elute an adsorbed fraction, which was collected.

(4-7) The non-adsorbed fraction was loaded on an SLE column, was allowed to stand for 10 minutes, and was eluted with 600 μL of ethyl acetate/hexane (50/50, v/v). This operation was repeated three times, and the combined eluate was concentrated with a centrifugal evaporator.

(4-8) The adsorbed fraction was directly concentrated with a centrifugal evaporator.

(5) Derivatization (5-1) A derivatization reagent was heated at 80° C. for 15 minutes, and 100 μL of the reagent was added to the concentrated, dried sample.

(5-2) The mixture was allowed to stand for 15 minutes at room temperature and was concentrated with a centrifugal evaporator.

(6) LC Analysis Conditions

Apparatus: Agilent 1290 Infinity liquid chromatography system

Analytical column: CAPCELL CORE C18 2.1 mmI.D× 100 mm (Osaka Soda)

Elution conditions: flow rate, 0.3 mL/min; solvent A, 0.1% formic acid-water; solvent B, 0.1% formic acid-acetonitrile

TABLE 17

| Elution conditions | | | | | | | |
| --- | --- | --- | --- | --- | --- | --- | --- |
| | Time (min) | | | | | | |
| | 0 | 0.5 | 7 | 7.01 | 8 | 8.01 | 9 |
| B (%) | 30 | 58 | 58 | 90 | 90 | 30 | 30 |

(7) MS/MS Analysis Conditions

Apparatus: QTRAP4500 triple-quadrupole mass spectrometer (AB SCIEX)

Ionization conditions: ESI positive ion mode

SRM parameters were as shown in Table 18.

TABLE 18

| SRM parameters | | |
| --- | --- | --- |
| | SRM (m/z) | CE (eV) |
| 4β,25-(OH)$_2$D$_3$-DAP | 635.2 > 357.0 | 35 |
| 4β,25-(OH)$_2$D$_3$-d$_4$-DAP | 639.2 > 361.0 | 35 |

TABLE 18-continued

| SRM parameters | | |
| --- | --- | --- |
| | SRM (m/z) | CE (eV) |
| $1\alpha,25(OH)_2D_3$-DAP | 635.2 > 357.0 | 35 |
| $1\alpha,25(OH)_2D_3$-$^{13}C_3$-DAP | 638.2 > 357.0 | 35 |

(8) Analytical Results

FIG. 5A shows a calibration curve of standard $4\beta,25$-$(OH)_2D_3$.

FIG. 5B shows SRM chromatograms of the antibody column non-adsorbed fraction of the pooled serum.

FIG. 5C shows SRM chromatograms of the antibody column adsorbed fraction of the pooled serum.

These results showed that $4\beta,25$-$(OH)_2D_3$ and $1\alpha,25$ $(OH)_2D_3$ were separated, and the $4\beta,25$-$(OH)_2D_3$ was collected in the non-adsorbed fraction of the antibody column, whereas the $1\alpha,25(OH)_2D_3$ was collected in the adsorbed fraction of the antibody column.

(9) Quantitative Value of $4\beta,25$-$(OH)_2D_3$ in Pooled Serum

TABLE 19

| Quantitative value of $4\beta,25$-$(OH)_2D_3$ in pooled serum | |
| --- | --- |
| $4\beta,25$-$(OH)_2D_3$ | 83.3 pg/mL |

This result reveals that $4\beta,25$-$(OH)_2D_3$ was separated from $1\alpha,25(OH)_2D_3$, and only $4\beta,25$-$(OH)_2D_3$ was detected and/or quantified.

The invention claimed is:

1. A vitamin D compound represented by Formula (III):

(III)

wherein in Formula (III),

A' is a cyclic carbon chain corresponding to an A ring of the vitamin D compound, $X'_1$ is C, $X'_2$ is CHY' or CDY', m is 4, $X'_2$s are identical or different, Y' is H, D, or OH, when Formula (III) contains two or more Y's, Y's are identical or different, $X'_3$ is C, at least one selected from the group consisting of $X'_2(s)$ is modified with a stable isotope D, and at least one among $X'_2(s)$ is CDD, P is a $C_1$ to $C_{10}$ alkyl group unsubstituted or substituted with a hydroxy group or a $C_2$ to $C_{10}$ alkenyl group unsubstituted or substituted with a hydroxy group, and the alkyl group or the alkenyl group optionally has a lactone group substituted with a hydroxy group, wherein the P has a structure:

wherein in the structure for P,

Q, Q', Q'', Q''', and Q'''' are each independently H, $CH_3$, or OH.

2. The vitamin D compound according to claim 1, a wherein in Formula (III), the P is a $C_1$ to $C_{10}$ alkyl group unsubstituted or substituted with a hydroxy group, and the alkyl group optionally has a lactone group substituted with a hydroxy group, wherein the P has a structure:

wherein in the structure for P,

Q', Q'', Q''', and Q'''' are each independently H or OH.

3. The vitamin D compound according to claim 1, wherein:

in Formula (III), the vitamin D compound is represented by Formula (200):

(200)

wherein in Formula (200),

A' is a cyclic carbon chain corresponding to an A ring of the vitamin D compound, $X'_1$ is C, $X'_{21}$, $X'_{22}$, $X'_{23}$, and $X'_{24}$ are each independently CHY' or CDY', Y' is H, D, or OH, when Formula (200) contains two or more Y's, Y's are identical or different, $X'_3$ is C, at least one selected from the group consisting of $X'_{21}$, $X'_{22}$, $X'_{23}$, and $X'_{24}$ is modified with a stable isotope D or at least two among $X'_{21}$, $X'_{22}$, $X'_{23}$, and $X'_{24}$ are modified with a stable isotope D, and at least one among $X'_{21}$, $X'_{22}$, $X'_{23}$, and $X'_{24}$ is CDD, P is a $C_1$ to $C_{10}$ alkyl group unsubstituted or substituted with a hydroxy group or a $C_2$ to $C_{10}$ alkenyl group unsubstituted or substituted with a hydroxy group, and the alkyl group or the alkenyl group optionally has a lactone group substituted with a hydroxy group, wherein the P has a structure:

wherein in the structure for P,

Q, Q', Q'', Q''', and Q'''' are each independently H, CH$_3$, or OH.

4. The vitamin D compound according to claim 3, wherein in Formula (200), the P is a $C_1$ to $C_{10}$ alkyl group unsubstituted or substituted with a hydroxy group, and the alkyl group optionally has a lactone group substituted with a hydroxy group, wherein the P has a structure:

wherein in the structure for P,

Q', Q'', Q''', and Q'''' are each independently H or OH.

* * * * *